US006989452B2

(12) United States Patent
Ng et al.

(10) Patent No.: US 6,989,452 B2
(45) Date of Patent: Jan. 24, 2006

(54) DISULFIDE PRODRUGS AND LINKERS AND STABILIZERS USEFUL THEREFOR

(75) Inventors: Howard P. Ng, El Sobrante, CA (US); Zhihong Li, Burlingame, CA (US); Danny P. C. McGee, Vista, CA (US); Oliver L. Saunders, Burlingame, CA (US); Guoxian Wu, Foster City, CA (US); David J. King, Belmont, CA (US); Valeri Martichonok, San Francisco, CA (US); Sharon Boyd, San Bruno, CA (US); Thomas J. Lobl, Foster City, CA (US)

(73) Assignee: Medarex, Inc., Princeton, NJ (US)

( * ) Notice: Subject to any disclaimer, the term of this patent is extended or adjusted under 35 U.S.C. 154(b) by 452 days.

(21) Appl. No.: 10/161,233

(22) Filed: May 31, 2002

(65) Prior Publication Data
US 2003/0073852 A1 Apr. 17, 2003

Related U.S. Application Data

(60) Provisional application No. 60/304,908, filed on Jul. 11, 2001, provisional application No. 60/295,342, filed on May 13, 2001, provisional application No. 60/295,259, filed on May 31, 2001, and provisional application No. 60/295,196, filed on May 31, 2001.

(51) Int. Cl.
C07D 487/00 (2006.01)
C07D 487/02 (2006.01)

(52) U.S. Cl. .................. 548/429; 514/291; 514/411; 424/70.1

(58) Field of Classification Search .............. 514/2, 514/183; 424/435
See application file for complete search history.

(56) References Cited

U.S. PATENT DOCUMENTS

| 4,169,888 A | 10/1979 | Hanka et al. ............... 424/121 |
| 4,671,958 A | 6/1987 | Rodwell et al. ............. 424/85 |
| 4,912,227 A | 3/1990 | Kelly et al. ................ 548/421 |
| 4,923,990 A | 5/1990 | Nakano et al. ............. 546/84 |
| 4,952,394 A | 8/1990 | Senter .................... 424/85.91 |
| 4,978,757 A | 12/1990 | Kelly et al. ................ 548/421 |
| 4,994,578 A | 2/1991 | Ohba et al. ............... 548/433 |
| 5,037,993 A | 8/1991 | Ohba et al. ............... 548/433 |
| 5,070,092 A | 12/1991 | Kanda et al. ............. 514/322 |
| 5,084,468 A | 1/1992 | Saito et al. ............... 514/367 |
| 5,101,038 A | 3/1992 | Nakano et al. ........... 548/421 |
| 5,117,006 A | 5/1992 | Saito et al. ............... 548/421 |
| 5,137,877 A | 8/1992 | Kaneko et al. ............. 514/25 |
| 5,138,059 A | 8/1992 | Takahashi et al. ........... 546/84 |
| 5,187,186 A | 2/1993 | Kanda et al. ............. 514/410 |
| 5,332,740 A | 7/1994 | Saito et al. ............... 514/253 |
| 5,332,837 A | 7/1994 | Kelly et al. ............... 548/433 |
| 5,475,092 A | 12/1995 | Chari et al. ............... 530/391 |
| 5,547,667 A | 8/1996 | Angelucci et al. ........ 424/181.1 |
| 5,585,499 A | 12/1996 | Chari et al. ............... 548/420 |
| 5,606,017 A | 2/1997 | Willner et al. ............. 530/322 |
| 5,622,929 A | 4/1997 | Willner et al. ................ 514/8 |
| 5,629,430 A | 5/1997 | Terashima et al. .......... 548/421 |
| 5,641,780 A | 6/1997 | Amishiro et al. ........... 514/253 |
| 5,703,080 A | 12/1997 | Nakakura et al. ........... 514/253 |
| 5,712,374 A | 1/1998 | Kuntsmann et al. ...... 530/391.7 |
| 5,714,586 A | 2/1998 | Kunstmann et al. ...... 530/391.7 |
| 5,739,350 A | 4/1998 | Kelly et al. ................ 548/421 |
| 5,773,001 A | 6/1998 | Hamann et al. ......... 424/181.1 |
| 5,773,435 A | 6/1998 | Kadow et al. .............. 514/214 |
| 5,786,377 A | 7/1998 | Garcia et al. ............... 514/410 |
| 5,786,486 A | 7/1998 | Fukuda et al. .............. 548/421 |
| 5,846,545 A | 12/1998 | Chari et al. ............. 424/195.11 |
| 5,877,296 A | 3/1999 | Hamann et al. ......... 530/391.7 |
| 5,985,908 A | 11/1999 | Boger ...................... 514/410 |
| 6,060,608 A | 5/2000 | Boger ...................... 548/420 |
| 6,066,742 A | 5/2000 | Fukuda .................... 548/433 |
| 6,103,236 A | 8/2000 | Suzawa et al. .......... 424/183.1 |
| 6,143,901 A | 11/2000 | Dervan .................... 548/312.4 |
| 6,194,612 B1 | 2/2001 | Boger et al. ............... 564/133 |
| 6,214,345 B1 | 4/2001 | Firestone et al. ........ 424/178.1 |
| 6,262,271 B1 | 7/2001 | Boger ...................... 546/201 |
| 6,281,354 B1 | 8/2001 | Boger ...................... 540/576 |
| 6,310,209 B1 | 10/2001 | Boger ....................... 546/69 |
| 6,329,497 B1 | 12/2001 | Boger ...................... 530/322 |
| 6,486,326 B2 | 11/2002 | Boger ...................... 546/201 |
| 6,512,101 B1 | 1/2003 | King et al. ................ 536/17.3 |
| 6,534,660 B1 | 3/2003 | Yongxin et al. ............ 548/450 |
| 6,548,530 B1 | 4/2003 | Boger ...................... 514/410 |
| 6,555,693 B2 | 4/2003 | Ge et al. ................ 548/512.4 |
| 6,566,336 B1 | 5/2003 | Sugiyama et al. ............ 514/18 |
| 6,586,618 B1 | 7/2003 | Zhao et al. ................ 560/100 |

FOREIGN PATENT DOCUMENTS

| EP | 0537575 A1 | 10/1992 |
| EP | 0689845 | 9/2002 |
| WO | WO 96/10405 | 4/1996 |
| WO | WO 97/12862 | 4/1997 |
| WO | WO97/32850 | 9/1997 |
| WO | WO97/45411 | 12/1997 |
| WO | WO 01/16324 | 3/2001 |
| WO | WO 01/49698 | 7/2001 |
| WO | WO 01/74898 | 10/2001 |
| WO | WO 01/83482 | 11/2001 |
| WO | WO 01/85733 | 11/2001 |
| WO | WO 02/083180 | 10/2002 |
| WO | WO 02/088172 | 11/2002 |
| WO | WO 03/022806 | 3/2003 |

OTHER PUBLICATIONS

International Search Report, issued in International Application No. PCT/US02/17210.

(Continued)

Primary Examiner—Christopher R Tate
Assistant Examiner—Marcela M Cordero Garcia
(74) Attorney, Agent, or Firm—Darby & Darby PC

(57) ABSTRACT

The present invention provides analogues of duocarmycins that are potent cytotoxins. Also provided are peptidyl and disulfide linkers that are cleaved in vivo. The linkers are of use in forming prodrugs and conjugates of the cytotoxins of the invention as well as other diagnostic and therapeutic moieties. The invention provides prodrugs and conjugates of the duocarmycin analogues with the linker arms of the invention.

21 Claims, 28 Drawing Sheets

OTHER PUBLICATIONS

Synthesis and Biochemical Evaluation of the CBI–PDE–I–dimer, a Benzannelated Analog of (+)–CC–1065 That Also Produces Delayed Toxicity in Mice, Paul A. Aristoff, *J. Med. Chem. 1993, 36, 1956–1963*.

CC–1065 and the Duocarmycins: Synthetic Studies, Dale L. Boger, *Chemical Review, vol. 97, No. 3, pp. 787–828*.

Synthesis, Chemical Properties, and Preliminary Evaluation of Substituted CBI Analogs of CC–1065 and the Duocarmycins . . . , Dale L. Boger, *J. Org. Chem. 1996, 61, 4894–4912*.

Duocarmycin SA Shortened, Simplified, and Extended Agents: A Systematic Examination of the Role of the DNA Binding subunit, Dale L. Boger, *J. Am. Chem. Soc., vol. 119, No. 21*, 1997 4979.

Synthesis and Preliminary Evaluation of (+)–CBI–Indole$_2$: An Enhanced Functional Analog (+)–CC–1065, Dale L. Boger, *Inorganic & Medicinal Chemistry Letters, vol. 1, No. 2, pp. 115–120, 1991*.

Synthesis of N–(tert–Butyloxycarbonyl)–CBI, CBI, CBI–CDPI and CBI–CDPI$_2$: Enhanced Functional Analogues of CC–1065 Incorporating the 1,2,9,9a–Tetrahydrocyclopropa[c]benz[e]indo–4–one (CBI) Left–Hand Subunit, Dale L. Boger et al., *Angew. J. Org. Chem, 1990, 55, 5823–5832*.

CC–1065 and the Duocarmycins: Understanding their Biological Function through Mechanistic Studies, Dale L. Boger et al., *Chem. Int. Ed. Engl. 1996, 35, 1438–1474*.

1,2,9,9a–Tetrahydrocyclopropa[c]benz[e]indol–4–one (CBI) Analogs of CC–1065 and the Duocarmycins: Synthesis and Evaluation, Dale L. Boger et al, *Biorganic & Medicinal Chemistry, vol. 3, No. 11, pp 1429–1453, 1995*.

Enhancement of the Selectivity and Antitumor Efficacy of a CC–1065 Analogue through Immunoconjugate Formation, Ravi V. J. Chari et al, *Cancer Research, 55, 4079–4084, Sep. 15, 1995*.

Snythesis and Biological Evaluation of 2'–Carbamate–Linked and 2'–Carbonate–Linked Prodrugs of Paclitaxel: Selective Activation by the Tumor–Associated Protease Plasmin, Franciscus M.H. de Groot, *J. Med. Chem. 2000, 43, 3093–3102*.

Novel Synthesis of Optically Active CC–1065, U–73,975 (Adozelesin), U–80,244 (Carzelesin), U–77,779 (Bizelesin), KW–2189 and DU–86[1], Yasumichi Fukuda, *Heterocycles, vol. 45, No. 12, 1997*.

Cytotoxicity and Antitumor Activity of Carzelesin, a Prodrug Cyclopropylpyrroloindole Analogue[1], L.H. Li, *Cancer Research 52, 4904–4913, Sep. 15, 1992*.

Synthesis and Antitumor Activity of Duocarmycin Derivatives: Modification of Segment A of Duocarmycin B2, Satoru Nagamura, *1996 Pharmaceutical Society of Japan*.

Synthesis and Antitumor Activity of Duocarmycin Derivatives, Satoru Nagamura, *Chem. Pharm. Bull, 43(9) 1530–1535 (1995)*.

Antitumor Antibiotics: Duocarmycins, Satoru Nagamura, *Chemistry of Heterocyclic Compounds, vol. 34, No. 12, 1998*.

Structure–Activity Relationships of (+)–CC–1065 Analogues in the Inhibition of Helicase,Catalyzed Unwinding of Duplex DNA, Daekyu sun, *Journal of Medicinal Chemistry, 1992, vol. 35, No. 10*.

Preparation and In Vitro Cytotoxicity of a Methotrexate–Anti–MM46 Monoclonal Antibody Conjugate Via An Oligopeptide Spacer, Naoji Umemoto, *Int. J. Cancer: 43, 677–684 (1989)*.

Dissecting the Complex Structure of CC–1065, Martha A Warpehoski, *Drugs of the Future 1991, 16(2) 131–141*.

Stereoelectronic Factors Influencing the Biological Activity and DNA Interaction of Synthetic Antitumor Agents Modeled on CC–1065, M.A.Warpehoski, *J. Med. Chem 1988, 31, 590–603*.

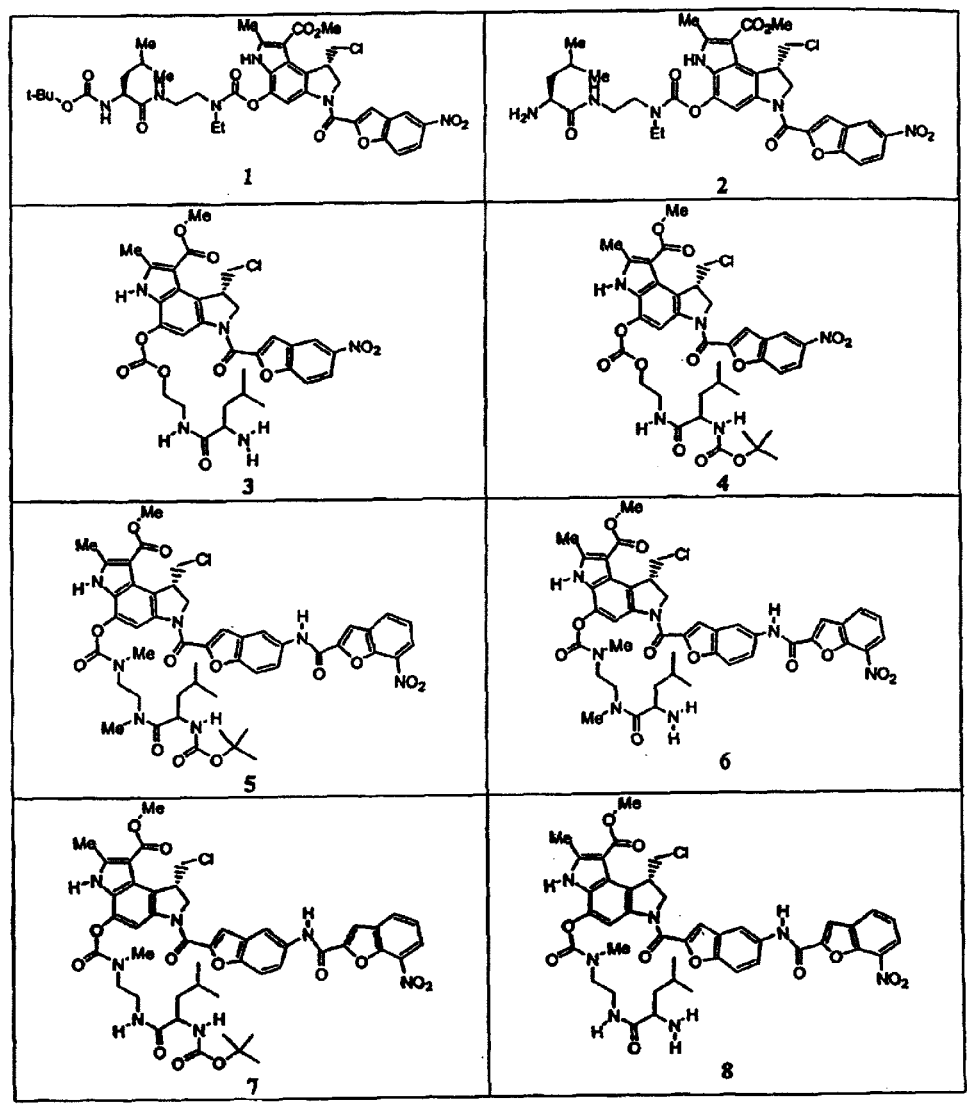
Figure 1.1

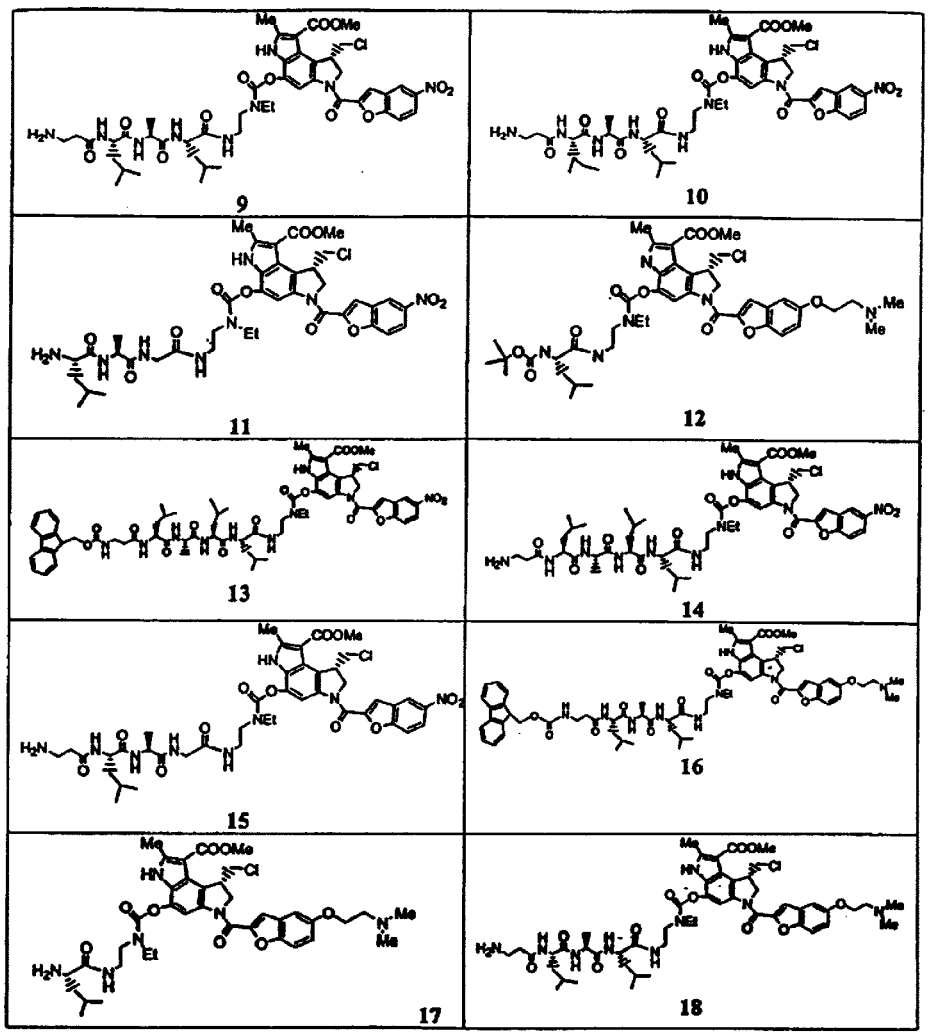
*Figure 1.2*

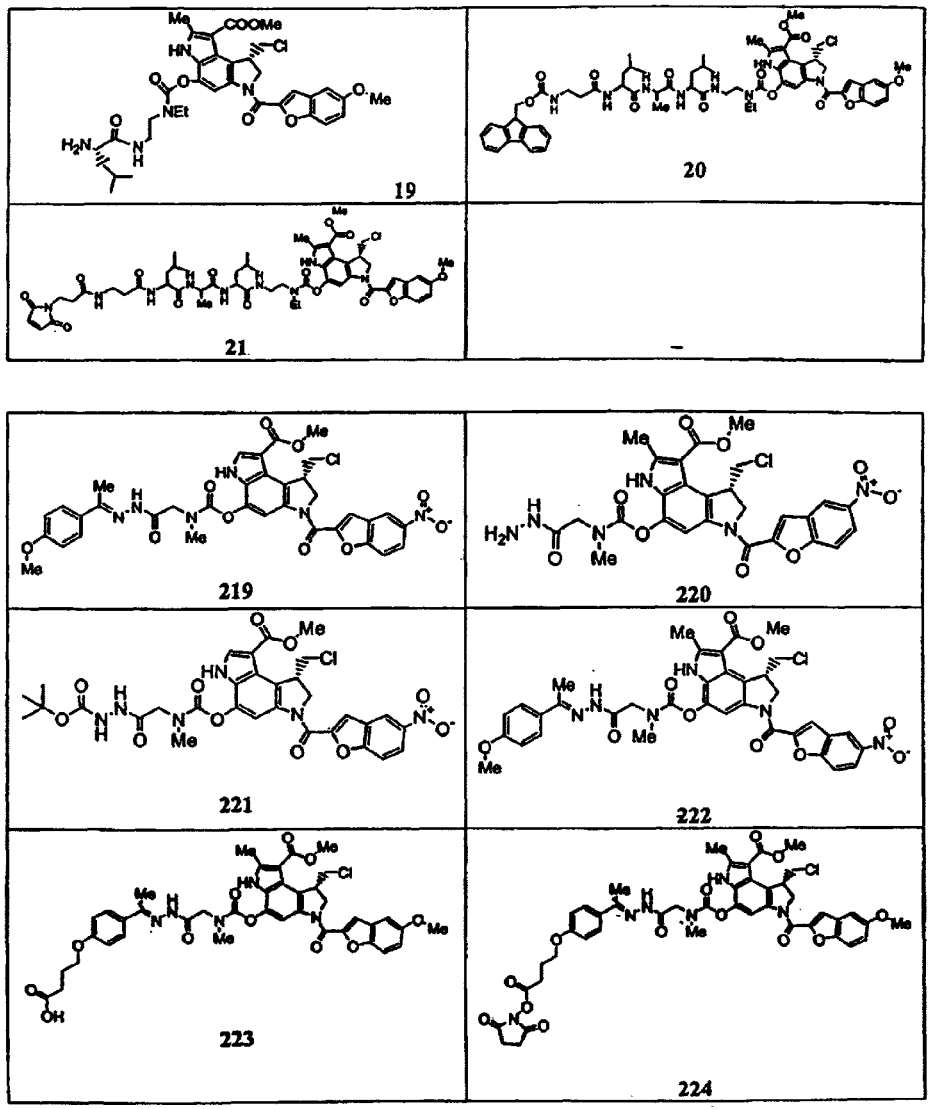
Figure 1.3

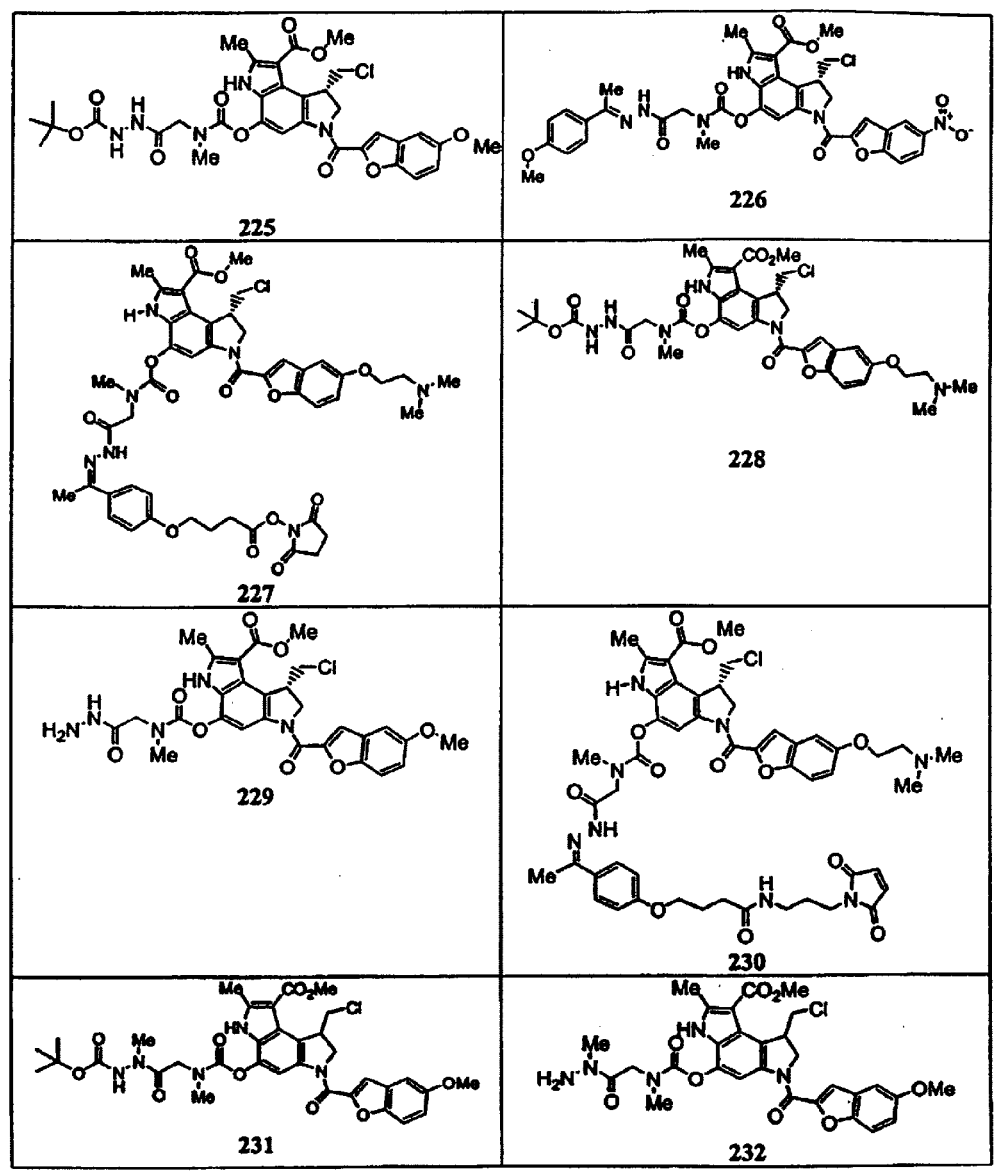
*Figure 1.4*

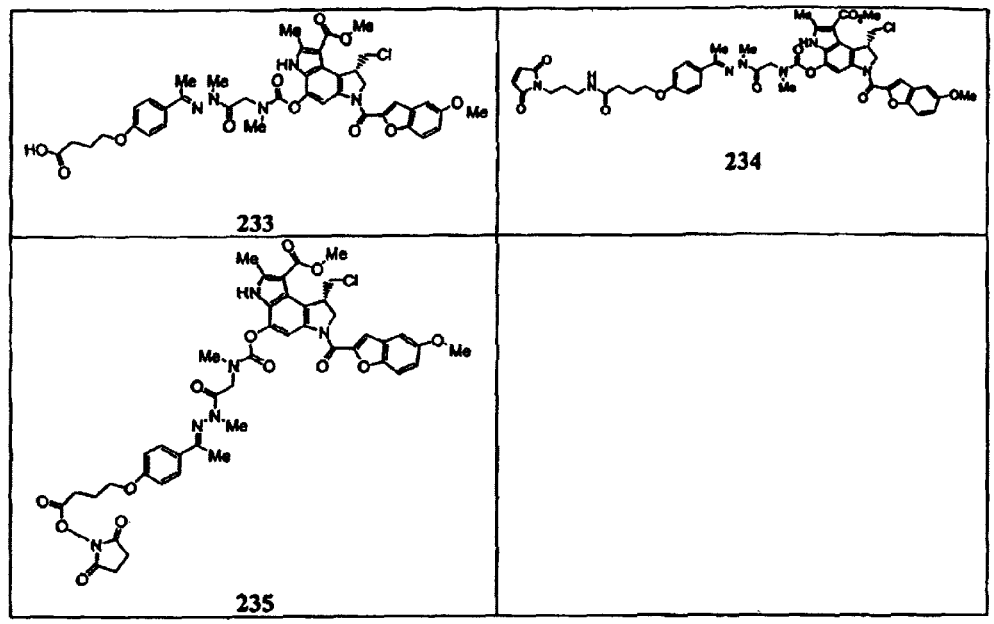
Figure 1.5

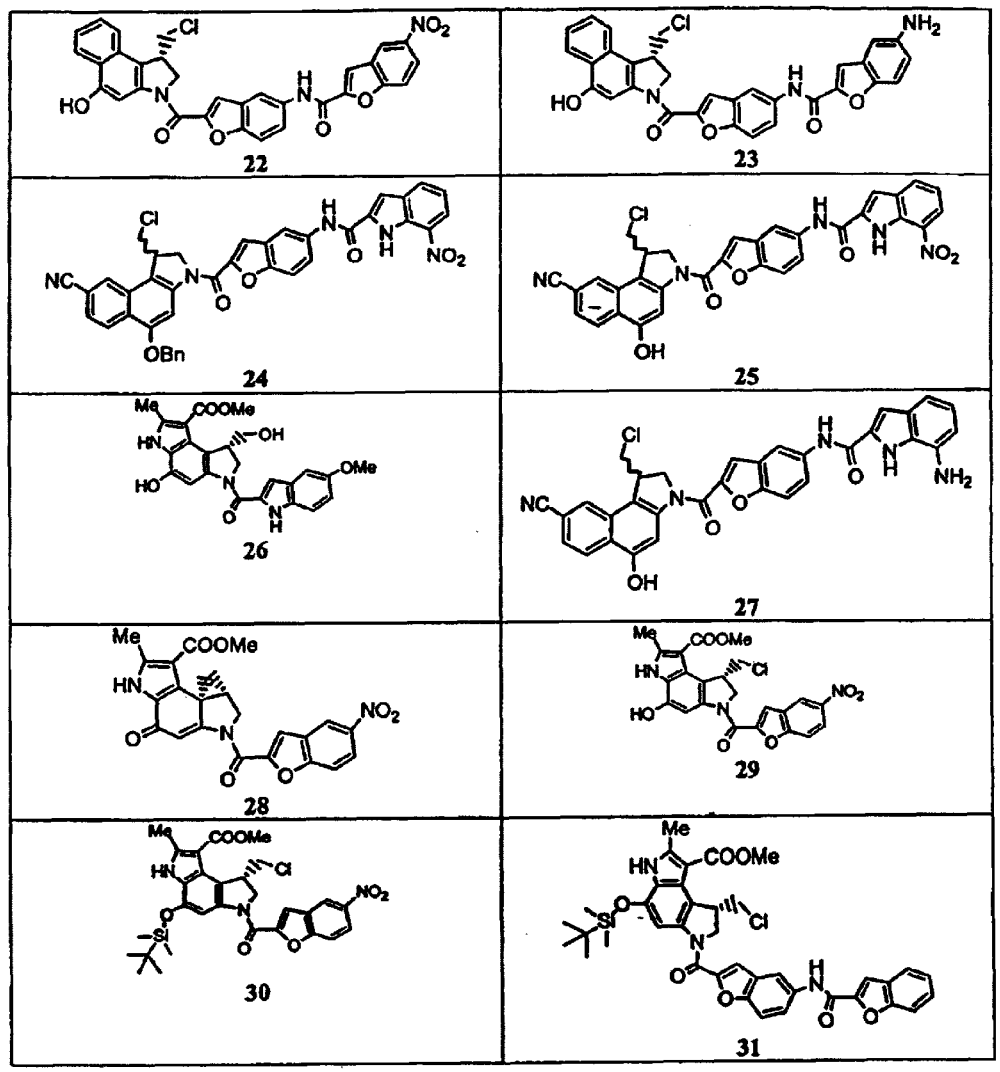
Figure 2.1

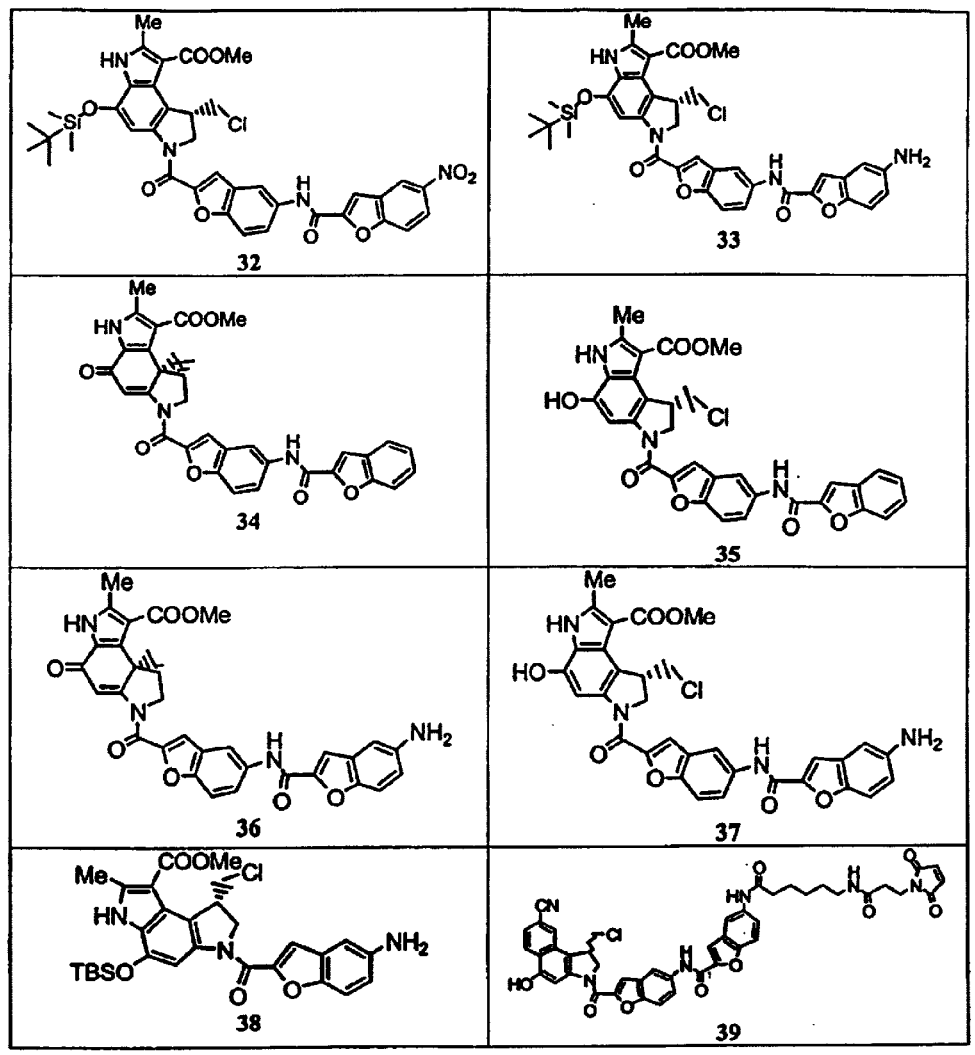
Figure 2.2

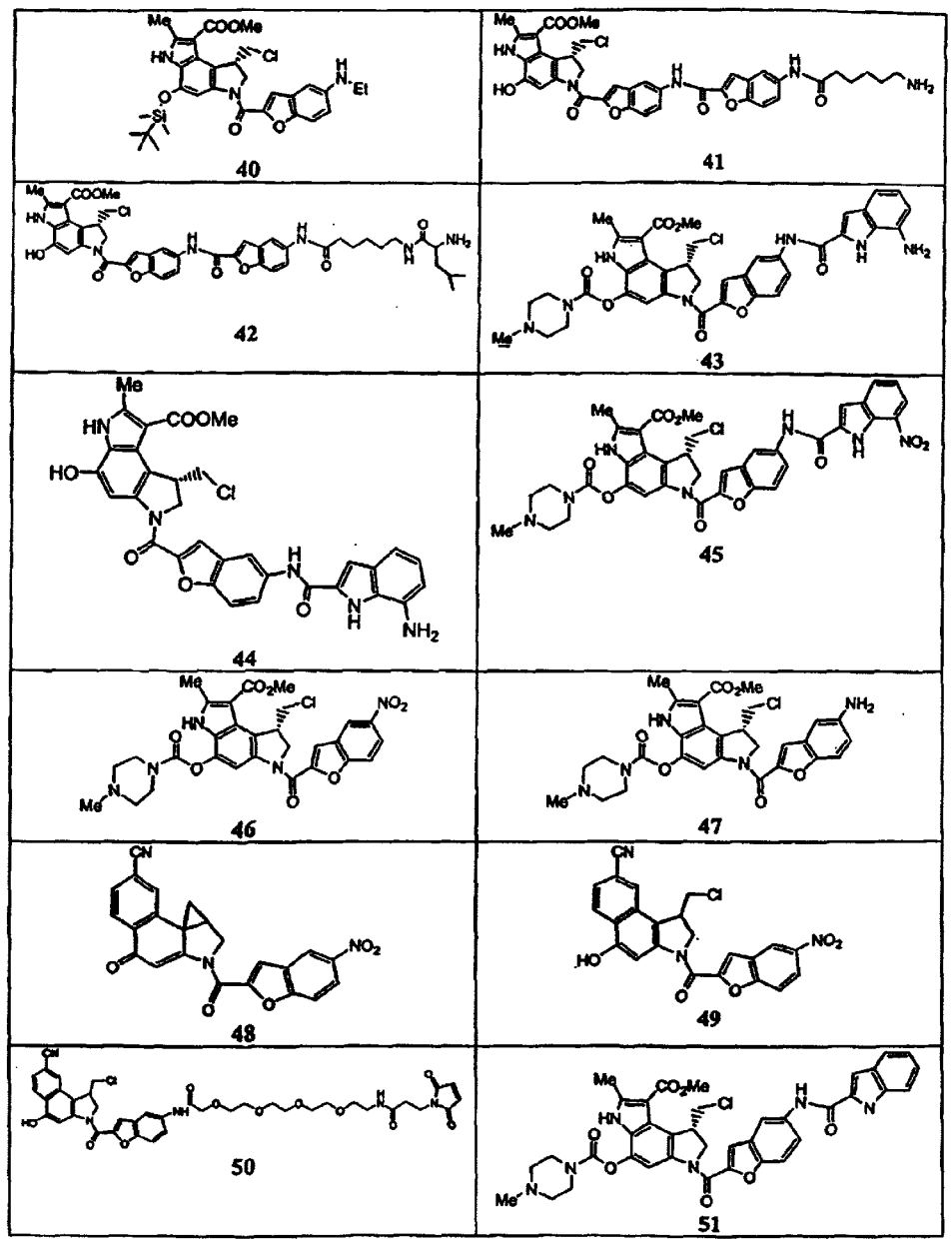
Figure 2.3

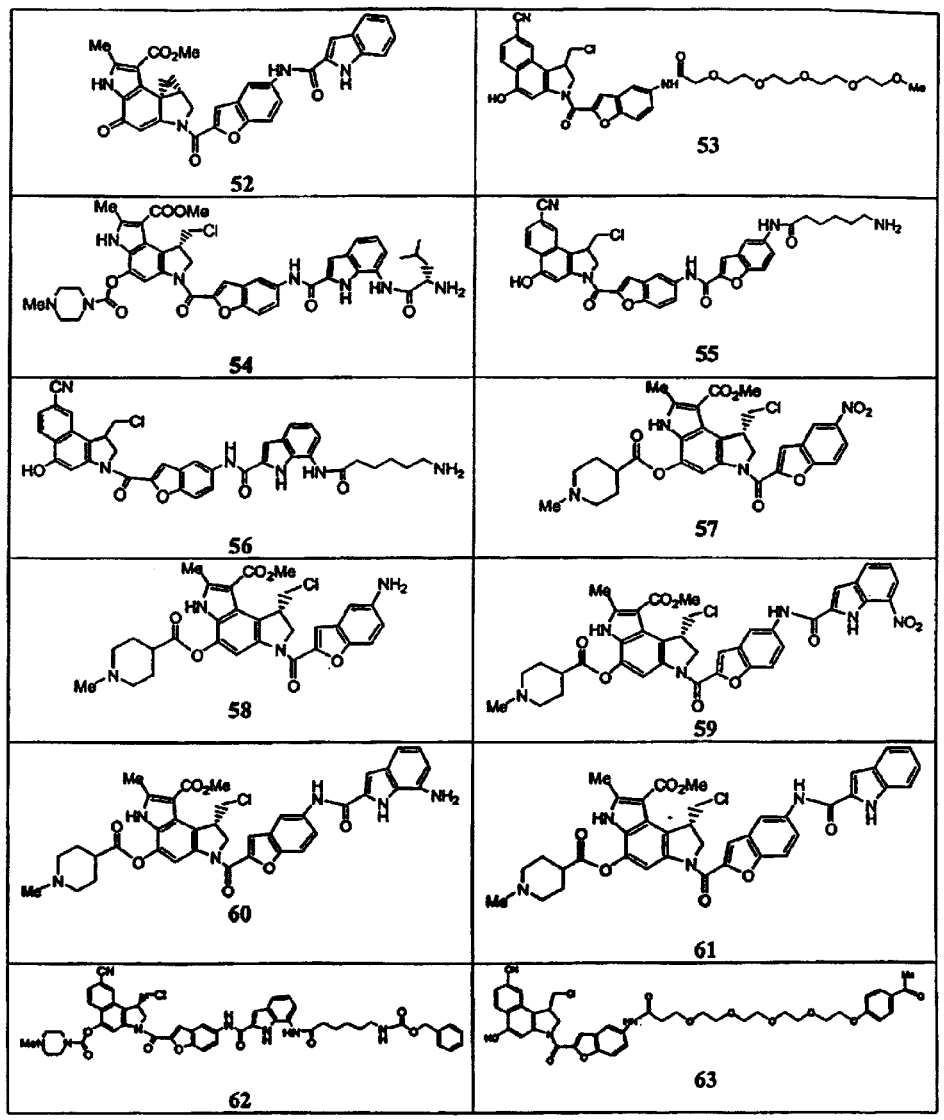
Figure 2.4

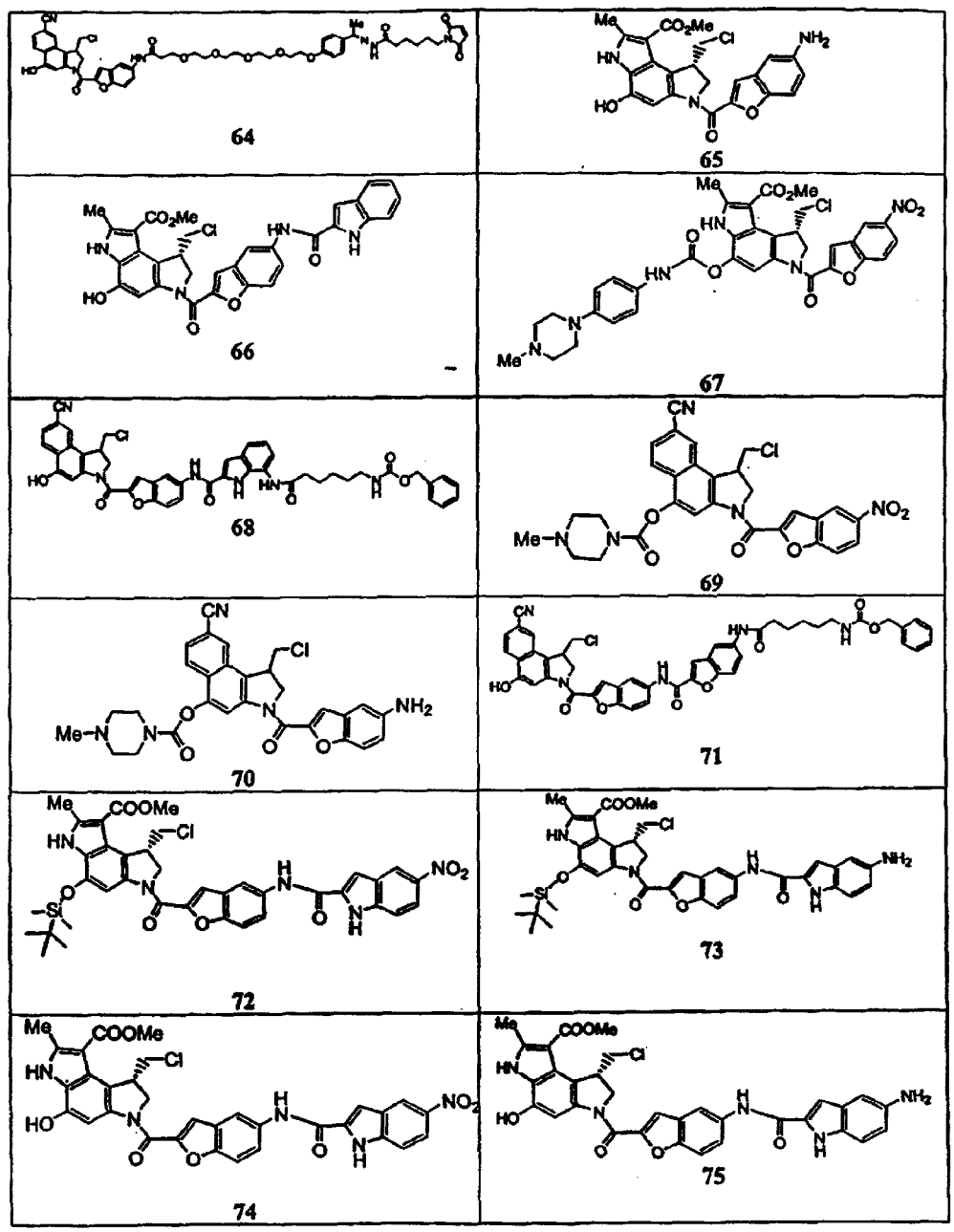
Figure 2.5

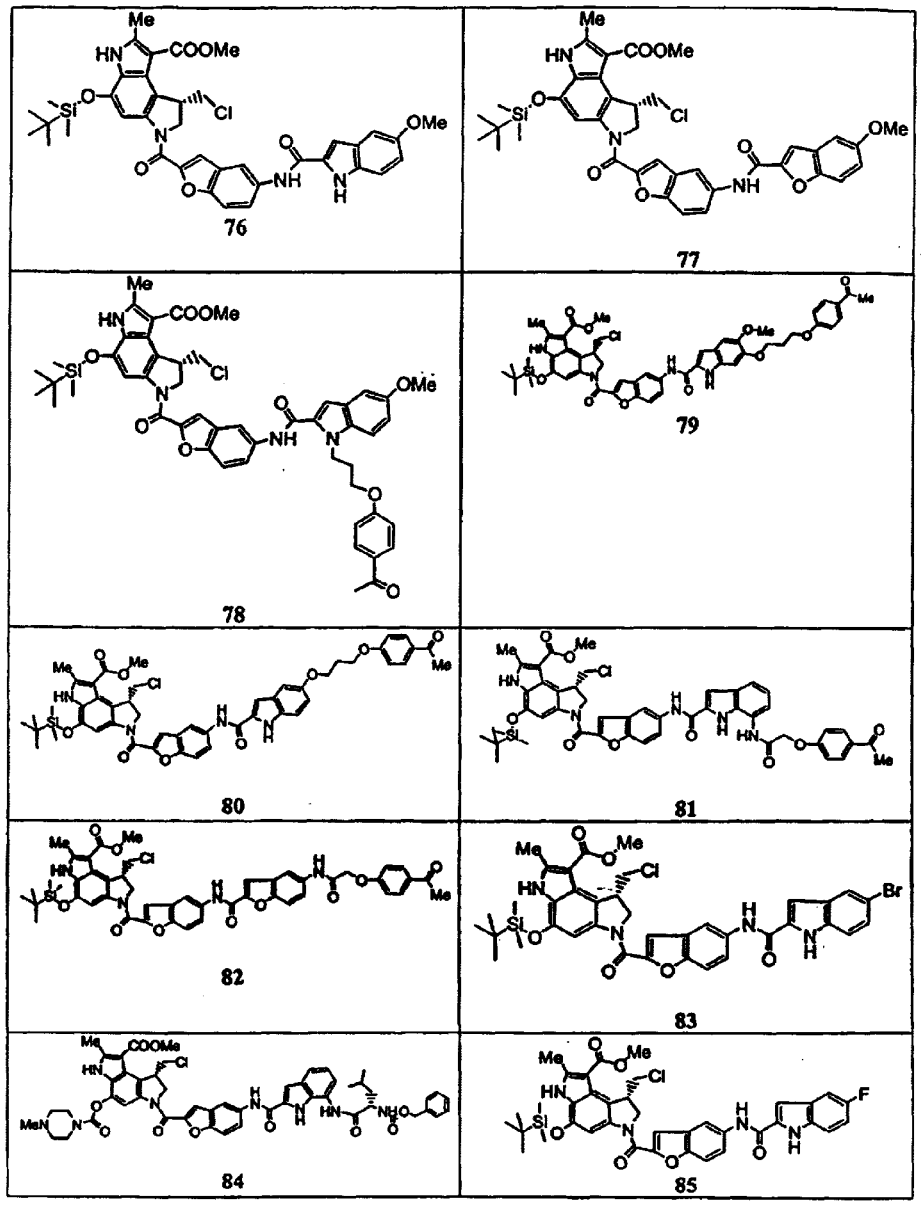
*Figure 2.6*

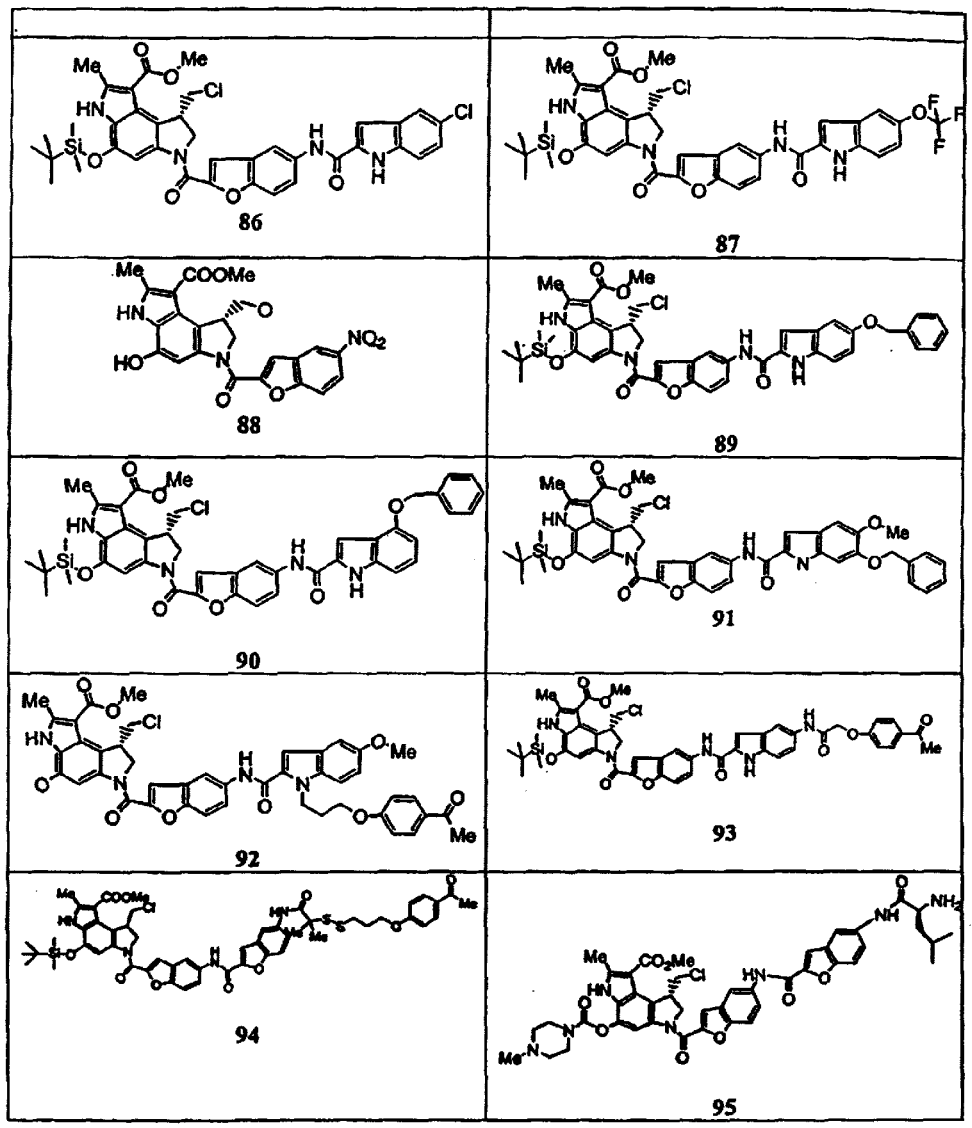
Figure 2.7

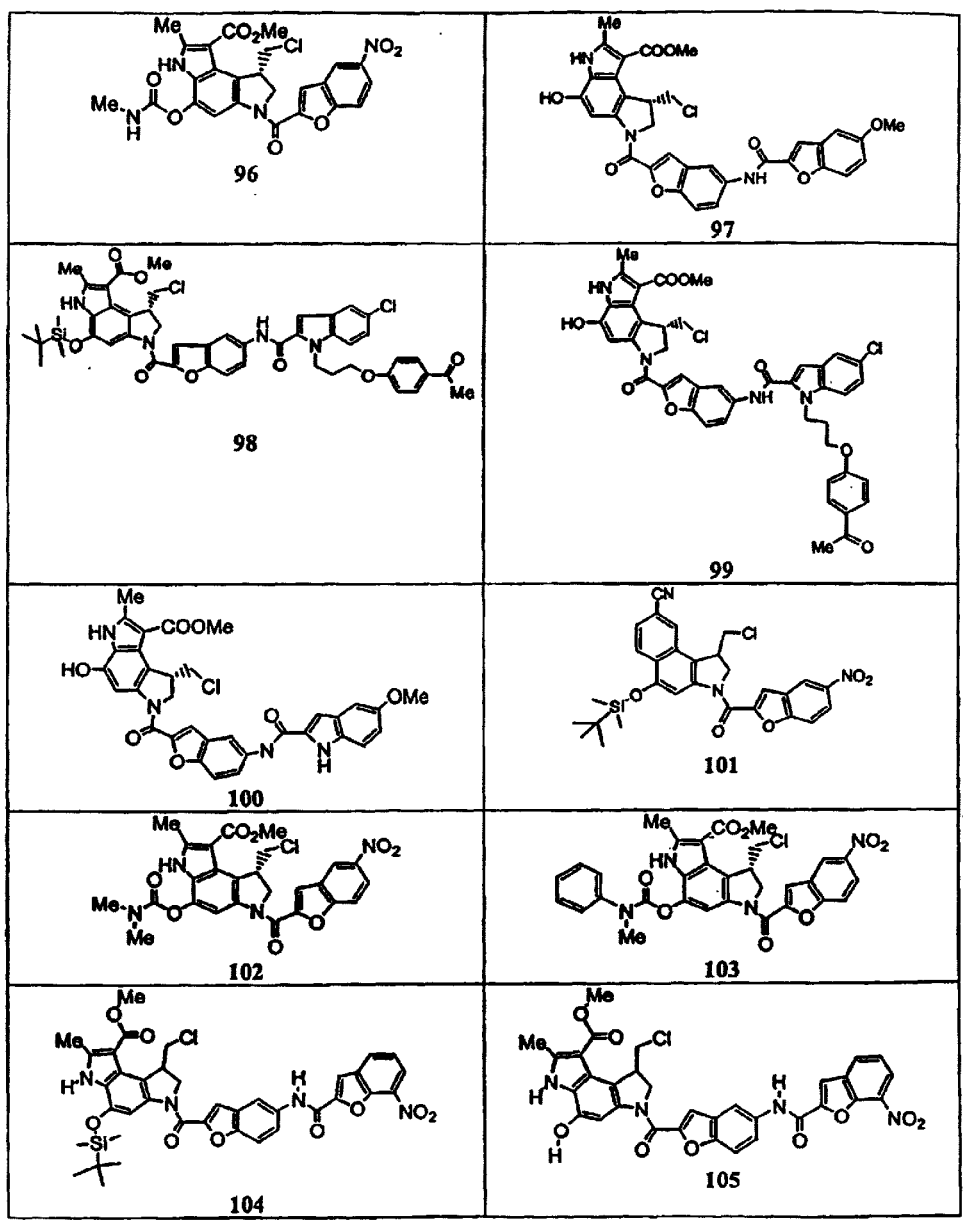
Figure 2.8

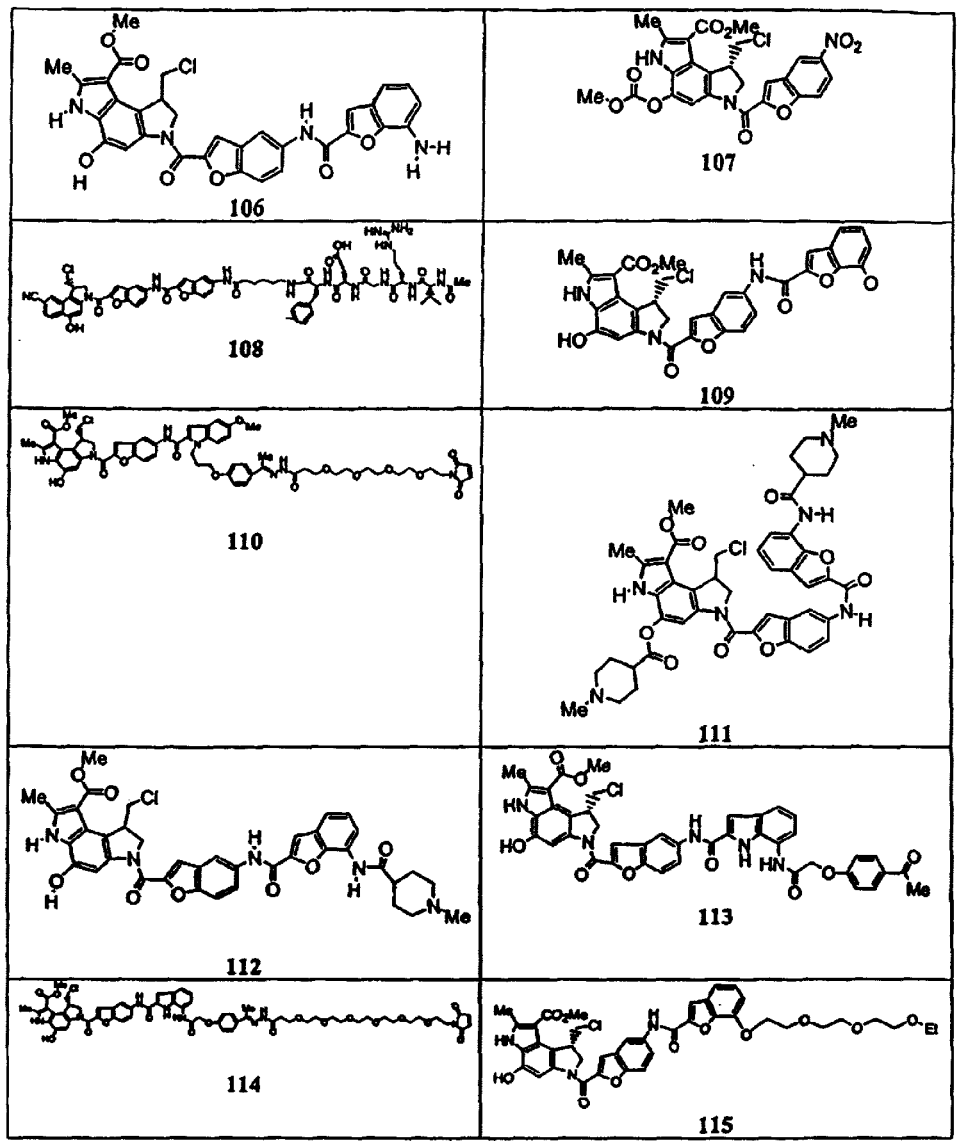
Figure 2.9

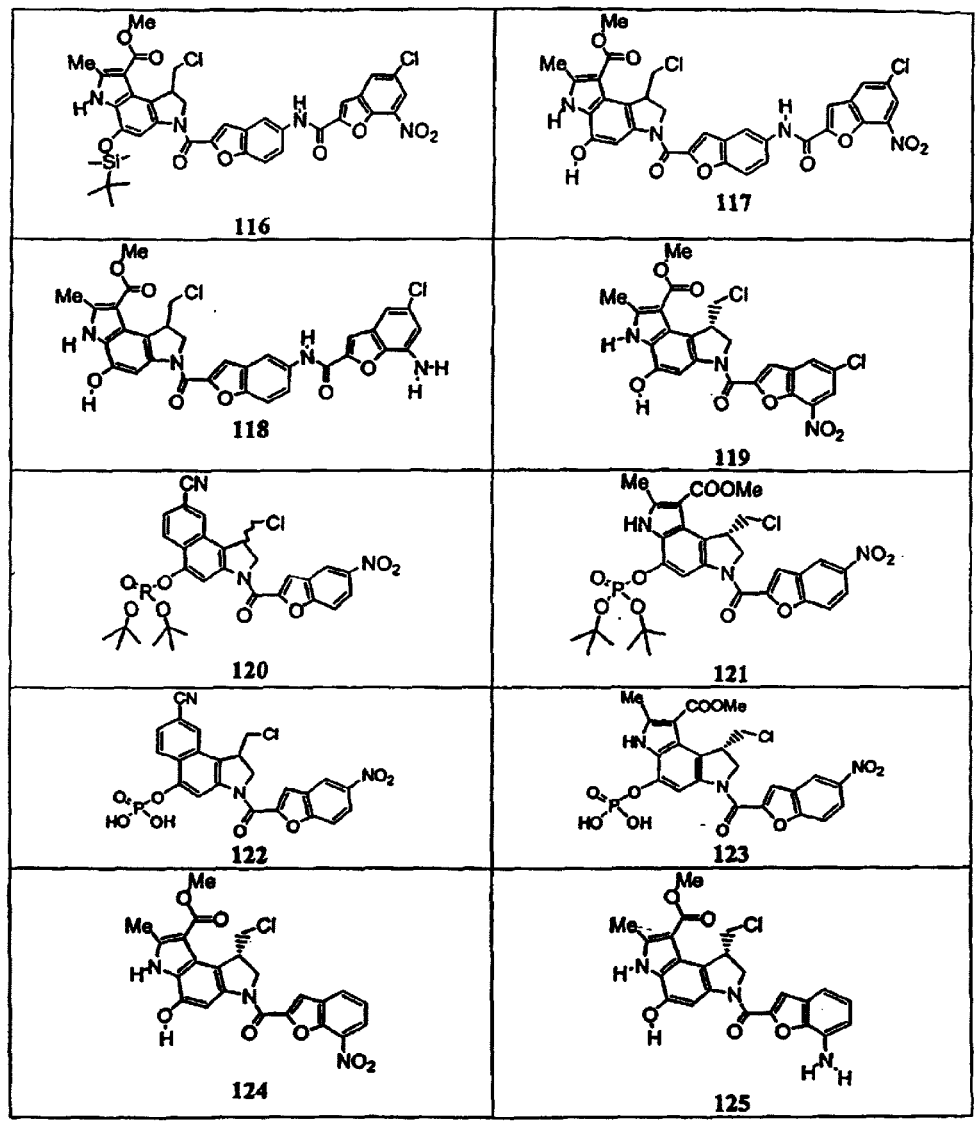
Figure 2.10

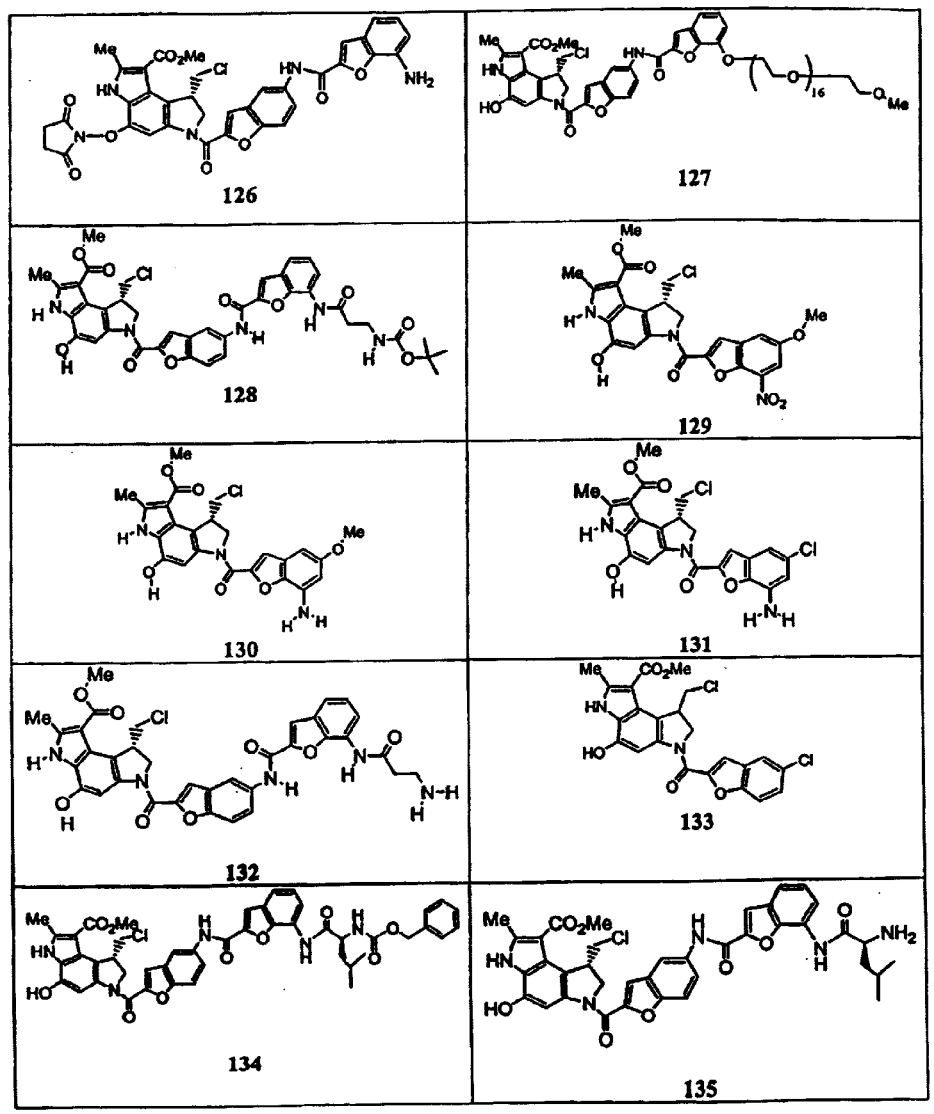
Figure 2.11

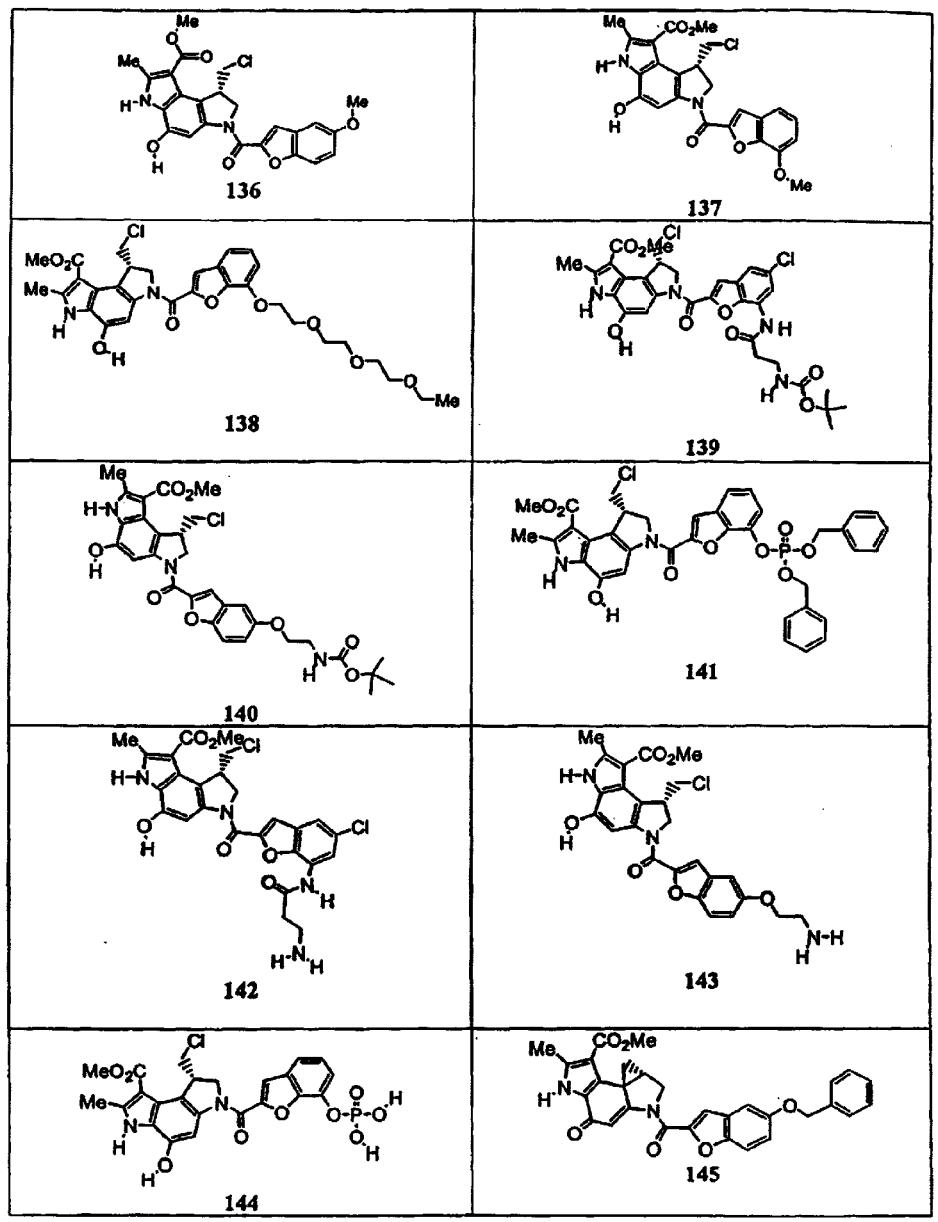
Figure 2.12

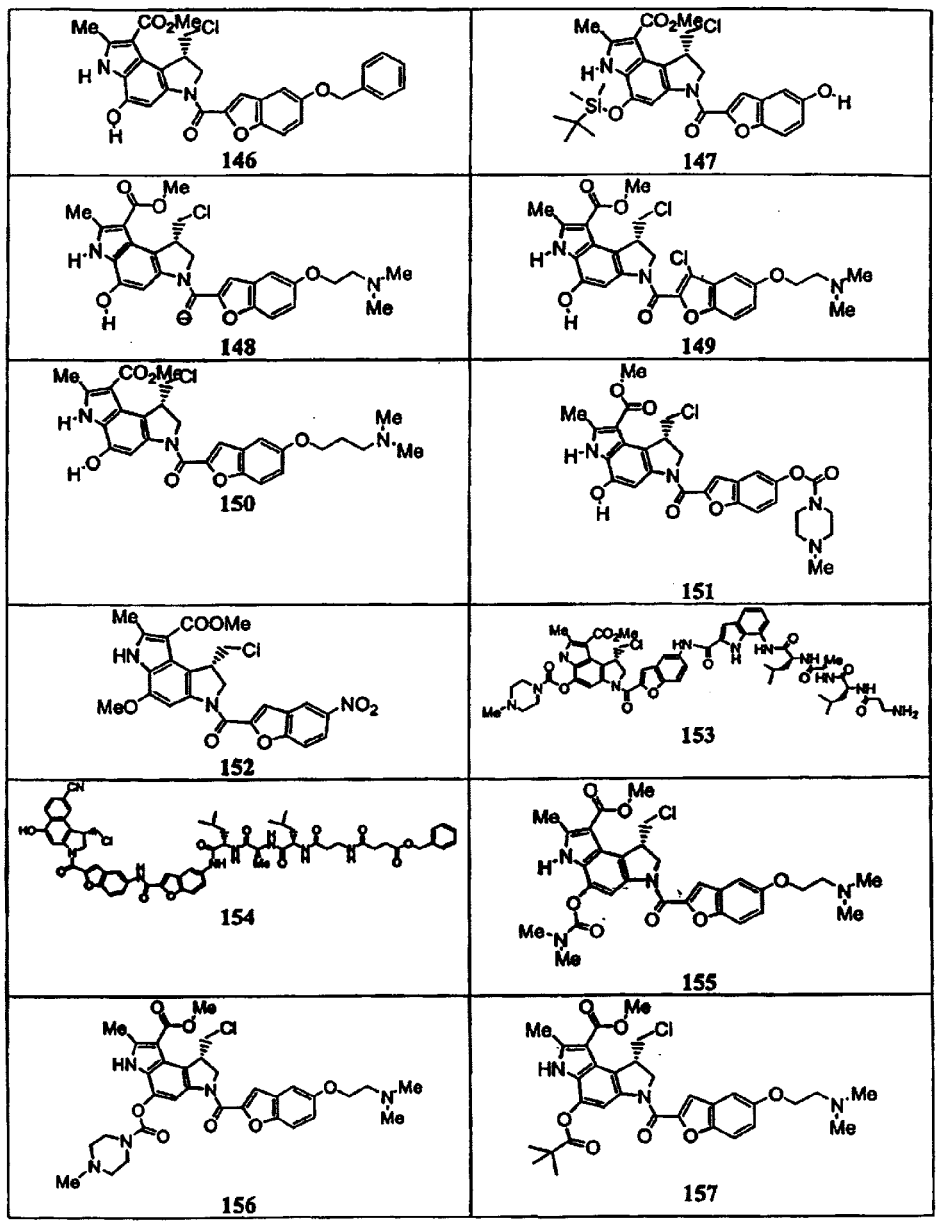
*Figure 2.13*

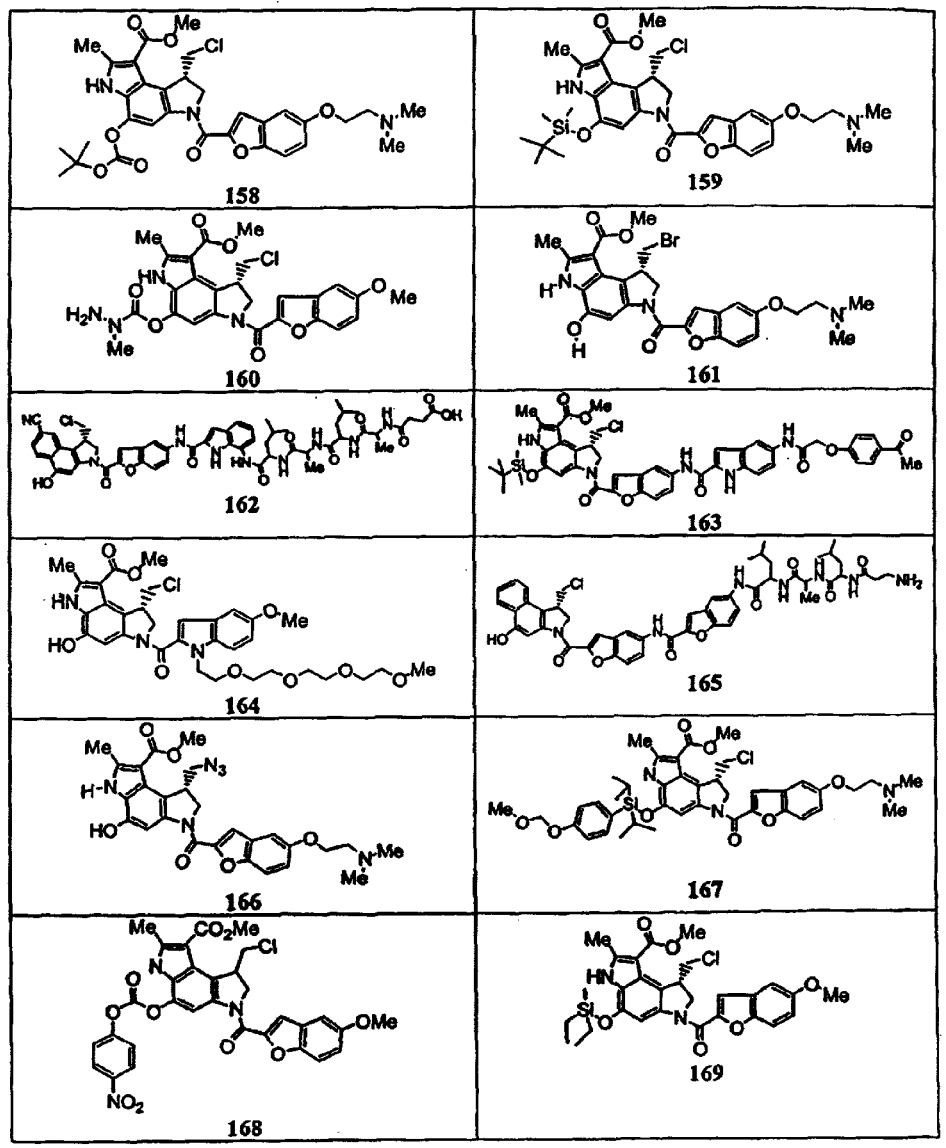
Figure 2.14

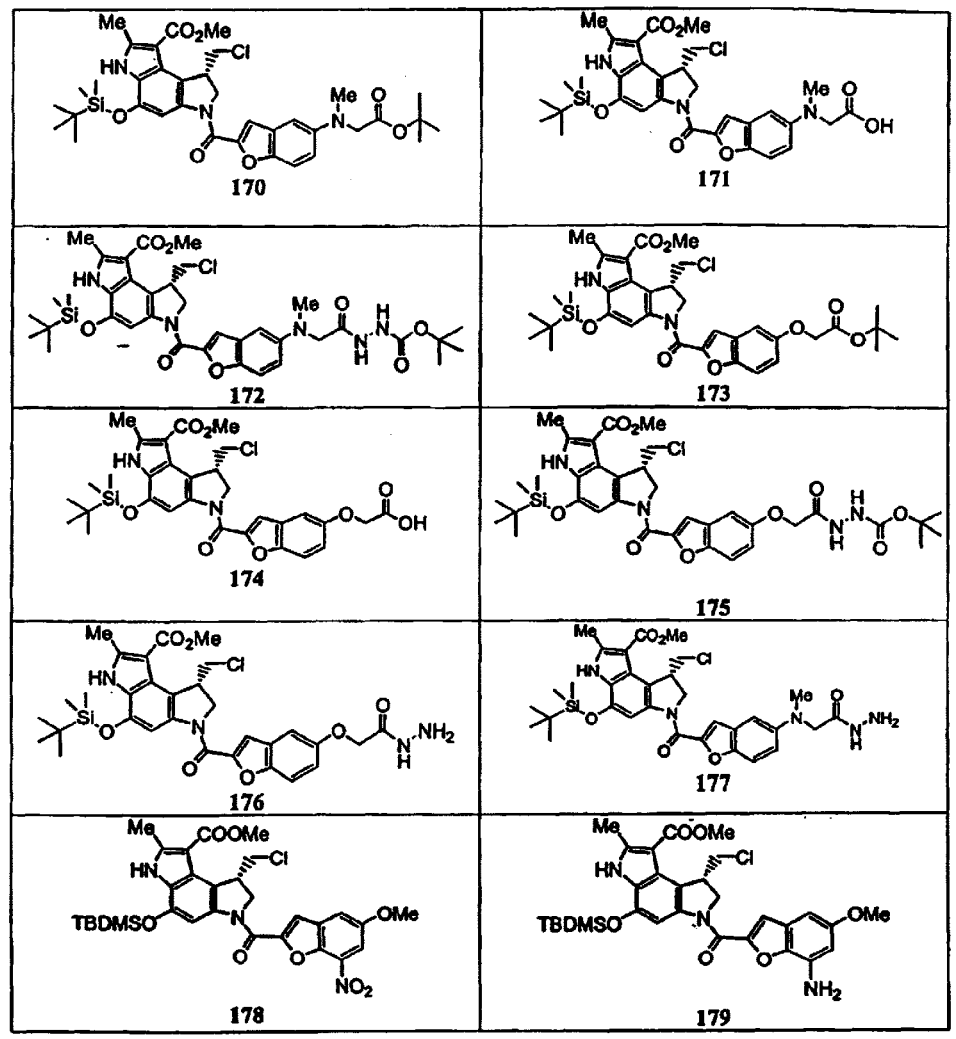
Figure 2.15

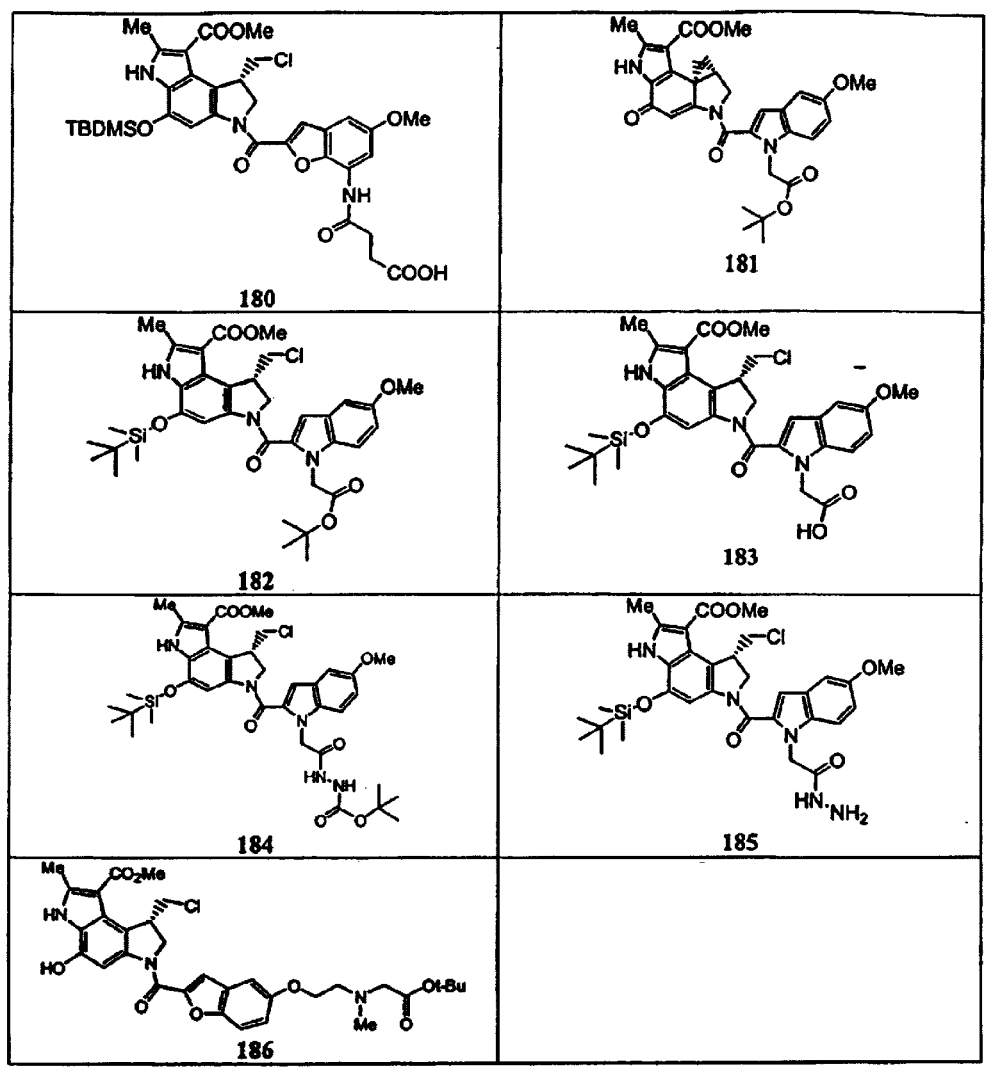
Figure 2.16

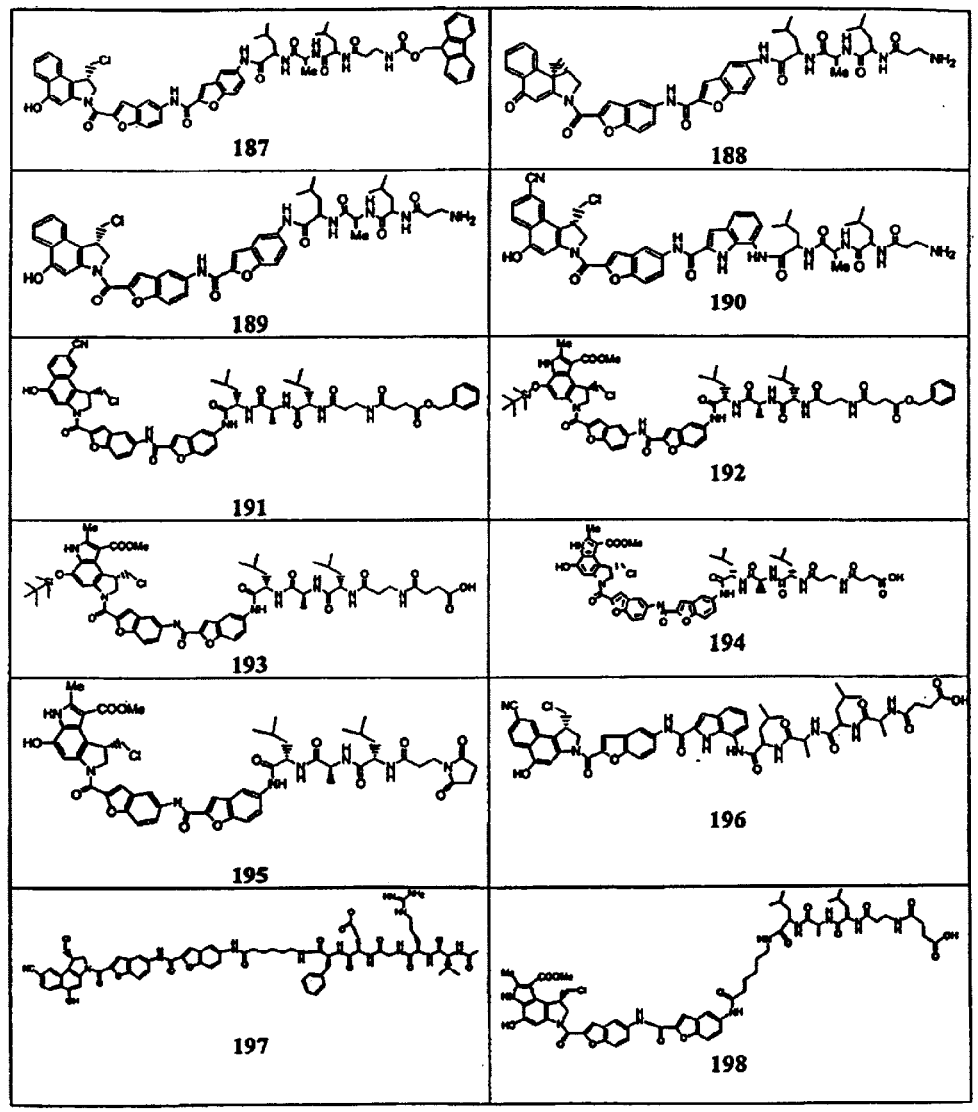
Figure 2.17

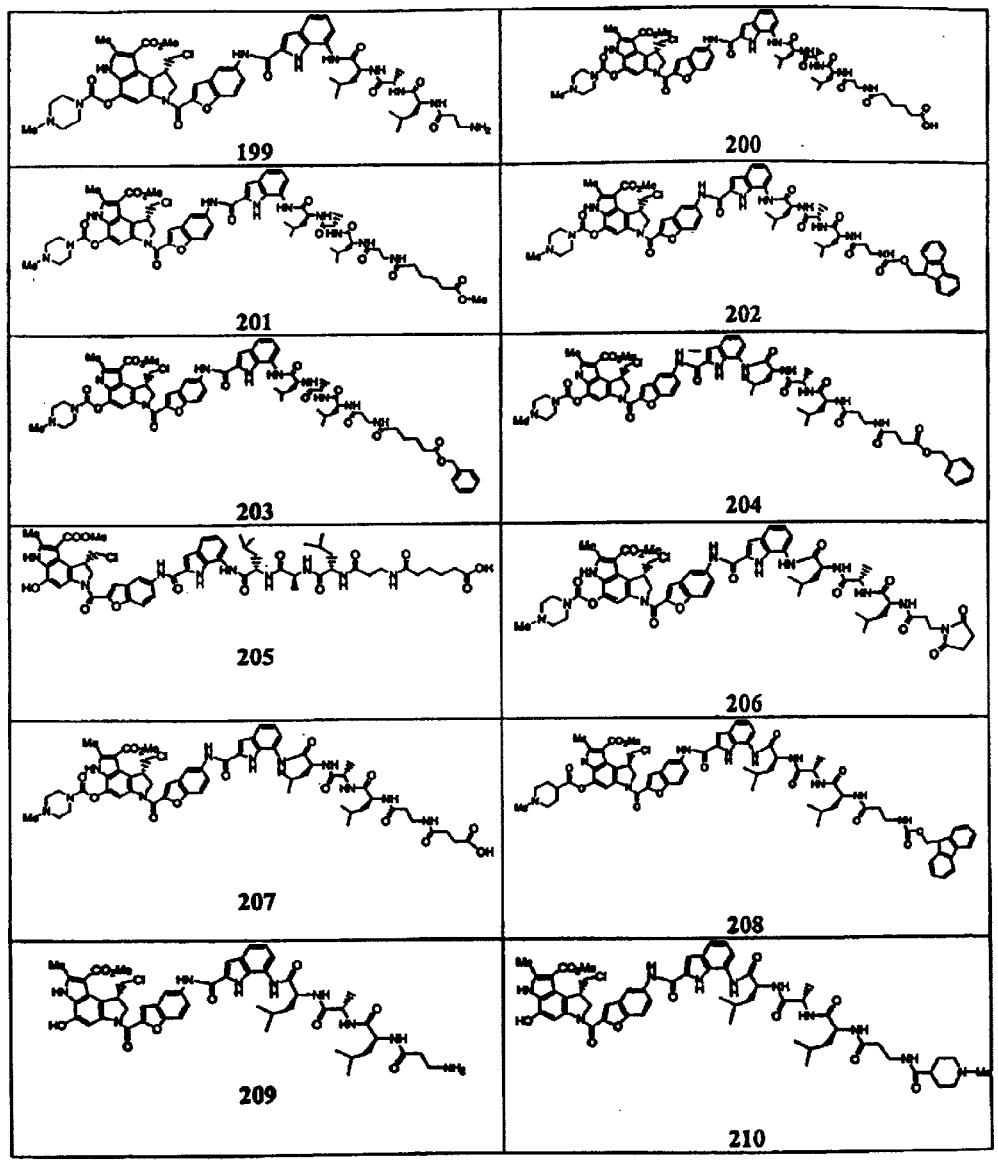
Figure 2.18

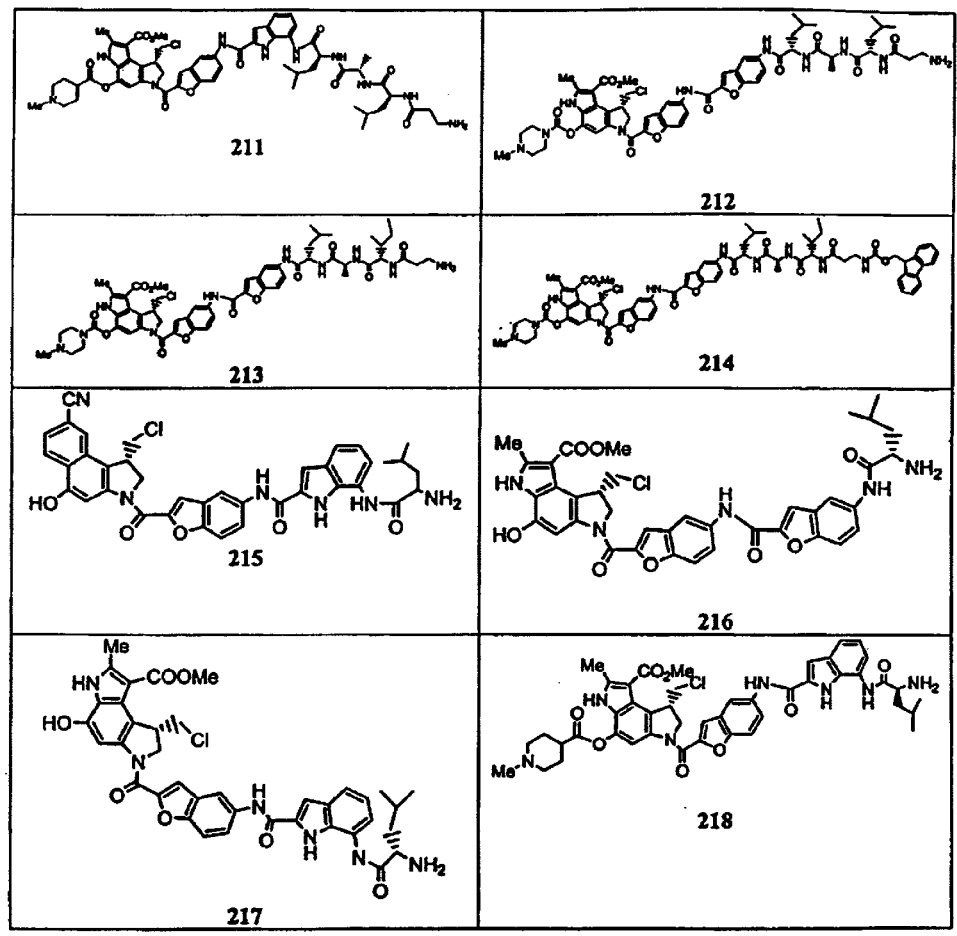
*Figure 2.19*

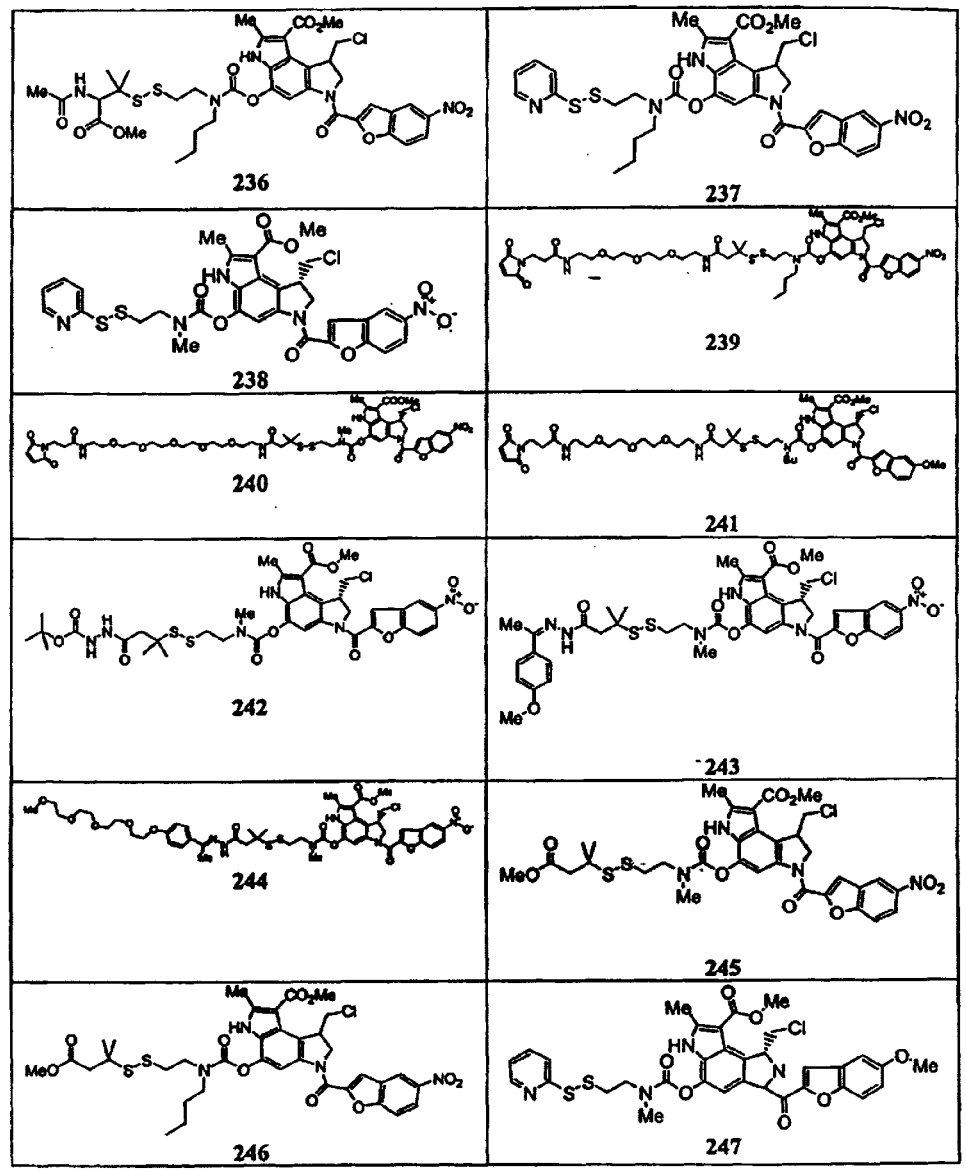
Figure 3.1

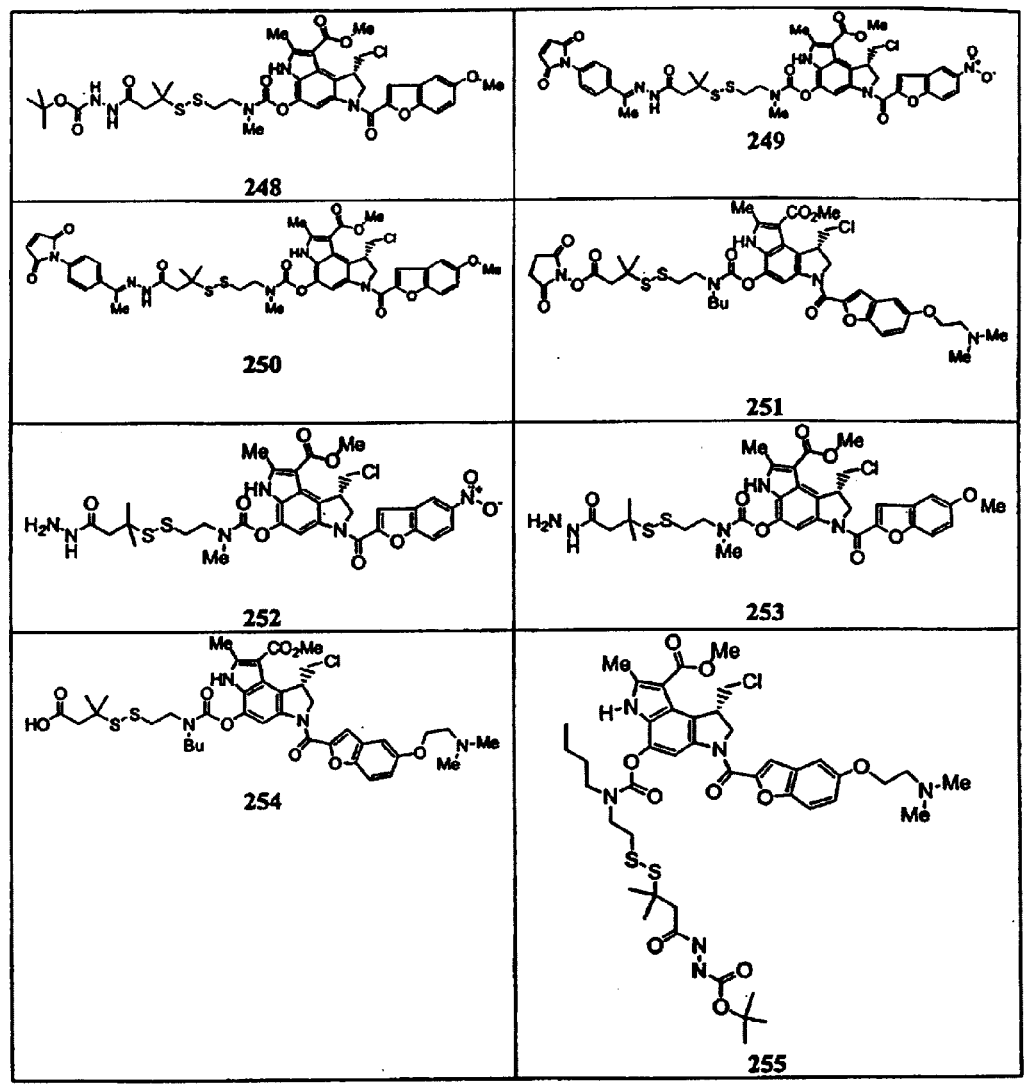
Figure 3.2

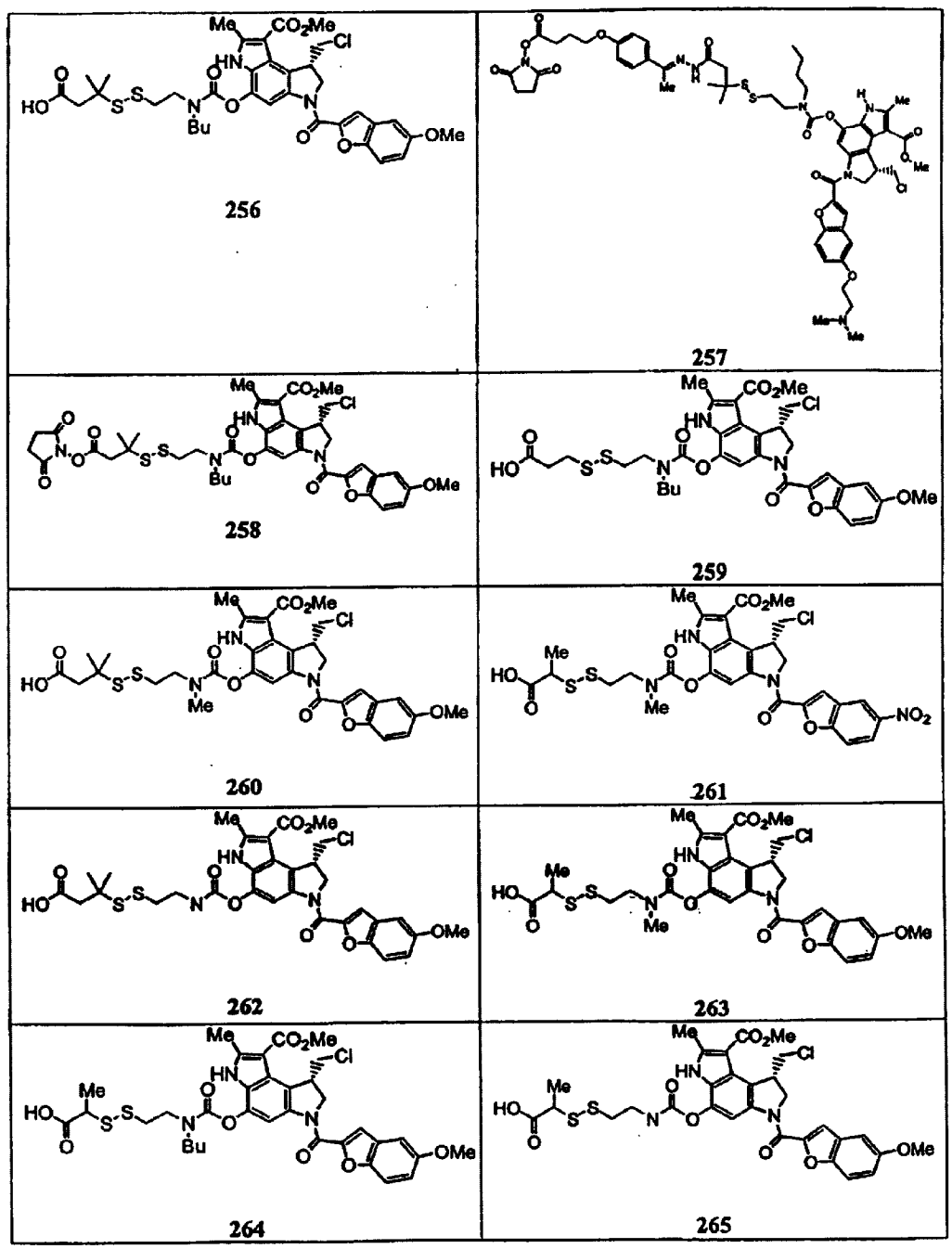
*Figure 3.3*

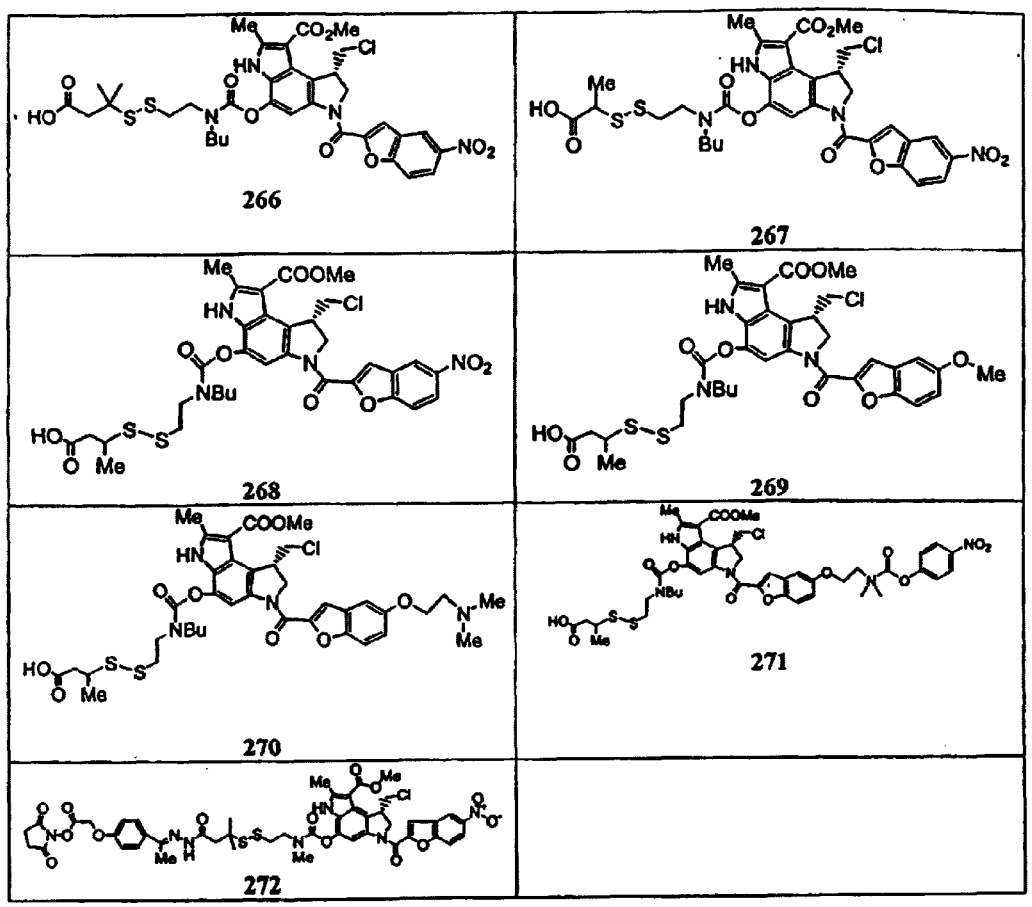
Figure 3.4

DISULFIDE PRODRUGS AND LINKERS AND STABILIZERS USEFUL THEREFOR

CROSS-REFERENCES TO RELATED APPLICATIONS

The present application is a non-provisional filing of U.S. Provisional Patent Application Nos. 60/295,196, filed May 31, 2001, 60/295,259, filed May 31, 2001, 60/295,342, filed May 31, 2001, and 60/304,908, filed Jul. 11, 2001. The disclosure of each of the provisional applications is incorporated herein by reference in its entirety for all purposes.

BACKGROUND OF THE INVENTION

Many therapeutic agents, particularly those that are especially effective in cancer chemotherapy, often exhibit acute toxicity in vivo, especially bone marrow and mucosal toxicity, as well as chronic cardiac and neurological toxicity. Such high toxicity can limit their applications. Development of more and safer specific therapeutic agents, particularly antitumor agents, is desirable for greater effectiveness against tumor cells and a decrease in the number and severity of the side effects of these products (toxicity, destruction of non-tumor cells, etc.). Another difficulty with some existing therapeutic agents is their less than optimal stability in plasma. Addition of functional groups to stabilize these compounds resulted in a significant lowering of the activity. Accordingly, it is desirable to identify ways to stabilize compounds while maintaining acceptable therapeutic activity levels.

The search for more selective cytotoxic agents has been extremely active for many decades, the dose limiting toxicity (i.e. the undesirable activity of the cytotoxins on normal tissues) being one of the major causes of failures in cancer therapy. For example, CC-1065 and the duocarmycins are known to be extremely potent cytotoxins.

CC-1065 was first isolated from *Streptomyces zelensis* in 1981 by the Upjohn Company (Hanka et al., *J. Antibiot.* 31: 1211 (1978); Martin et al., *J. Antibiot.* 33: 902 (1980); Martin et al., *J. Antibiot.* 34: 1119 (1981)) and was found to have potent antitumor and antimicrobial activity both in vitro and in experimental animals (Li et al., *Cancer Res.* 42: 999 (1982)). CC-1065 binds to double-stranded B-DNA within the minor groove (Swenson et al., *Cancer Res.* 42: 2821 (1982)) with the sequence preference of 5'-d(A/GNTTA)-3' and 5'-d(AAAAA)-3' and alkylates the N3 position of the 3'-adenine by its CPI left-hand unit present in the molecule (Hurley et al., *Science* 226: 843 (1984)). Despite its potent and broad antitumor activity, CC-1065 cannot be used in humans because it causes delayed death in experimental animals.

Many analogues and derivatives of CC-1065 and the duocarymycins are known in the art. The research into the structure, synthesis and properties of many of the compounds has been reviewed. See, for example, Boger et al., *Angew. Chem. Int. Ed. Engl.* 35: 1438 (1996); and Boger et al., *Chem. Rev.* 97: 787 (1997).

A group at Kyowa Hakko Kogya Co., Ltd. has prepared a number of CC-1065 derivatives. See, for example, U.S. Pat. Nos. 5,101,038; 5,641,780; 5,187,186; 5,070,092; 5,703,080; 5,070,092; 5,641,780; 5,101,038; and 5,084,468; and published PCT application, WO 96/10405 and published European application 0 537 575 A1. None of the patents or applications disclose the strategy of enhancing the stability of the cytotoxins by forming cleaveable prodrugs.

The Upjohn Company (Pharmacia Upjohn) has also been active in preparing derivatives of CC-1065. See, for example, U.S. Pat. Nos. 5,739,350; 4,978,757, 5,332,837 and 4,912,227. The issued U.S. patents do not disclose or suggest that a prodrug strategy would be useful to improve the in vivo stability or reduce the toxicity of the compounds disclosed in the patents.

Research has also focused on the development of new therapeutic agents which are in the form of prodrugs, compounds that are capable of being converted to drugs (active therapeutic compounds) in vivo by certain chemical or enzymatic modifications of their structure. For purposes of reducing toxicity, this conversion is preferably confined to the site of action or target tissue rather than the circulatory system or non-target tissue. However, even prodrugs are problematic as many are characterized by a low stability in blood and serum, due to the presence of enzymes that degrade or activate the prodrugs before the prodrugs reach the desired sites within the patient's body.

Therefore, in spite of the advances in the art, there continues to be a need for the development of improved therapeutic agents for the treatment of mammals and humans in particular, more specifically cytotoxins that exhibit high specificity of action, reduced toxicity, and improved stability in blood relative to known compounds of similar structure. The instant invention addresses those needs.

SUMMARY OF THE INVENTION

The present invention relates to cytotoxins that are analogs of CC-1065 and the duocarmycins. The present invention also provides linker arms that are cleaved, for example, enzymatically or reductively in vivo, releasing an active drug moiety from the prodrug derivative that includes the linker arm. Furthermore, the invention includes conjugates between the linker arms and the cytotoxins of the invention, and conjugates between the linker arms, the cytotoxin and a targeting agent, such as an antibody or a peptide.

The invention also relates to groups useful for stabilizing therapeutic agents and markers. The stabilizing groups are selected to limit clearance and metabolism of the therapeutic agent or marker by enzymes that may be present in blood or non-target tissue and are further selected to limit transport of the agent or marker into the cells. The stabilizing groups serve to block degradation of the agent or marker and may also act in providing other physical characteristics of the agent or marker. The stabilizing group may also improve the agent or marker's stability during storage in either a formulated or non-formulated form.

In a first aspect, the invention provides a cytotoxic compound having a structure according to Formula I:

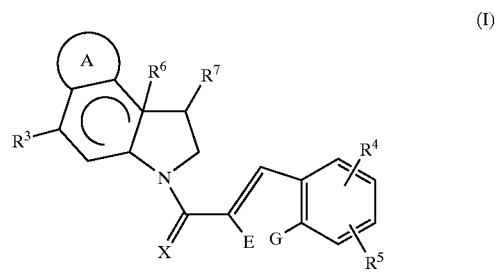

in which ring system A is a member selected from substituted or unsubstituted aryl, substituted or unsubstituted heteroaryl and substituted or unsubstituted heterocycloalkyl groups. The symbols E and G represent H, substituted or unsubstituted alkyl, substituted or unsubstituted heteroalkyl, a heteroatom, or a single bond. E and G are optionally joined to form a ring system selected from substituted or unsubstituted aryl, substituted or unsubstituted heteroaryl and substituted or unsubstituted heterocycloalkyl.

In an exemplary embodiment, ring system A is a substituted or unsubstituted phenyl ring. Ring system A is preferably substituted with one or more aryl group substituents as set forth in the definitions section herein. In one preferred embodiment, the phenyl ring is substituted with a CN moiety.

The curved line within the six-membered ring to which $R^3$ is attached indicates that the ring system may have one or more than one degree of unsaturation at any position within the ring, and it may indicate aromaticity.

The symbol X represents a member that is selected from O, S and $NR^{23}$. $R^{23}$ is a member selected from H, substituted or unsubstituted alkyl, substituted or unsubstituted heteroalkyl, and acyl.

The symbol $R^3$ represents a member selected from (=O), $SR^{11}$, $NHR^{11}$ and $OR^{11}$, in which $R^{11}$ is H, substituted or unsubstituted alkyl, substituted or unsubstituted heteroalkyl, acyl, $C(O)R^{12}$, $C(O)OR^{12}$, $C(O)NR^{12}R^{13}$, $C(O)OR^{12}$, $P(O)(OR^{12})_2$, $C(O)CHR^{12}R^{13}$, $C(O)OR^{12}$, $SR^{12}$ or $SiR^{12}R^{13}R^{14}$. The symbols $R^{12}$, $R^{13}$, and $R^{14}$ independently represent H, substituted or unsubstituted alkyl, substituted or unsubstituted heteroalkyl and substituted or unsubstituted aryl, wherein $R^{12}$ and $R^{13}$ together with the nitrogen atom to which they are attached are optionally joined to form a substituted or unsubstituted heterocycloalkyl ring system having from 4 to 6 members, optionally containing two or more heteroatoms.

$R^4$ and $R^5$ are members independently selected from H, substituted or unsubstituted alkyl, substituted or unsubstituted aryl, substituted or unsubstituted heteroaryl, substituted or unsubstituted heterocycloalkyl, substituted or unsubstituted arylalkyl, halogen, $NO_2$, $NR^{15}R^{16}$, $NC(O)R^{15}$, $OC(O)NR^{15}R^{16}$, $OC(O)OR^{15}$, $C(O)R^{15}$, $OP(O)OR^{15}OR^{16}$ and $OR^{15}$. $R^{15}$ and $R^{16}$ independently represent H, substituted or unsubstituted alkyl, substituted or unsubstituted heteroalkyl, substituted or unsubstituted aryl, substituted or unsubstituted heteroaryl, substituted or unsubstituted heterocycloalkyl, arylalkyl and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms.

$R^4$, $R^5$, $R^{11}$, $R^{12}$, $R^{13}$, $R^{15}$ and $R^{16}$ optionally contain one or more cleaveable groups within their structure. Exemplary cleaveable groups include, but are not limited to peptides, amino acids and disulfides.

$R^6$ is a single bond which is either present or absent. When $R^6$ is present, $R^6$ and $R^7$ are joined to form a cyclopropyl ring. $R^7$ is $CH_2$—$X^1$ or —$CH_2$—. When $R^7$ is —$CH_2$— it is a component of the cyclopropane ring. The symbol $X^1$ represents a leaving group. Those of skill will interpret combinations of $R^6$ and $R^7$ in a manner that does not violate the principles of chemical valence.

In another aspect, the invention provides cleaveable linker arms that include a group that is cleaved by an enzyme. The cleaveable linker generally imparts in vivo cleavability to the construct. Thus, the linker may include one or more groups that will cleave in vivo, e.g,. in the blood stream at a rate which is enhanced relative to that of constructs which lack such groups. Also provided are conjugates of the linker arms with therapeutic and diagnostic agents. The linkers are useful to form prodrug analogs of therapeutic agents and to reversibly link a therapeutic or diagnostic agent to a targeting agent, a detectable label, or a solid support. The linkers may be incorporated into complexes that include the cytotoxins of the invention. The linkers have the general formula set forth in Formula II:

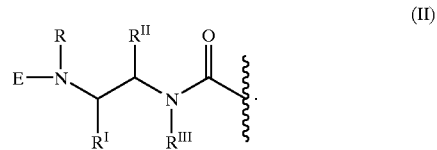

(II)

In the formula above, the symbol E represents an enzymatically cleaveable moiety (e.g,. peptide, ester, etc.). The symbols R, $R^I$, $R^{II}$ and $R^{III}$ represent members that include, for example, H, substituted or unsubstituted alkyl, substituted or unsubstituted heteroalkyl, poly(ethylene glycol), acyl, a targeting agent, a detectable label. In a presently preferred embodiment, the oxygen of the carboxyl moiety is tethered to a moiety that is a detectable label, a therapeutic moiety or a solid support.

In yet a further aspect, the invention provides a cleaveable linker arm that is based upon a disulfide moiety. Thus, there is provided a compound having a structure according to Formula III:

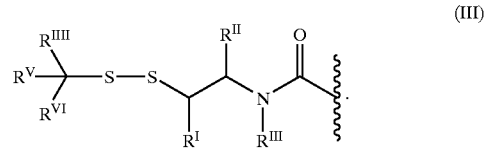

(III)

The identities of the radicals represented by the symbols R, $R^I$, $R^{II}$, $R^{III}$, $R^{IIII}$, $R^V$ and $R^{VI}$ are as described for R, $R^I$, $R^{II}$ and $R^{III}$ above.

Other aspects, advantages and objects of the invention will be apparent from review of the detailed description below.

BRIEF DESCRIPTION OF THE DRAWINGS

FIG. 1 sets forth exemplary cleaveable urethane linkers of the invention conjugated to a cytotoxin.

FIG. 2 sets forth exemplary cytotoxins of the invention.

FIG. 3 sets forth exemplary cleaveable disulfide linkers of the invention conjugated to a cytotoxin.

DETAILED DESCRIPTION OF THE INVENTION AND THE PREFERRED EMBODIMENTS

Abbreviations

As used herein, "Ala," refers to alanine.

"Boc," refers to t-butyloxycarbonyl.

"DDQ," refers to 2,3-dichloro-5,6-dicyano-1,4-benzoquinone.

As used herein, the symbol "E," represents an enzymatically cleaveable group.

"EDCI" is 1-(3-dimethylaminopropyl-3-ethylcarbodiimide.

As used herein, "FMOC," refers to 9-fluorenylmethyloxycarbonyl.

"Leu" is leucine.

The symbol "PMB," refers to para-methoxybenzyl.

"TBAF," refers to tetrabutylammonium fluoride.

The abbreviation "TBSO," refers to t-butyldimethylsilyl ether.

"TFA," refers to trifluororoacetic acid.

The symbol "Q," refers to a therapeutic agent, diagnostic agent or detectable label.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses. The term "therapeutic agent" is intended to mean a compound that, when present in a therapeutically effective amount, produces a desired therapeutic effect on a mammal. For treating carcinomas, it is desirable that the therapeutic agent also be capable of entering the target cell.

The term "cytotoxin" is intended to mean a therapeutic agent having the desired effect of being cytotoxic to cancer cells. Exemplary cytotoxins include, by way of example and not limitation, combretastatins, duocarmycins, the CC-1065 anti-tumor antibiotics, anthracyclines, and related compounds. Other cytotoxins include mycotoxins, ricin and its analgoues, calicheamycins, doxirubicin and maytansinoids.

The term "marker" is intended to mean a compound useful in the characterization of tumors or other medical condition, for example, diagnosis, progression of a tumor, and assay of the factors secreted by tumor cells. Markers are considered a subset of "diagnostic agents."

The term "targeting group" is intended to mean a moiety that is (1) able to direct the entity to which it is attached (e.g., therapeutic agent or marker) to a target cell, for example to a specific type of tumor cell or (2) is preferentially activated at a target tissue, for example a tumor. The targeting group can be a small molecule, which is intended to include both non-peptides and peptides. The targeting group can also be a macromolecule, which includes saccharides, lectins, receptors, ligand for receptors, proteins such as BSA, antibodies, and so forth.

The term "cleaveable group" is intended to mean a moiety that is unstable in vivo. Preferably the "cleaveable group" allows for activation of the marker or therapeutic agent by cleaving the marker or agent from the rest of the conjugate. Operatively defined, the linker is preferably cleaved in vivo by the biological environment. The cleavage may come from any process without limitation, e.g., enzymatic, reductive, pH, etc. Preferably, the cleaveable group is selected so that activation occurs at the desired site of action, which can be a site in or near the target cells (e.g., carcinoma cells) or tissues such as at the site of therapeutic action or marker activity. Such cleavage is enzymatic and exemplary enzymatically cleaveable groups include natural amino acids or peptide sequences that end with a natural amino acid, and are attached at their carboxyl terminus to the linker. While the degree of cleavage rate enhancement is not critical to the invention, preferred examples of cleaveable linkers are those in which at least about 10% of the cleaveable groups are cleaved in the blood stream within 24 hours of administration, most preferably at least about 35%. Preferred cleaveable groups are peptide bonds, ester linkages, and disulfide linkages.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. These terms also encompass the term "antibody."

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but functions in a manner similar to a naturally occurring amino acid. The term "unnatural amino acid" is intended to represent the "D" stereochemical form of the twenty naturally occurring amino acids described above. It is further understood that the term unnatural amino acid includes homologues of the natural amino acids, and synthetically modified forms of the natural amino acids. The synthetically modified forms include, but are not limited to, amino acids having alkylene chains shortened or lengthened by up to two carbon atoms, amino acids comprising optionally substituted aryl groups, and amino acids comprised halogenated groups, preferably halogenated alkyl and aryl groups. When attached to a linker or conjugate of the invention, the amino acid is in the form of an "amino acid side chain", where the carboxylic acid group of the amino acid has been replaced with a keto (C(O)) group. Thus, for example, an alanine side chain is —C(O)—CH(NH$_2$)—CH$_3$, and so forth.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions)

and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605–2608 (1985); Rossolini et al., *Mol. Cell. Probes* 8: 91–98 (1994)). The term nucleic acid is used interchangeably with gene, cDNA, mRNA, oligonucleotide, and polynucleotide.

The symbol ⁓, whether utilized as a bond or displayed perpendicular to a bond indicates the point at which the displayed moiety is attached to the remainder of the molecule, solid support, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen, carbon and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). The terms "heteroalkyl" and "heteroalkylene" encompass poly(ethylene glycol) and its derivatives (see, for example, Shearwater Polymers Catalog, 2001). Still further, for alkylene and heteroalkylene linking groups, no orientation of the linking group is implied by the direction in which the formula of the linking group is written. For example, the formula —C(O)$_2$R'-represents both —C(O)$_2$R'— and —R'C(O)$_2$—.

The term "lower" in combination with the terms "alkyl" or "heteroalkyl" refers to a moiety having from 1 to 6 carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of substituted or unsubstituted "alkyl" and substituted or unsubstituted "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The heteroatoms and carbon atoms of the cyclic structures are optionally oxidized.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1–3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$–C$_4$)alkoxy, and fluoro(C$_1$–C$_4$)alkyl, in a number ranging from zero to the total number of open valences on the aromatic ring system; and where R', R", R'" and R"" are preferably independently selected from hydrogen, (C$_1$–C$_8$)alkyl and heteroalkyl, unsubstituted aryl and heteroaryl, (unsubstituted aryl)-(C$_1$–C$_4$)alkyl, and (unsubstituted aryl)oxy-(C$_1$–C$_4$)alkyl. When a compound of the invention includes more than one R group, for example, each of the R groups is independently selected as are each R', R", R'" and R"" groups when more than one of these groups is present.

Two of the aryl substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$–C$_6$)alkyl.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1–19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "attaching moiety" or "moiety for attaching a targeting group" refers to a moiety which allows for attachment of a targeting group to the linker. Typical attaching groups include, by way of illustration and not limitation, alkyl, aminoalkyl, aminocarbonylalkyl, carboxyalkyl, hydroxyalkyl, alkyl-maleimide, alkyl-N-hydroxylsuccinimide, poly(ethylene glycol)-maleimide and poly(ethylene glycol)-N-hydroxylsuccinimide, all of which may be further substituted. The linker can also have the attaching moiety be actually appended to the targeting group.

As used herein, the term "leaving group" refers to a portion of a substrate that is cleaved from the substrate in a reaction.

"Antibody" generally refers to a polypeptide comprising a framework region from an immunoglobulin or fragments thereof that specifically binds and recognizes an antigen. The recognized immunoglobulins include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region, thereby converting the F(ab)'2 dimer into an Fab' monomer. The Fab' monomer is essentially an Fab with part of the hinge region (see, FUNDAMENTAL IMMUNOLOGY (Paul ed., $3^{rd}$ ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in MONOCLONAL ANTIBODIES AND CANCER THERAPY, Alan R. Liss, Inc. (1985)).

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired.

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6: 511–519 (1976)). Alternative methods of immortalization include transformation with Epstein Barr Virus, oncogenes, or retroviruses, or other methods well known in the art.

In a still further preferred embodiment, the antibody is a human or humanized antibody. "Humanized" refers to a non-human polypeptide sequence that has been modified to minimize immunoreactivity in humans, typically by altering the amino acid sequence to mimic existing human sequences, without substantially altering the function of the polypeptide sequence (see, e.g., Jones et al., *Nature* 321: 522–525 (1986), and published UK patent application No. 8707252). A "human" antibody is composed entirely of polypeptide sequences from human antibody genes and can be obtained, for example, by phage display methods or from mice genetically altered to contain human immunoglobin genes.

"Solid support," as used herein refers to a material that is substantially insoluble in a selected solvent system, or which can be readily separated (e.g., by precipitation) from a selected solvent system in which it is soluble. Solid supports useful in practicing the present invention can include groups that are activated or capable of activation to allow selected species to be bound to the solid support. A solid support can also be a substrate, for example, a chip, wafer or well, onto which an individual, or more than one compound, of the invention is bound.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like (see, for example, Hermanson, BIOCONJUGATE TECHNIQUES, Academic press, San Diego, 1996). Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The compounds of the invention are prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809–816; and Heller, Acc. Chem. Res. 23: 128 (1990).

Cytotoxins

Many therapeutic agents, particularly those that are especially effective in cancer chemotherapy, often exhibit acute toxicity in vivo, especially bone marrow and mucosal toxicity, as well as chronic cardiac and neurological toxicity. Such high toxicity can limit their applications. Development of more and safer specific therapeutic agents, particularly antitumor agents, is desirable for greater effectiveness against tumor cells and a decrease in the number and severity of the side effects of these products (toxicity, destruction of non-tumor cells, etc.).

The search for more selective cytotoxic agents has been extremely active for many decades, the dose limiting toxicities (i.e. the undesirable activity of the cytotoxins on normal tissues) being one of the major causes of failures in cancer therapy. For example, CC-1065 and the duocarmycins are known to be extremely potent cytotoxins. Numerous attempts have been made to evaluate analogs of these compounds; however, most have been shown to exhibit undesirable toxicity at therapeutic doses. Accordingly, the goal has been to improve the specificity of anti-tumor agents for increased effectiveness against tumor cells, while decreasing adverse side effects, such as toxicity and the destruction of non-tumor cells.

Research has focused on the development of new therapeutic agents which are in the form of prodrugs, compounds that are capable of being converted to drugs (active therapeutic compounds) in vivo by certain chemical or enzymatic modifications of their structure. For purposes of reducing toxicity, this conversion is preferably confined to the site of action or target tissue rather than the circulatory system or non-target tissue. However, even prodrugs are problematic as many are characterized by a low stability in blood and serum, due to the presence of enzymes that degrade or activate the prodrugs before the prodrugs reach the desired sites within the patient's body.

Therefore, in spite of the advances in the art, there continues to be a need for the development of improved therapeutic agents for the treatment of mammals and humans in particular, more specifically cytotoxins and related prodrugs that exhibit high specificity of action, reduced toxicity, and improved stability in blood relative to known compounds of similar structure.

In a first aspect, the invention provides a cytotoxic compound having a structure according to Formula I:

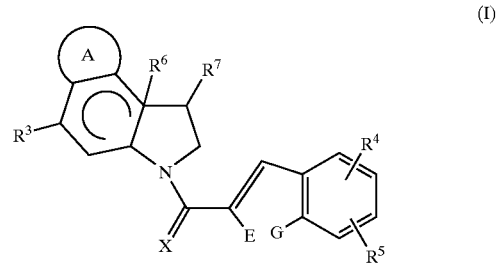

(I)

in which ring system A is a member selected from substituted or unsubstituted aryl substituted or unsubstituted heteroaryl and substituted or unsubstituted heterocycloalkyl groups. Exemplary ring systems include phenyl and pyrrole.

The symbols E and G represent H, substituted or unsubstituted alkyl, substituted or unsubstituted heteroalkyl, a heteroatom, or a single bond. E and G are optionally joined to form a ring system selected from substituted or unsubstituted aryl, substituted or unsubstituted heteroaryl and substituted or unsubstituted heterocycloalkyl.

The symbol X represents a member selected from O, S and NR$^{23}$. R$^{23}$ is a member selected from H, substituted or unsubstituted alkyl, substituted or unsubstituted heteroalkyl, and acyl.

The symbol R$^3$ represents a member selected from (=O), SR$^{11}$, NHR$^{11}$ and OR$^{11}$, in which R$^{11}$ is H, substituted or unsubstituted alkyl, substituted or unsubstituted heteroalkyl, acyl, C(O)R$^{12}$, C(O)OR$^{12}$, C(O)NR$^{12}$R$^{13}$, C(O)OR$^{12}$, P(O)

$(OR^{12})_2$, $C(O)CHR^{12}R^{13}$, $C(O)OR^{12}$, $SR^{12}$ or $SiR^{12}R^{13}R^{14}$. The symbols $R^{12}$, $R^{13}$, and $R^{14}$ independently represent H, substituted or unsubstituted alkyl, substituted or unsubstituted heteroalkyl and substituted or unsubstituted aryl, wherein $R^{12}$ and $R^{13}$ together with the nitrogen atom to which they are attached are optionally joined to form a substituted or unsubstituted heterocycloalkyl ring system having from 4 to 6 members, optionally containing two or more heteroatoms. One or more of $R^{12}$, $R^{13}$, or $R^{14}$ can include a cleaveable group within its structure.

$R^4$ and $R^5$ are members independently selected from H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$ and $OR^{15}$. $R^{15}$ and $R^{16}$ independently represent H, substituted or unsubstituted alkyl, substituted or unsubstituted heteroalkyl, substituted or unsubstituted aryl, substituted or unsubstituted heteroaryl, substituted or unsubstituted heterocycloalkyl and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms.

$R^4$, $R^5$, $R^{11}$, $R^{12}$, $R^{13}$, $R^{15}$ and $R^{16}$ optionally contain one or more cleaveable groups within their structure. Exemplary cleaveable groups include, but are not limited to peptides, amino acids and disulfides.

In another exemplary embodiment, the invention provides a compound according to Formula I, wherein at least one of $R^4$, $R^5$, $R^{11}$, $R^{12}$, $R^{13}$, $R^{15}$ and $R^{16}$ comprises:

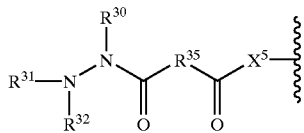

wherein $R^{30}$ is a member selected from H, substituted or unsubstituted alkyl and substituted or unsubstituted heteroalkyl. The symbols $R^{31}$ an $R^{32}$ independently represent H substituted or unsubstituted alkyl, substituted or unsubstituted heteroalkyl, substituted or unsubstituted aryl and substituted or unsubstituted heteroaryl, or $R^{31}$ and $R^{32}$ together are:

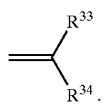

$R^{33}$ and $R^{34}$ independently represent H, substituted or unsubstituted alkyl, substituted or unsubstituted heteroalkyl, substituted or unsubstituted aryl or substituted or unsubstituted heteroaryl. The symbol $R^{35}$ represents substituted or unsubstituted alkyl, substituted or unsubstituted heteroalkyl or $NR^{36}$. $R^{36}$ is a member selected from H, substituted or unsubstituted alkyl and substituted or unsubstituted heteroalkyl. $X^5$ is O or $NR^{37}$, wherein $R^{37}$ is a member selected from H, substituted or unsubstituted alkyl and substituted or unsubstituted heteroalkyl. In yet a further embodiment, at least one of $R^{33}$ and $R^{34}$ is selected from $L^5X^6$, wherein the identity of "L" and "X" is generally as described herein.

In an exemplary embodiment, at least one of $R^{31}$, $R^{32}$, $R^{33}$ and $R^{34}$ in the structure above, is an aryl or heteroaryl moiety that is substituted with a moiety that includes a protected or unprotected reactive functional group, a targeting agent or a detectable label.

In a still further exemplary embodiment, at least one of $R^4$, $R^5$, $R^{11}$, $R^{12}$, $R^{13}$, $R^{15}$ and $R^{16}$ bears a reactive group appropriate for conjugating the compound according to Formula I to another molecule. In a further exemplary embodiment, $R^4$, $R^5$, $R^{11}$, $R^{12}$, $R^{13}$, $R^{15}$ and $R^{16}$ are independently selected from substituted alkyl and substituted heteroalkyl and have a reactive functional group at the free terminus of the alkyl or heteroalkyl moiety. One or more of $R^4$, $R^5$, $R^{11}$, $R^{12}$, $R^{13}$, $R^{15}$ and $R^{16}$ may be conjugated to another species, e.g, targeting agent, detectable label, solid support, etc.

As will be apparent from the discussion herein, when at least one of $R^{15}$ and $R^{16}$ is a reactive functional group, that group can be a component of a bond between the compound according to Formula I and another molecule. In an exemplary embodiment in which at least one of $R^{15}$ and $R^{16}$ is a linkage between the compound of Formula I and another species, at least one of $R^{15}$ and $R^{16}$ is a moiety that is cleaved by an enzyme.

In a further exemplary embodiment, at least one of $R^4$ and $R^5$ is:

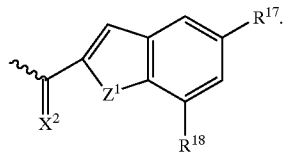

In the formula above, the symbols $X^2$ and $Z^1$ represent members independently selected from O, S and $NR^{23}$. The groups $R^{17}$ and $R^{18}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, halogen, $NO_2$, $NR^{19}R^{20}$, $NC(O)R^{19}$, $OC(O)NR^{19}$, $OC(O)OR^{19}$, $C(O)R^{19}$, $SR^{19}$ or $OR^{19}$.

The symbols $R^{19}$ and $R^{20}$ independently represent substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted peptidyl, wherein $R^{19}$ and $R^{20}$ together with the nitrogen atom to which they are attached are optionally joined to form a substituted or unsubstituted heterocycloalkyl ring system having from 4 to 6 members, optionally containing two or more heteroatoms, with the proviso that when $Z^1$ is NH, both $R^{17}$ and $R^{18}$ are not H, and $R^{17}$ is not $NH_2$. Throughout the present specification, the symbols $R^{19}$ and $R^{20}$ also encompass the groups set forth for $R^4$ and $R^5$. Thus, for example, it is within the scope of the present invention to provide compounds having two or more of the fused phenyl-heterocyclic ring systems set forth immediately above linked in series, or a fused ring in combination with a linker. Moreover, in those embodiments in which a linker is present, the linker may be present as an $R^4$ or $R^5$ substituent or as an $R^{17}$ or $R^{18}$ substituent.

$R^6$ is a single bond which is either present or absent. When $R^6$ is present, $R^6$ and $R^7$ are joined to form a cyclopropyl ring. $R^7$ is $CH_2$—$X^1$ or —$CH_2$—. When $R^7$ is —$CH_2$— it is a component of the cyclopropane ring. The symbol $X^1$ represents a leaving group. The combinations of $R^6$ and $R^7$ are interpreted in a manner that does not violate the principles of chemical valence.

The curved line within the six-membered ring indicates that the ring may have one or more degree of unsaturation, and it may be aromatic. Thus, ring structures such as those set forth below, and related structures, are within the scope of Formula I:

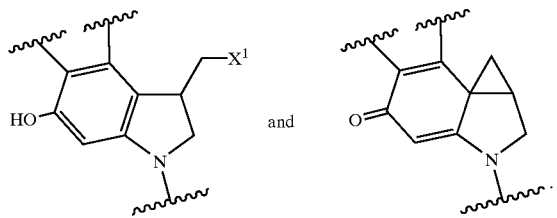

In an exemplary embodiment, ring system A is a substituted or unsubstituted phenyl ring. Ring system A is preferably substituted with one or more aryl group substituents as set forth in the definitions section herein. In one preferred embodiment, the phenyl ring is substituted with a CN moiety.

In another exemplary embodiment, the invention provides a compound having a structure according to Formula IV:

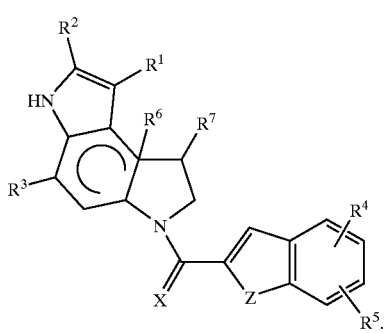

(IV)

In this embodiment, the identities of the radicals $R^3$, $R^4$, $R^5$, $R^6$, $R^7$ and X are substantially as described above. The symbol Z is a member independently selected from O, S and $NR^{23}$. The symbol $R^{23}$ represents a member selected from H, substituted or unsubstituted alkyl, substituted or unsubstituted heteroalkyl, and acyl. When both X and Z are $NR^{23}$, each $R^{23}$ is independently selected. The symbol $R^1$ represents H, substituted or unsubstituted lower alkyl, or $C(O)R^8$. $R^8$ is a member selected from $NR^9R^{10}$, $NR^9NHR^{10}$ and $OR^9$. $R^9$, and $R^{10}$ are independently selected from H, substituted or unsubstituted alkyl and substituted or unsubstituted heteroalkyl. The radical $R^2$ is H, or substituted or unsubstituted lower alkyl. It is generally preferred that when $R^2$ is substituted alkyl, it is other than perfluoroalkyl, e.g., $CF_3$.

As discussed above, $X^1$ may be a leaving group. Useful leaving groups include, but are not limited to, halides, azides, sulfonic esters (e.g., alkylsulfonyl, arylsulfonyl), oxonium ions, alkyl perchlorates, ammonioalkanesulfonate esters, alkylfluorosulfonates and fluorinated compounds (e.g., triflates, nonaflates, tresylates) and the like. The choice of these and other leaving groups appropriate for a particular set of reaction conditions is within the abilities of those of skill in the art (see, for example, March J, ADVANCED ORGANIC CHEMISTRY, 2nd Edition, John Wiley and Sons, 1992; Sandler SR, Karo W, ORGANIC FUNCTIONAL GROUP PREPARATIONS, 2nd Edition, Academic Press, Inc., 1983; and Wade LG, COMPENDIUM OF ORGANIC SYNTHETIC METHODS, John Wiley and Sons, 1980).

In an exemplary embodiment $R^1$ is an ester moiety, such as $CO_2CH_3$. In a further exemplary embodiment, $R^2$ is a lower alkyl group, which may be substituted or unsubstituted. A presently preferred lower alkyl group is $CH_3$. In a still further embodiment, $R^1$ is $CO_2CH_3$, and $R^2$ is $CH_3$.

In yet another exemplary embodiment, $R^4$ and $R^5$ are members independently selected from H, halogen, $NH_2$, $O(CH_2)_2N(Me)_2$ and $NO_2$. $R^4$ and $R^5$ are preferably not H or $OCH_3$.

In yet another exemplary embodiment, the invention provides compounds 25 having a structure according to Formulae V and VI:

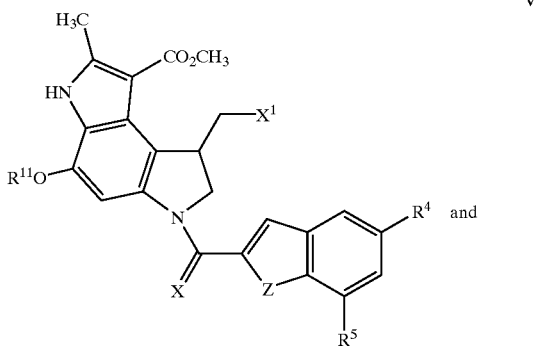

V

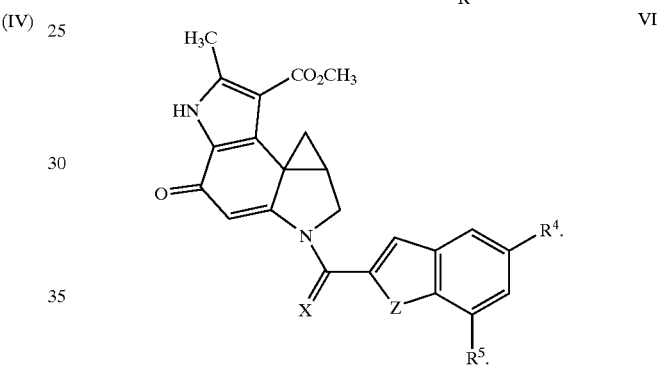

VI

In the Formulae above, X is preferably O; and Z is preferably O.

The compounds according to Formula I, may also include peptidyl linkers as a substituent. The linker may be located at any desired position on the compound. In an exemplary embodiment, at least one of $R^4$, $R^5$, $R^{11}$, $R^{12}$, $R^{13}$, $R^{15}$ and $R^{16}$ has a structure according to Formula VII:

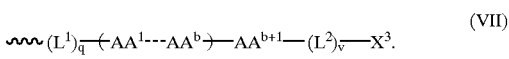

(VII)

In the discussion that follows, the linker according to Formula VII is exemplified as being $R^{11}$. The focus of the discussion is in the interest of clarity only, and it will be apparent to those of skill that the linker could be at any position of the compounds of the invention.

In Formula VII, the symbol $X^3$ represents a protected or unprotected reactive functional group, a detectable label or a targeting agent. The groups $L^1$ and $L^2$ are linkers selected from substituted or unsubstituted alkyl and substituted or unsubstituted heteroalkyl groups. Exemplary linkers, $L^1$ and $L^2$, comprises a poly(ethylene glycol) moiety. The linkers are either present or absent, thus, q and v are integers independently selected from 0 and 1. The symbols $AA^1$, $AA^b$ and $AA^{b+1}$ represent either natural and unnatural α-amino acids. The dashed line between $AA^1$ and $AA^b$ indicates that any number of amino acids may be intermediate to the two recited species. In an exemplary embodiment, the total number of amino acids within the parenthesis ("b") is from about 0 to about 20. In a further exemplary embodiment, "b" is an integer from about 1 to about 5.

An exemplary linker according to Formula VII is set forth in Formula VIII:

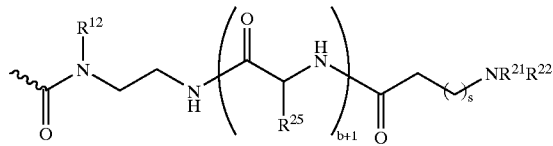

(VIII)

in which, the symbols $R^{21}$ and $R^{22}$ independently represent substituted or unsubstituted alkyl, substituted or unsubstituted heteroalkyl, substituted or unsubstituted aryl, substituted or unsubstituted heteroaryl, substituted or unsubstituted heterocycloalkyl, detectable labels and targeting agents. The groups $R^{12}$, and $R^{25}$ are independently selected from H, substituted or unsubstituted lower alkyl, an amino acid side chain, detectable labels, and targeting agents. The amino acid portion of the structure, represented by $AA^1$, $AA^b$ and $AA^{b+1}$ is substantially similar to that of Formula VII.

In another embodiment, the compounds according to Formula I include a linker having a structure according to Formula IX:

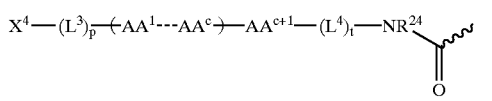

(IX)

wherein, the symbol $X^4$ represents a protected or unprotected reactive functional group, a detectable label or a targeting agents. The symbols $L^3$ and $L^4$ represents linkers that are substituted or unsubstituted alkyl, substituted or unsubstituted aryl, substituted or unsubstituted heteroaryl or a substituted or unsubstituted heteroalkyl group. The amino acid portion of the linker is substantially similar to that described for Formula VII. An exemplary linker includes within its framework a poly(ethylene glycol) analog. Each of the linkers is either present or absent, thus, p and t are integers independently selected from 0 and 1.

The linker according to Formula IX may be substituted onto any site of the molecule according to Formula I. In an exemplary embodiment, the linker according to Formula IX is a member selected from $R^4$, $R^5$, $R^{11}$, $R^{12}$, $R^{13}$, $R^{15}$ and $R^{16}$. Those of skill will appreciate that the linker may also be a component of one or more of $R^{17}$ or $R^{18}$, or similar sites in higher homologues of the compounds according to Formula I.

An exemplary linker according to Formula IX, is set forth in Formula X:

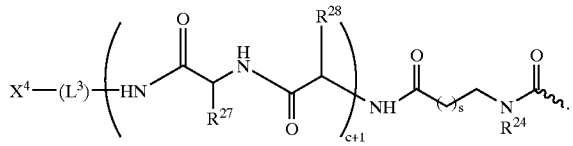

(X)

In Formula X, $R^{27}$ and $R^{28}$ are members independently selected from H, substituted or unsubstituted lower alkyl, amino acid side chains, detectable labels and targeting agents. The symbol "s" represents an integer that can be selected to provide a linker of any desired length. Presently preferred are linkers in which "s" is an integer from 0 to 6, more preferably between 1 and 5.

In yet another exemplary embodiment, the invention provides molecules according to Formula I, that are substituted with one or more linkers that include a cleaveable disulfide moiety within their structure such as that set forth in Formula XI:

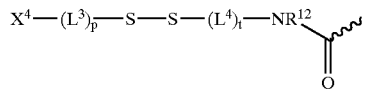

(XI)

in which $X^4$ is a member selected from protected reactive functional groups, unprotected reactive functional groups, detectable labels and targeting agents. $L^3$ is a linker selected from substituted or unsubstituted alkyl and substituted or unsubstituted heteroalkyl groups, substituted or unsubstituted aryl, substituted or unsubstituted heteroaryl, substituted or unsubstituted cycloalkyl. $L^4$ is a linker selected from substituted or unsubstituted alkyl and substituted or unsubstituted heteroalkyl groups, substituted or unsubstituted aryl, substituted or unsubstituted heteroaryl, substituted or unsubstituted cycloalkyl. The symbols p and t represent integers independently selected from 0 and 1.

In an exemplary embodiment according to Formula XI, the linker $L^4$ is a substituted or unsubstituted ethylene moiety.

The group, $X^4$ is a member selected from $R^{29}$, $COOR^{29}$, $C(O)NR^{29}$, and $C(O)NNR^{29}$ wherein $R^{29}$ is a member selected from substituted or unsubstituted alkyl, substituted or unsubstituted heteroalkyl and substituted or unsubstituted heteroaryl.

In yet another exemplary embodiment, $R^{29}$ is a member selected from H; OH; $NHNH_2$;

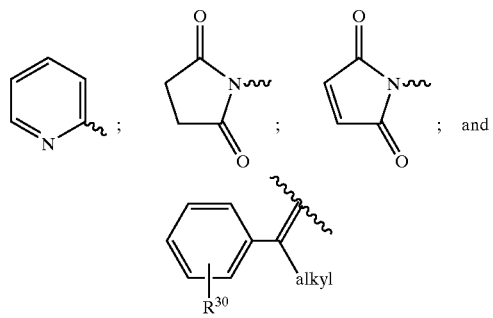

; and wherein $R^{30}$ represents substituted or unsubstituted alkyl terminated with a reactive functional group, substituted or unsubstituted heteroaryl terminated with a functional group and $-(L^3)_pX^4$, wherein each $L^3$, $X^4$ and p are independently selected.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like)

are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly (ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Exemplary cytotoxins of the invention are set forth in FIG. 2.

Prodrugs and Cleaveable Linkers

In addition to the linkers explicitly exemplified in the section above as being attached to cytotoxins of the invention, the present invention also provides cleaveable linker arms that are appropriate for attachment to essentially any molecular species. The linker arm aspect of the invention is exemplified herein by reference to their attachment to a therapeutic moiety. It will, however, be readily apparent to those of skill in the art that the linkers can be attached to diverse species including, but not limited to, diagnostic agents, analytical agents, biomolecules, targeting agents, detectable labels and the like.

In one aspect, the present invention relates to linkers that are useful to attach targeting groups to therapeutic agents and markers. In another aspect, the invention provides linkers that impart stability to compounds, reduce their in vivo toxicity, or otherwise favorably affect their pharmacokinetics, bioavailability and/or pharmacodynamics. It is generally preferred that in such embodiments, the linker is cleaved, releasing the active drug, once the drug is delivered to its site of action. Thus, in one embodiment of the invention, the linkers of the invention are traceless, such that once removed from the therapeutic agent or marker (such as during activation), no trace of the linker's presence remains.

In another embodiment of the invention, the linkers are characterized by their ability to be cleaved at a site in or near the target cell such as at the site of therapeutic action or marker activity. Such cleavage is preferably enzymatic in nature. This feature aids in reducing systemic activation of the therapeutic agent or marker, reducing toxicity and systemic side effects.

The linkers also serve to stabilize the therapeutic agent or marker against degradation while in circulation. This feature provides a significant benefit since such stabilization results in prolonging the circulation half-life of the attached agent or marker. The linker also serves to attenuate the activity of the attached agent or marker so that the conjugate is relatively benign while in circulation and has the desired effect, for example is toxic, after activation at the desired site of action. For therapeutic agent conjugates, this feature of the linker serves to improve the therapeutic index of the agent.

The stabilizing groups are preferably selected to limit clearance and metabolism of the therapeutic agent or marker by enzymes that may be present in blood or non-target tissue and are further selected to limit transport of the agent or marker into the cells. The stabilizing groups serve to block degradation of the agent or marker and may also act in providing other physical characteristics of the agent or marker. The stabilizing group may also improve the agent or marker's stability during storage in either a formulated or non-formulated form.

Ideally, the stabilizing group is useful to stabilize a therapeutic agent or marker if it serves to protect the agent or marker from degradation when tested by storage of the agent or marker in human blood at 37° C. for 2 hours and results in less than 20%, preferably less than 2%, cleavage of the agent or marker by the enzymes present in the human blood under the given assay conditions.

The present invention also relates to conjugates containing these linkers. More particularly, the invention relates to prodrugs that may be used for the treatment of disease, especially for cancer chemotherapy. Specifically, use of the linkers described herein provide for prodrugs that display a high specificity of action, a reduced toxicity, and an improved stability in blood relative to prodrugs of similar structure.

Thus, there is provided a linker may contain any of a variety of groups as part of its chain which will cleave in vivo, e.g,. in the blood stream at a rate which is enhanced relative to that of constructs which lack such groups. Also provided are conjugates of the linker arms with therapeutic and diagnostic agents. The linkers are useful to form prodrug analogs of therapeutic agents and to reversibly link a therapeutic or diagnostic agent to a targeting agent, a detectable label, or a solid support. The linkers may be incorporated into complexes that include the cytotoxins of the invention.

In one embodiment, the invention provides linkers that have the general formula set forth in Formula II:

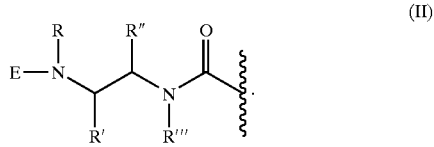

(II)

In the formula above, the symbol E represents an enzymatically cleaveable moiety (e.g,. peptide, disulfide, ester, etc.). The symbols R, R', R" and R'" represent members that include, for example, H, substituted or unsubstituted alkyl, substituted or unsubstituted heteroalkyl, poly (ethyleneglycol), acyl, a targeting agent, or a detectable label. In an exemplary embodiment, the carbonyl moiety is tethered to a moiety that is a detectable label, a therapeutic moiety or a solid support. The carbonyl moiety may be further attached to an oxygen, sulfur, nitrogen or carbon at the position where the fragment is truncated. In a further exemplary embodiment, the carbonyl moiety is a component of a urethane. The oxygen tethered to the carbonyl moiety is attached to a targeting agent, cytotoxin, solid support or the like.

Peptide-Based Linkers

In an exemplary embodiment, the enzymatically cleaveable group is an amino acid or peptide sequence ending with an amino acid attached at its carboxyl terminus to the remainder of the linker. Presently preferred amino acids or peptides are those that are tumor activated. The tumor-activated peptides are enzymatically cleaveable groups that are specifically cleaved at a tumor site. Specific peptides that are activated by specific enzymes associated with a selected tumor can be utilized; numerous such peptides are known in the art. Amino acids used in the linker can be either natural or unnatural amino acids. In a preferred embodiment, at least one amino acid in the sequence is a natural amino acid. An exemplary preparation of a linker that incorporates an amino acid moiety is set forth in Scheme 1, detailing the conjugation of Combrestatin to a linker of the invention.

Scheme 1

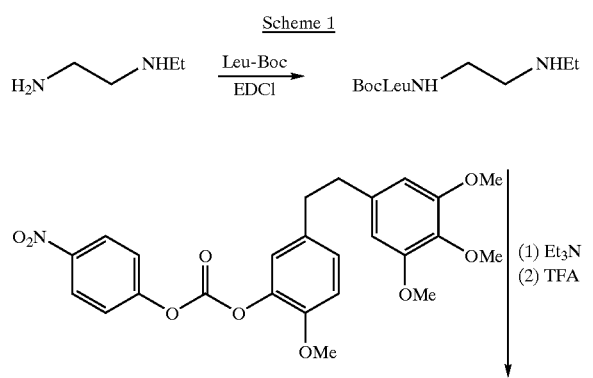

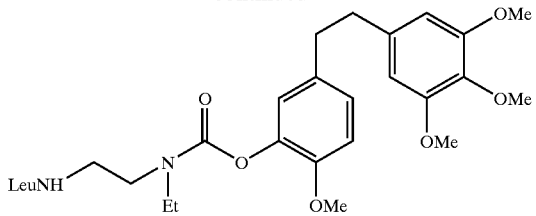

In Scheme 1, the EDCI mediated dehydrative coupling of a primary amine with t-Boc protected leucine provides the protected leucine-amine conjugate. The conjugate is coupled to Combrestatin through the p-nitrophenylcarbonate activated Combrestatin and the product is deprotected by cleavage of the t-Boc group with trifluoroacetic acid.

In another exemplary embodiment, the linker is a cyclic amino carbamate as set forth in Formula XII.

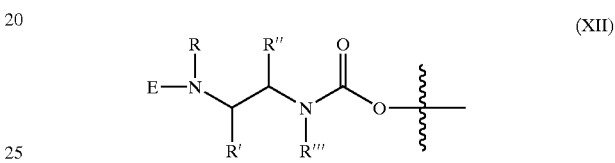

(XII)

The radicals in the formula above are substantially the same as those described in the context of the linear linker. Two of R, R', R" and R'" together with the atoms to which they are attached form a substituted or unsubstituted cycloalkyl, substituted or unsubstituted aryl, substituted or unsubstituted heteroaryl, or substituted or unsubstituted heterocycloalkyl moiety.

An exemplary synthetic route to a cyclic amino carbamate linker of the invention is set forth in Scheme 2.

Scheme 2

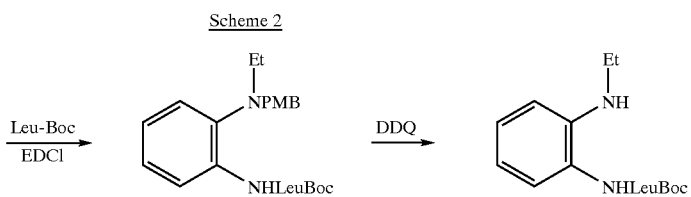

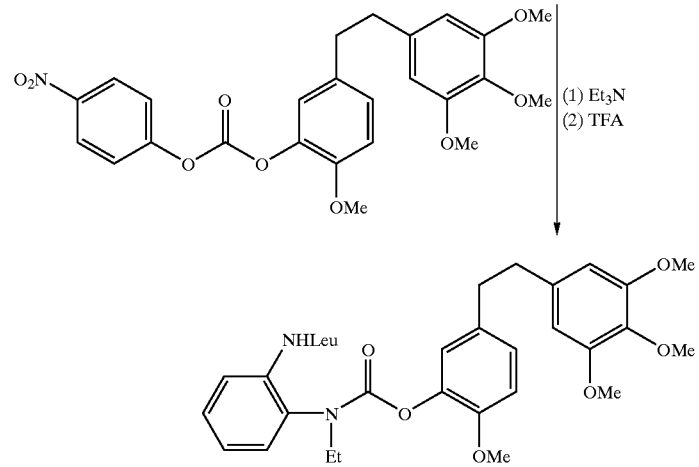

In Scheme 2, the p-methoxybenzyl protected phenyl diamine is coupled at the unprotected aniline nitrogen with t-Boc protected leucine using EDCI. The p-methoxybenzyl group is removed via the action of DDQ and the linker arm is coupled to Cobrestatin using p-nitrophenyl carbonate activated Combrestatin. The t-Boc group is removed with TFA, providing the Combrestatin-linker complex.

In yet another embodiment, there is provided an amino carbamate benzyl alcohol linker as set forth in Formula XIII below.

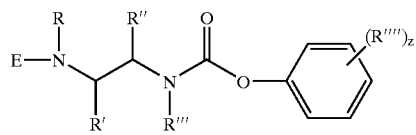

(XIII)

The identity of the radicals in the structure above is substantially similar to those set forth above. R"" represents any of the substituents for an aryl moiety discussed supra. When there is more than one R"" group, each of the R"" groups is independently selected, and z is an integer from 0 to 5.

An exemplary synthesis of an amino carbamate benzyl alcohol linker of the invention is set forth below in Scheme 3.

Scheme 3

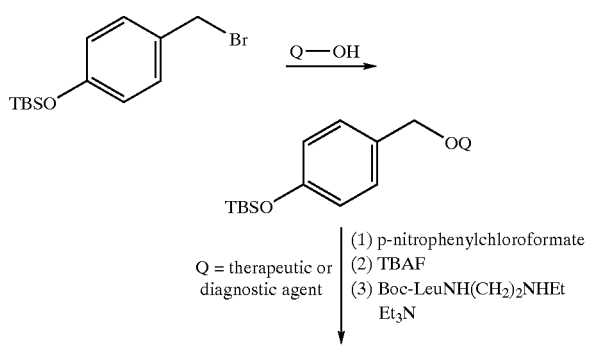

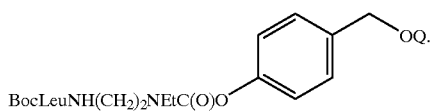

In Scheme 3, a t-butyldimethylsilyl O-protected phenyl alcohol with an activated benzylic position is coupled to a therapeutic or diagnostic agent. The conjugate is treated with tetrabutylammonium fluoride, removing the t-butyldimethylsilyl protecting group. The free OH group is converted to the active carbonate with p-nitrophenylchloroformate. The activated carbonate intermediate is used to couple protected BocLeuNH(CH$_2$)$_2$NHEt to the OH group, forming the linker-agent conjugate.

Peptide Linker-Duocarmycin Conjugates

CC-1065 and the duocarmycins are known to be extremely potent antitumor cytotoxins, which exhibit undesirable toxicity at therapeutic dosages. By attaching a tumor activated peptide to the cytotoxin, systemic toxicity is reduced and therapeutic index is increased. Thus, the present invention also provides prodrug conjugates of the duocarmycins, as well as conjugates between a duocarmycin and a targeting or other agent according to Formula I.

An exemplary synthetic scheme to a conjugate of the invention is set forth in Scheme 4. Additional synthetic routes are provided in the examples appended hereto.

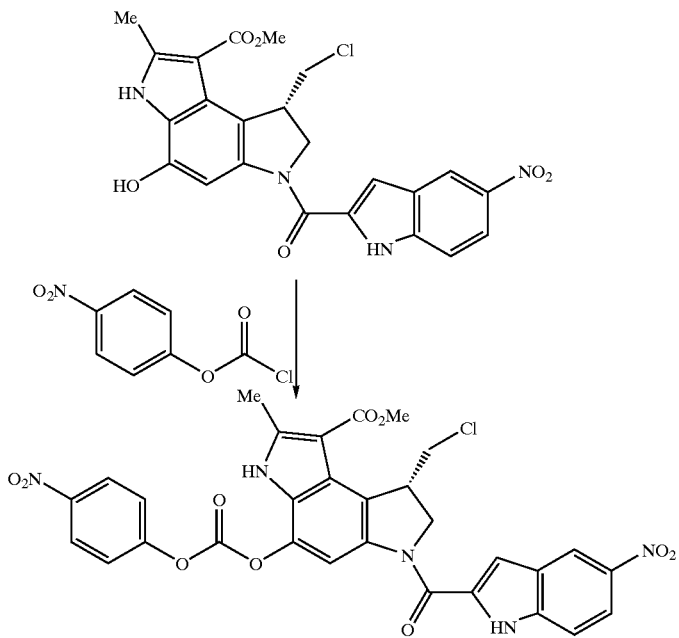

-continued

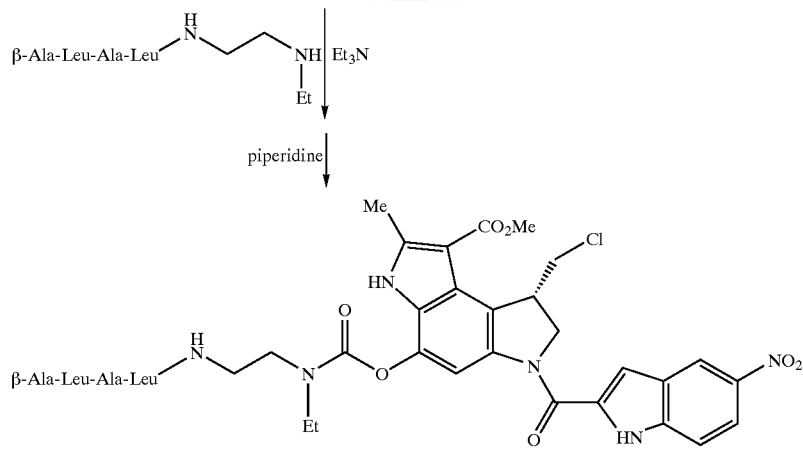

In Scheme 4, the cytotoxin is converted to the active carbonate with p-nitrophenylchloroformate and the activated derivative is contacted with the FMOC-protected tumor activated peptide, forming a conjugate. The conjugate is treated with piperidine, removing the FMOC group and providing the desired compound.

Many peptide sequences that are cleaved by enzymes in the serum, liver, gut, etc. are known in the art. An exemplary peptide sequence of the invention includes a peptide sequence that is cleaved by a protease. The focus of the discussion that follows on the use of a protease-sensitive sequence is for clarity of illustration and does not serve to limit the scope of the present invention.

When the enzyme that cleaves the peptide is a protease, the linker generally includes a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190–198 (1994).

Proteases have been implicated in cancer metastasis. Increased synthesis of the protease urokinase was correlated with an increased ability to metastasize in many cancers. Urokinase activates plasmin from plasminogen, which is ubiquitously located in the extracellular space and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. *Adv. Cancer. Res.,* 44: 139 (1985)). Thus, it is within the scope of the present invention to utilize as a linker a peptide sequence that is cleaved by urokinase.

The invention also provides the use of peptide sequences that are sensitive to cleavage by tryptases. Human mast cells express at least four distinct tryptases, designated α βI, βII, and βIII. These enzymes are not controlled by blood plasma proteinase inhibitors and only cleave a few physiological substrates in vitro. The tryptase family of serine proteases has been implicated in a variety of allergic and inflammatory diseases involving mast cells because of elevated tryptase levels found in biological fluids from patients with these disorders. However, the exact role of tryptase in the pathophysiology of disease remains to be delineated. The scope of biological functions and corresponding physiological consequences of tryptase are substantially defined by their substrate specificity.

Tryptase is a potent activator of pro-urokinase plasminogen activator (uPA), the zymogen form of a protease associated with tumor metastasis and invasion. Activation of the plasminogen cascade, resulting in the destruction of extracellular matrix for cellular extravasation and migration, maybe a function of tryptase activation of pro-urokinase plasminogen activator at the P4–P1 sequence of Pro-Arg-Phe-Lys (Stack, et al., *Journal of Biological Chemistry* 269(13): 9416–9419 (1994)). Vasoactive intestinal peptide, a neuropeptide that is implicated in the regulation of vascular permeability, is also cleaved by tryptase, primarily at the Thr-Arg-Leu-Arg sequence (Tam, et al., *Am. J. Respir. Cell Mol. Biol.* 3: 27–32 (1990)). The G-protein coupled receptor PAR-2 can be cleaved and activated by tryptase at the Ser-Lys-Gly-Arg sequence to drive fibroblast proliferation, whereas the thrombin activated receptor PAR-1 is inactivated by tryptase at the Pro-Asn-Asp-Lys sequence (Molino et al., *Journal of Biological Chemistry* 272(7): 4043–4049 (1997)). Taken together, this evidence suggests a central role for tryptase in tissue remodeling as a consequence of disease. This is consistent with the profound changes observed in several mast cell-mediated disorders. One hallmark of chronic asthma and other long-term respiratory diseases is fibrosis and thickening of the underlying tissues that could be the result of tryptase activation of its physiological targets. Similarly, a series of reports have shown angiogenesis to be associated with mast cell density, tryptase activity and poor prognosis in a variety of cancers (Coussens et al., *Genes and Development* 13(11): 1382–97 (1999)); Takanami et al., *Cancer* 88(12): 2686–92 (2000); Toth-Jakatics et al., *Human Pathology* 31(8): 955–960 (2000); Ribatti et al., *International Journal of Cancer* 85(2): 171–5 (2000)).

Methods are known in the art for evaluating whether a particular protease cleaves a selected peptide sequence. For example, the use of 7-amino-4-methyl coumarin (AMC) fluorogenic peptide substrates is a well-established method for the determination of protease specificity (Zimmerman, M., et al., (1977) *Analytical Biochemistry* 78:47–51). Specific cleavage of the anilide bond liberates the fluorogenic AMC leaving group allowing for the simple determination of cleavage rates for individual substrates. More recently, arrays (Lee, D., et al., (1999) *Bioorganic and Medicinal Chemistry Letters* 9:1667–72) and positional-scanning libraries (Rano, T. A., et al., (1997) *Chemistry and Biology* 4:149–55) of AMC peptide substrate libraries have been employed to rapidly profile the N-terminal specificity of proteases by sampling a wide range of substrates in a single experiment. Thus, one of skill may readily evaluate an array of peptide sequences to determine their utility in the present invention without resort to undue experimentation.

Disulfide Linkers

In yet a further aspect, the invention provides a cleaveable linker arm that is based upon a disulfide moiety. Thus, there is provided a compound having a structure according to Formula III:

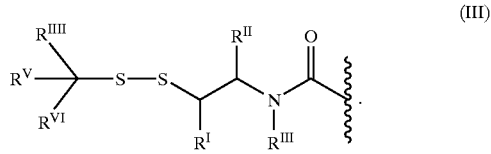

(III)

The identities of the radicals represented by the symbols R, $R^I$, $R^{II}$, $R^{III}$, $R^{IIII}$, $R^V$ and $R^{VI}$ are as described for R, $R^I$, $R^{II}$ and $R^{III}$ above.

In another embodiment, the invention provides a disulfide carbamate linker such as that set forth in Formula XIV:

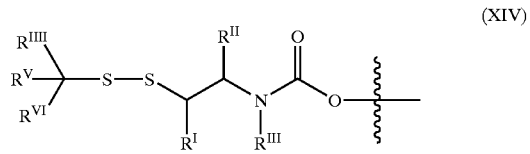

(XIV)

The identities of the radicals represented by the symbols R, $R^I$, $R^{II}$, $R^{III}$, $R^{IIII}$, $R^V$ and $R^{VI}$ are as described above.

As discussed above, the linkers of the invention can be used to form conjugates comprising a cytotoxin such as a combretastatin or a duocarmycin as the therapeutic agent. The duocarmycins are unstable in plasma. The linkers of the invention find particular utility in stabilizing the duocarmycins while in circulation, and liberating the agent (activation) once at the desired site of action. In addition, in order for the combretastatin or duocarmycin to regain maximum activity after activation, both the linker and the targeting group are preferably completely removed. Therefore, in one embodiment of the invention, the linkers are traceless linkers. Conjugates comprising a cytotoxin such as a duocarmycin as the therapeutic agent are also of particular interest. The linkers of the invention serve to stabilize duocarmycins in circulation and release an optimally potent cytotoxin after activation in or near the target cells. Since the cytotoxin is cleaved in or near the target cells, systemic toxicity due to random activation is decreased. Further, the increase in stability in circulation also provides for an increase in the half-life and overall effectiveness of the cytotoxin.

An exemplary route for preparing a disulfide linker arm-cytotoxin conjugate of the invention is set forth in Scheme 5.

Scheme 5

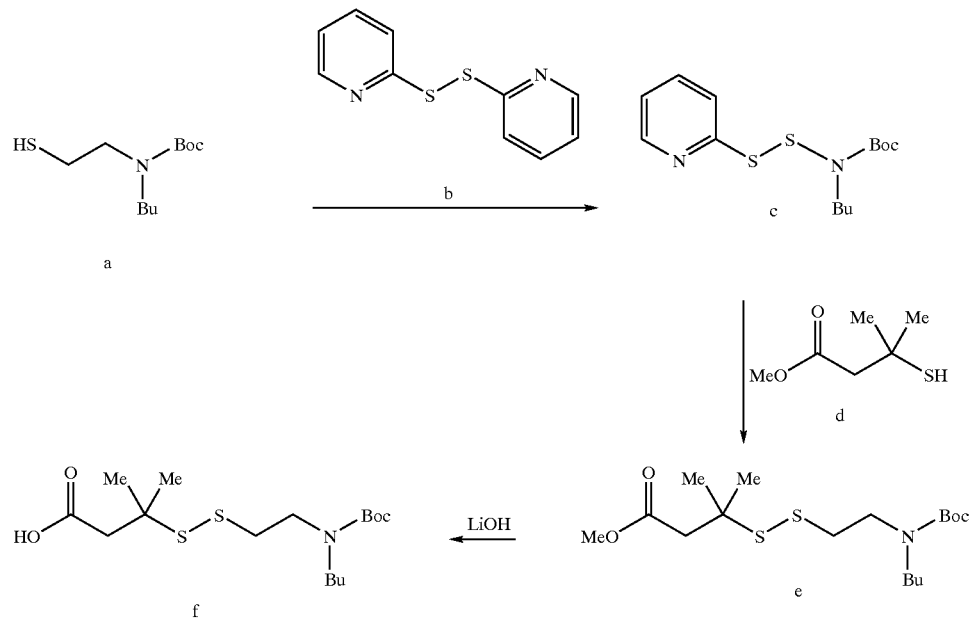

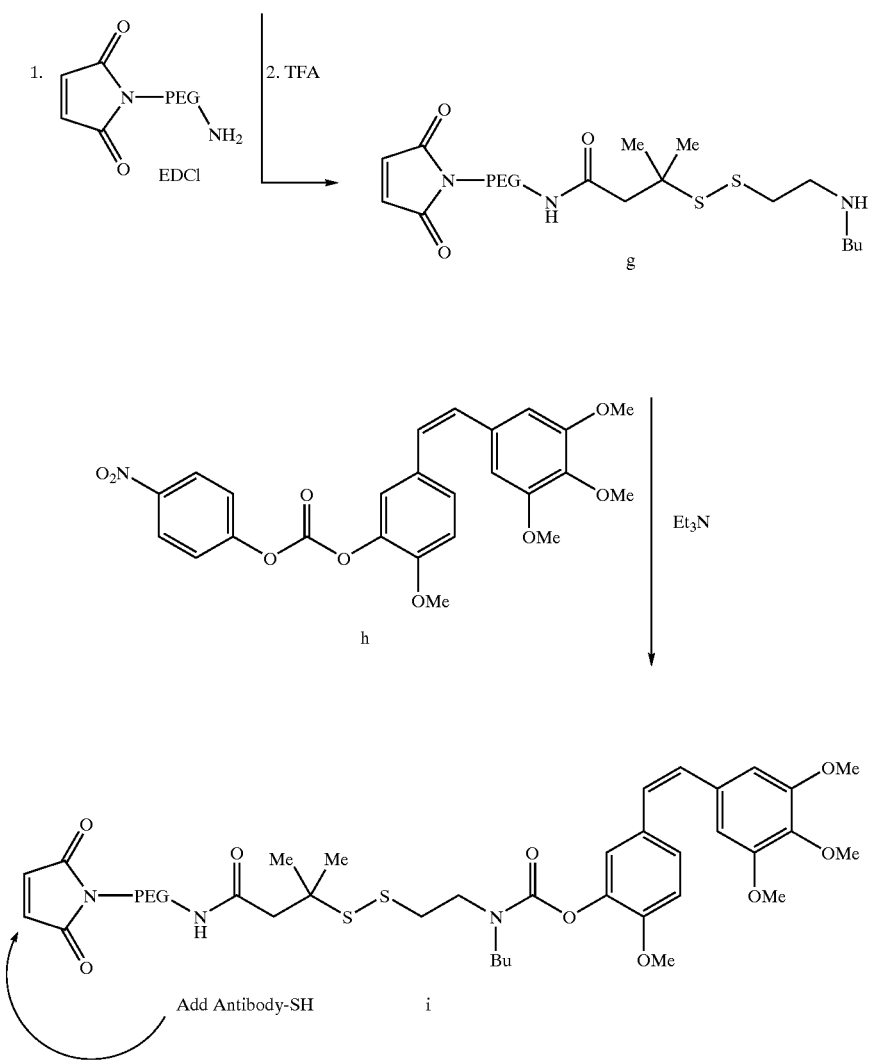

In Scheme 5, an amine-protected sulfhydryl a is reacted with 2,2'-dipyridyl disulfide b to form an amine-protected, activated disulfide c. The activated disulfide is contacted with a carboxylic ester bearing a free sulfhydryl d, eliminating pyridyl thiol and forming an amine-protected carboxylic ester that includes a disulfide moiety e. The methyl ester is cleaved by the action of LiOH to form the corresponding carboxylic acid f. The carboxylic acid is coupled to a heterobifunctional PEG molecule that includes a maleimide group and an amine by the action of EDCI to form compound g. The PEG derivative is contacted with an active carbonate of Combrestatin h to form conjugate i. If desired conjugate i can be attached to a targeting agent, detectable label or the like through the maleimide moiety.

In another embodiment, the invention provides a disulfide carbamate linker in which the non-carbonyl oxygen of the urethane linkage is derived from an aryl group. A representative linker of the invention is set forth in Formula XV:

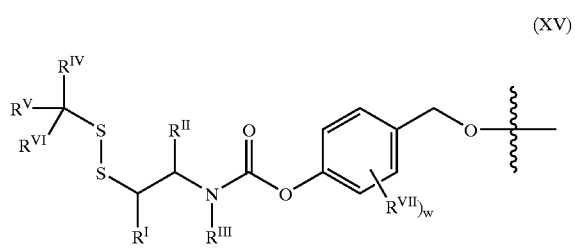

(XV)

The identity of the radicals is essentially as described above. $R^{VII}$ is a substituent on an aryl group as described in the definitions section. The symbol w represents an integer from 0 to 4. When more than one $R^{VII}$ is present, each of the groups is independently selected.

An exemplary route to compounds according to Formula XV is set forth in Scheme 6.

Scheme 6

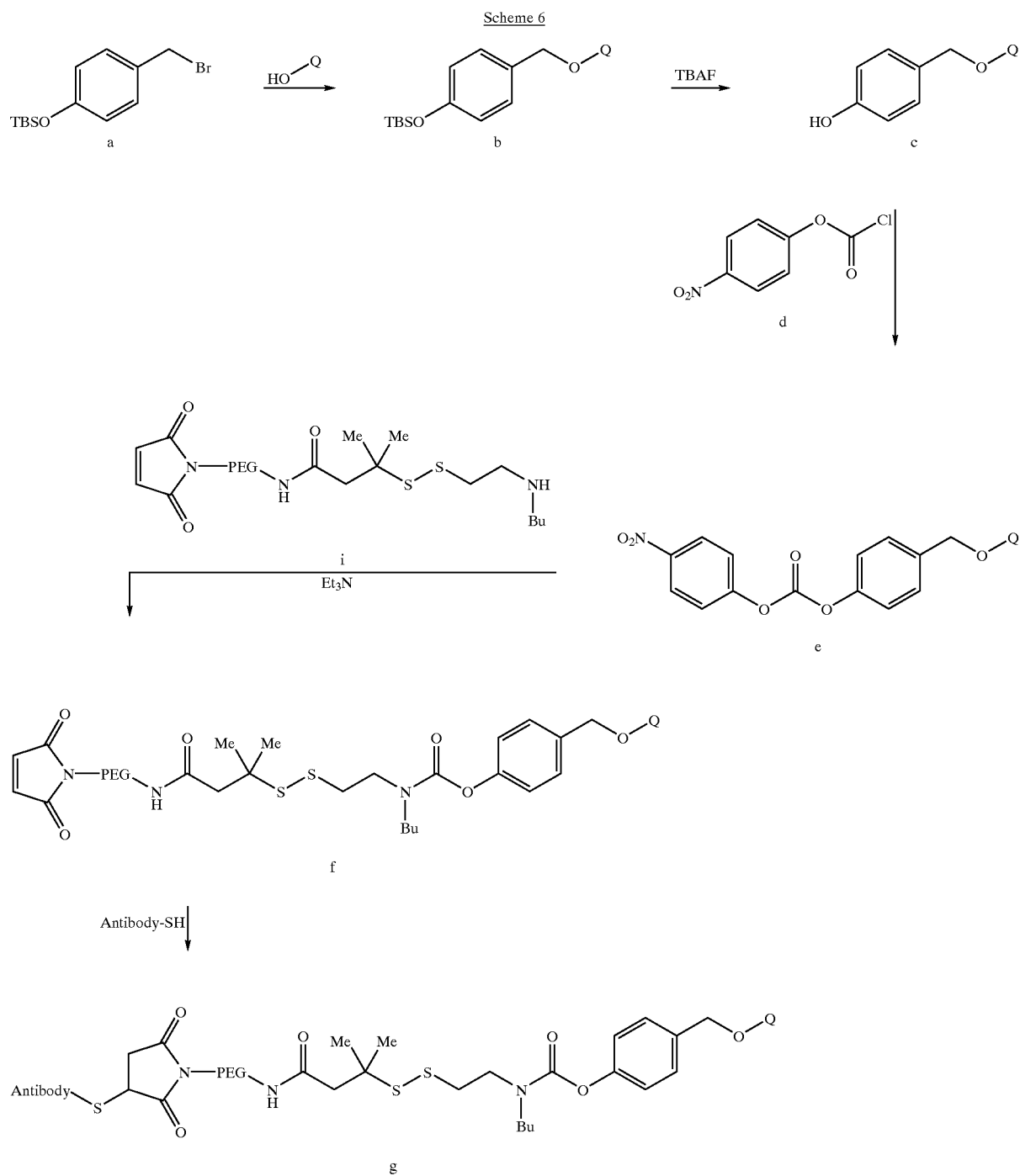

In Scheme 6, the TBS-alcohol protected benzyl bromide derivative a is reacted with Q—OH under alkylating conditions to form b. Compound b is deprotected by the action of tetrabutylammonium fluoride, forming c, which is acylated with d, forming carbonate e. Carbonate e is reacted with the heterobifunctional PEG derivative i from Scheme 5, supra. The resulting PEG adduct f can be conjugated to another molecule through the maleimide moiety.

Disulfide Linker-Duocarmycin Conjugates

As discussed above, the disulfide linkers of the invention are also useful components for stabilizing therapeutic or diagnostic moieties in vivo, forming prodrugs, and conjugating agents to species such as targeting agents, and detectable labels. Thus, in yet another aspect, the invention provides conjugates between a duocarmycin and a disulfide linker of the invention according to Formula I. Scheme 7 provides a facile route to a conjugate of the invention.

Scheme 7

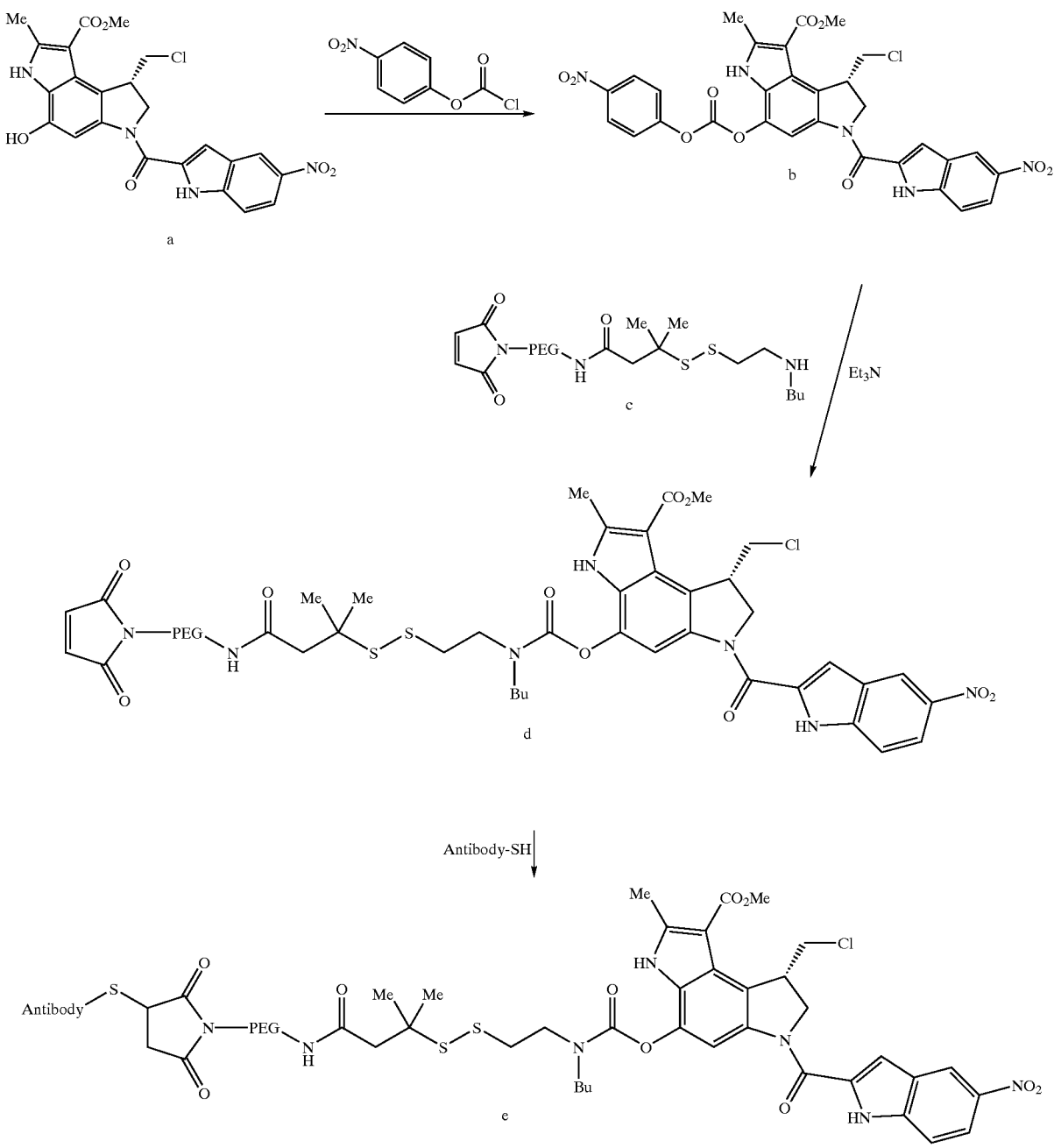

In Scheme 7, a duocarmycin cytotoxin of the invention a converted to the activated carbonate b with p-nitrophenylchloroformate. Compound b is coupled to the heterobifunctional PEG linker from Scheme 5, forming compound d, which may be subsequently coupled to an antibody through a maleimide-sulfhydryl coupling reaction to form conjugate e.

As discussed above, the therapeutic efficacy of certain toxic agents is dramatically improved by strategies that deliver the agent selectively to a desired site and/or maintain the agent in an essentially inactive form until it is delivered to the desired site of action. The present invention also provides linker arms that operate according to the principle of targeting an agent to a selected site and/or inactivating a bioactive agent until it reaches the desired site.

Thus, in certain embodiments, the invention provides conjugates of the cytotoxins set forth above, and of other agents as well, with linker arms having efficacious properties. In one embodiment, the linker arm conjugates a therapeutic or diagnostic moiety to an agent that selectively delivers the moiety to a desired site in the body. The linker between the moiety and the targeting agent can be stable in vivo, or it can be cleaved. If the agent is cleaved, it is preferably predominantly cleaved after it reaches the desired site of action.

In another embodiment, the invention provides linkers that do not tether a diagnostic or therapeutic moiety to another agent, but essentially inactivate the moiety until it reaches the desired site of activity; active species at the desired site of activity cleave the linker, preferably restoring the active form of the moiety. The strategy provides a means to mitigate the systemic toxicity of many toxic, but highly useful agents.

The urethane and disulfide linkers of the invention are exemplified in context with their conjugation with representative duocarmycin analogs of the invention. See, FIG. 1 and FIG. 3, respectively.

Targeting Agents

The linker arms and cytotoxins of the invention can be linked to targeting agents that selectively deliver a payload to a cell, organ or region of the body. Exemplary targeting agents such as antibodies (e.g., chimeric, humanized and human), ligands for receptors, lectins, saccharides, antibodies, and the like are recognized in the art and are useful without limitation in practicing the present invention. Other targeting agents include a class of compounds that do not include specific molecular recognition motifs include macromolecules such as poly(ethylene glycol), polysaccharide, polyamino acids and the like, which add molecular mass to the cytotoxin. The additional molecular mass affects the pharmacokinetics of the cytotoxin, e.g., serum half-life.

In an exemplary embodiment, the invention provides a cytotoxin, linker or cytotoxin-linker conjugate with a targeting agent that is a biomolecule, e.g, an antibody, receptor, peptide, lectin, saccharide, nucleic acid or a combination thereof. Routes to exemplary conjugates of the invention are set forth in the Schemes above.

Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments wherein the recognition moiety is a protein or antibody, the protein can be tethered to a SAM component or a spacer arm by any reactive peptide residue available on the surface of the protein. In preferred embodiments, the reactive groups are amines or carboxylates. In particularly preferred embodiments, the reactive groups are the ε-amine groups of lysine residues. Furthermore, these molecules can be adsorbed onto the surface of the substrate or SAM by non-specific interactions (e.g., chemisorption, physisorption).

Recognition moieties which are antibodies can be used to recognize analytes which are proteins, peptides, nucleic acids, saccharides or small molecules such as drugs, herbicides, pesticides, industrial chemicals and agents of war. Methods of raising antibodies for specific molecules are well-known to those of skill in the art. See, U.S. Pat. Nos. 5/147,786, issued to Feng et al. on Sep. 15, 1992; No. 5/334,528, issued to Stanker et al. on Aug. 2, 1994; No. 5/686,237, issued to Al-Bayati, M.A.S. on Nov. 11, 1997; and No. 5/573,922, issued to Hoess et al. on Nov. 12, 1996. Methods for attaching antibodies to surfaces are also art-known. See, Delamarche et al. *Langmuir* 12:1944–1946 (1996).

Targeting agents can be attached to the linkers of the invention by any available reactive group. For example, peptides can be attached through an amine, carboxyl, sulfhydryl, or hydroxyl group. Such a group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24:3031–3039 (1996).

When the peptide or nucleic acid is a fully or partially synthetic molecule, a reactive group or masked reactive group can be incorporated during the process of the synthesis. Many derivatized monomers appropriate for reactive group incorporation in both peptides and nucleic acids are know to those of skill in the art. See, for example, THE PEPTIDES: ANALYSIS, SYNTHESIS, BIOLOGY, Vol. 2: "Special Methods in Peptide Synthesis," Gross, E. and Melenhofer, J., Eds., Academic Press, New York (1980). Many useful monomers are commercially available (Bachem, Sigma, etc.). This masked group can then be unmasked following the synthesis, at which time it becomes available for reaction with a component of a compound of the invention.

In another exemplary embodiment, the targeting moiety is attached to a compound of the invention via an inclusion complex. For example, a compound or linker of the invention can include a moiety such as a cyclodextrin or modified cyclodextrin. Cyclodextrins are a group of cyclic oligosaccharides produced by numerous microorganisms. Cyclodextrins have a ring structure which has a basket-like shape. This shape allows cyclodextrins to include many kinds of molecules into their internal cavity. See, for example, Szejtli, J., CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978.

Cyclodextrins are able to form inclusion complexes with an array of organic molecules including, for example, drugs, pesticides, herbicides and agents of war. See, Tenjarla et al., *J. Pharm. Sci.* 87:425–429 (1998); Zughul et al., *Pharm. Dev. Technol.* 3:43–53 (1998); and Albers et al., *Crit. Rev. Ther. Drug Carrier Syst.* 12:311–337 (1995). Importantly, cyclodextrins are able to discriminate between enantiomers of compounds in their inclusion complexes. Thus, in one preferred embodiment, the invention provides for the detection of a particular enantiomer in a mixture of enantiomers. See, Koppenhoefer et al. *J. Chromatogr. A* 793:153–164 (1998). Numerous routes for attaching cyclodextrins to other molecules are known in the art. See, for example, Yamamoto et al., *J. Phys. Chem. B* 101:6855–6860 (1997); and Sreenivasan, K. *J. Appl. Polym. Sci.* 60:2245–2249 (1996).

The cytotoxin-targeting agent conjugates of the invention are further exemplified by reference to an antisense oligonucleotide-cytotoxin conjugate. The focus on cytotoxin-oligonucleotide conjugates is for clarity of illustration and is not limiting of the scope of targeting agents to which the cytotoxins of the invention can be conjugated.

Exemplary nucleic acid targeting agents include aptamers, antisense compounds, and nucleic acids that form triple helices. Typically, a hydroxyl group of a sugar residue, an amino group from a base residue, or a phosphate oxygen of the nucleotide is utilized as the needed chemical functionality to couple the nucleotide-based targeting agent to the cytotoxin. However, one of skill in the art will readily appreciate that other "non-natural" reactive functionalities can be appended to a nucleic acid by conventional techniques. For example, the hydroxyl group of the sugar residue can be converted to a mercapto or amino group using techniques well known in the art.

Aptamers (or nucleic acid antibody) are single- or double-stranded DNA or single-stranded RNA molecules that bind specific molecular targets. Generally, aptamers function by inhibiting the actions of the molecular target, e.g., proteins, by binding to the pool of the target circulating in the blood. Aptamers possess chemical functionality and thus, can covalently bond to cytotoxins, as described herein.

Although a wide variety of molecular targets are capable of forming non-covalent but specific associations with aptamers, including small molecules drugs, metabolites, cofactors, toxins, saccharide-based drugs, nucleotide-based drugs, glycoproteins, and the like, generally the molecular target will comprise a protein or peptide, including serum proteins, kinins, eicosanoids, cell surface molecules, and the like. Examples of aptamers include Gilead's antithrombin inhibitor GS 522 and its derivatives (Gilead Science, Foster City, Calif.). See also, Macaya et al. *Proc. Natl. Acad. Sci. USA* 90:3745–9 (1993); Bock et al. *Nature (London)* 355:564–566 (1992) and Wang et al. *Biochem.* 32:1899–904 (1993).

Aptamers specific for a given biomolecule can be identified using techniques known in the art. See, e.g., Toole et al. (1992) PCT Publication No. WO 92/14843; Tuerk and Gold (1991) PCT Publication No. WO 91/19813; Weintraub and Hutchinson (1992) PCT Publication No. 92/05285; and Ellington and Szostak, *Nature* 346:818 (1990). Briefly, these techniques typically involve the complexation of the molecular target with a random mixture of oligonucleotides. The aptamer-molecular target complex is separated from the uncomplexed oligonucleotides. The aptamer is recovered from the separated complex and amplified. This cycle is repeated to identify those aptamer sequences with the highest affinity for the molecular target.

For diseases that result from the inappropriate expression of genes, specific prevention or reduction of the expression of such genes represents an ideal therapy. In principle, production of a particular gene product may be inhibited, reduced or shut off by hybridization of a single-stranded deoxynucleotide or ribodeoxynucleotide complementary to an accessible sequence in the mRNA, or a sequence within the transcript that is essential for pre-mRNA processing, or to a sequence within the gene itself. This paradigm for genetic control is often referred to as antisense or antigene inhibition. Additional efficacy is imparted by the conjugation to the nucleic acid of an alkylating agent, such as those of the present invention.

Antisense compounds are nucleic acids designed to bind and disable or prevent the production of the mRNA responsible for generating a particular protein. Antisense compounds include antisense RNA or DNA, single or double stranded, oligonucleotides, or their analogs, which can hybridize specifically to individual mRNA species and prevent transcription and/or RNA processing of the mRNA species and/or translation of the encoded polypeptide and thereby effect a reduction in the amount of the respective encoded polypeptide. Ching et al. *Proc. Natl. Acad. Sci. U.S.A.* 86:10006–10010 (1989); Broder et al. *Ann. Int. Med.* 113:604–618 (1990); Loreau et al. *FEBS Letters* 274:53–56 (1990); Holcenberg et al. WO91/11535; WO91/09865; WO91/04753; WO90/13641; WO 91/13080, WO 91/06629, and EP 386563). Due to their exquisite target sensitivity and selectivity, antisense oligonucleotides are useful for delivering therapeutic agents, such as the cytotoxins of the invention to a desired molecular target.

Others have reported that nucleic acids can bind to duplex DNA via triple helix formation and inhibit transcription and/or DNA synthesis. Triple helix compounds (also referred to as triple strand drugs) are oligonucleotides that bind to sequences of double-stranded DNA and are intended to inhibit selectively the transcription of disease-causing genes, such as viral genes, e.g., HIV and herpes simplex virus, and oncogenes, i.e., they stop protein production at the cell nucleus. These drugs bind directly to the double stranded DNA in the cell's genome to form a triple helix and prevent the cell from making a target protein. See, e.g., PCT publications Nos. WO 92/10590, WO 92/09705, WO91/06626, and U.S. Pat. No. 5,176,996. Thus, the cytotoxins of the present invention are also conjugated to nucleic acid sequences that form triple helices.

The site specificity of nucleic acids (e.g., antisense compounds and triple helix drugs) is not significantly affected by modification of the phosphodiester linkage or by chemical modification of the oligonucleotide terminus. Consequently, these nucleic acids can be chemically modified; enhancing the overall binding stability, increasing the stability with respect to chemical degradation, increasing the rate at which the oligonucleotides are transported into cells, and conferring chemical reactivity to the molecules. The general approach to constructing various nucleic acids useful in antisense therapy has been reviewed by van der Krol et al., *Biotechniques* 6:958–976 (1988) and Stein et al. *Cancer Res.* 48:2659–2668 (1988). Therefore, in an exemplary embodiment, the cytotoxins of the invention are conjugated to a nucleic acid by modification of the phosphodiester linkage.

Moreover, aptamers, antisense compounds and triple helix drugs bearing cytotoxins of the invention can also can include nucleotide substitutions, additions, deletions, or transpositions, so long as specific hybridization to or association with the relevant target sequence is retained as a functional property of the oligonucleotide. For example, some embodiments will employ phosphorothioate analogs which are more resistant to degradation by nucleases than their naturally occurring phosphate diester counterparts and are thus expected to have a higher persistence in vivo and greater potency (see, e.g., Campbell et al., *J. Biochem. Biophys. Methods* 20:259–267(1990)). Phosphoramidate derivatives of oligonucleotides also are known to bind to complementary polynucleotides and have the additional capability of accommodating covalently attached ligand species and will be amenable to the methods of the present invention. See, for example, Froehler et al., *Nucleic Acids Res.* 16(11):4831 (1988).

In some embodiments the aptamers, antisense compounds and triple helix drugs will comprise O-methylribonucleotides (EP Publication No. 360609). Chimeric oligonucleotides may also be used (Dagle et al., *Nucleic Acids Res.* 18: 4751 (1990)). For some applications, antisense oligonucleotides and triple helix may comprise polyamide nucleic acids (Nielsen et al., *Science* 254: 1497 (1991) and PCT publication No. WO 90/15065) or other cationic derivatives (Letsinger et al., *J. Am. Chem. Soc.* 110: 4470–4471 (1988)). Other applications may utilize oligonucleotides wherein one or more of the phosphodiester linkages has been substituted with an isosteric group, such as a 2–4 atom long internucleoside linkage as described in PCT publication Nos. WO 92/05186 and 91/06556, or a formacetal group (Matteucci et al., *J. Am. Chem. Soc.* 113: 7767–7768 (1991)) or an amide group (Nielsen et al., *Science* 254: 1497–1500 (1991)).

In addition, nucleotide analogs, for example wherein the sugar or base is chemically modified, can be employed in the present invention. "Analogous" forms of purines and pyrimidines are those generally known in the art, many of which are used as chemotherapeutic agents. An exemplary but not exhaustive list includes 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, .beta.-D-mannosylqueosine, 5'methoxycarbonylmethyluracil, 5-methoxyuracil, 2-methylthio-N.sup.6-isopentenyladenine, uracil-5-oxyacetic acid methylester, uracil-5-oxyacetic acid (v), wybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid (v), pseudouracil, queosine, 2-thiocytosine, and 2,6-diaminopurine. In addition, the conventional bases by halogenated bases. Furthermore, the 2'-furanose position on the base can have a non-charged bulky group substitution. Examples of non-charged bulky groups include branched alkyls, sugars and branched sugars.

Terminal modification also provides a useful procedure to conjugate the cytotoxins to the nucleic acid, modify cell type specificity, pharmacokinetics, nuclear permeability, and absolute cell uptake rate for oligonucleotide pharmaceutical agents. For example, an array of substitutions at the 5' and 3' ends to include reactive groups are known, which allow covalent attachment of the cytotoxins. See, e.g., OLIGODE-OXYNUCLEOTIDES: ANTISENSE INHIBITORS OF GENE EXPRESSION, (1989) Cohen, Ed., CRC Press; PROSPECTS FOR ANTISENSE NUCLEIC ACID THERAPEUTICS FOR CANCER AND AIDS, (1991), Wickstrom, Ed., Wiley-Liss; GENE REGULATION: BIOLOGY OF ANTISENSE RNA AND DNA, (1992) Erickson and Izant, Eds., Raven Press; and ANTISENSE RNA AND DNA, (1992), Murray, Ed., Wiley-Liss. For general methods relating to antisense compounds, see, ANTISENSE RNA AND DNA, (1988), D. A. Melton, Ed., Cold Spring Harbor Laboratory, Cold Spring Harbor, N.Y.).

The targeting agent is generally coupled to the cytotoxin via a covalent bond. The covalent bond may be non-reversible, partially reversible, or fully reversible. The degree of reversibility corresponds to the susceptibility of the targeting agent-cytotoxin complex to in vivo degradation.

In a preferred embodiment, the bond is reversible (e.g., easily cleaved) or id partially reversible (e.g., partially or slowly cleaved). Cleavage of the bond can occur through biological or physiological processes. The physiological/biological processes cleave bonds at any selected location within the complex (e.g., removing an ester group or other protecting group that is coupled to an otherwise sensitive chemical functionality) before or after cleaving the bond between the cytotoxin and the linker, resulting in partially degraded complexes. Other cleavages can also occur, for example, between the linker and targeting agent.

For rapid degradation of the complex after administration, circulating enzymes in the plasma (e.g., amidases, reductases) are generally relied upon to cleave the dendrimer from the pharmaceutical agent. These enzymes can include non-specific aminopeptidases and esterases, dipeptidyl carboxy peptidases, proteases of the blood clotting cascade, and the like.

Alternatively, cleavage is through a nonenzymatic process. For example, chemical hydrolysis may be initiated by differences in pH experienced by the complex following delivery. In such a case, the complex may be characterized by a high degree of chemical lability at physiological pH of 7.4, while exhibiting higher stability at an acidic or basic pH in the delivery vehicle. An exemplary complex, which is cleaved in such a process is a complex incorporating a N-Mannich base linkage within its framework.

In most cases, cleavage of the complex will occur during or shortly after administration. However, in other embodiments, cleavage does not occur until the complex reaches the pharmaceutical agent's site of action.

The susceptibility of the cytotoxin-targeting agent complexes to degradation can be ascertained through studies of the hydrolytic or enzymatic conversion of the complex to the unbound pharmaceutical agent. Generally, good correlation between in vitro and in vivo activity is found using this method. See, e.g., Phipps et al., *J. Pharm. Sciences* 78:365 (1989). The rates of conversion are readily determined, for example, by spectrophotometric methods or by gas-liquid or high pressure liquid chromatography. Half-lives and other kinetic parameters may then be calculated using standard techniques. See, e.g., Lowry et al. MECHANISM AND THEORY IN ORGANIC CHEMISTRY, 2nd Ed., Harper & Row, Publishers, New York (1981).

Spacer Groups ("$L^x$")

In addition to the cleaveable group, one or more linker groups are optionally introduced between the cytotoxin and the targeting agent. Spacer groups contain at least two reactive functional groups. Typically, one chemical functionality of the spacer group bonds to a chemical functionality of the cytotoxin, while the other chemical functionality of the spacer group is used to bond to a chemical functionality of the targeting agent or the cleaveable linker. Examples of chemical functionalities of spacer groups include hydroxy, mercapto, carbonyl, carboxy, amino, ketone, and mercapto groups. The spacer may also be a component of the cleaveable linker, in which case it is generally denoted as $L^x$, where "x" is an integer.

The linkers, represented by $L^x$ are generally substituted or unsubstituted alkyl, substituted or unsubstituted aryl, substituted or unsubstituted heteroaryl or a substituted or unsubstituted heteroalkyl group.

Exemplary spacer groups include, for example, 6-aminohexanol, 6-mercaptohexanol, 10-hydroxydecanoic acid, glycine and other amino acids, 1,6-hexanediol, β-alanine, 2-aminoethanol, cysteamine (2-aminoethanethiol), 5-aminopentanoic acid, 6-aminohexanoic acid, 3-maleimidobenzoic acid, phthalide, α-substituted phthalides, the carbonyl group, aminal esters, nucleic acids, peptides and the like.

The spacer can serve to introduce additional molecular mass and chemical functionality into the cytotoxin-targeting agent complex. Generally, the additional mass and functionality will affect the serum half-life and other properties of the complex. Thus, through careful selection of spacer groups, cytotoxin complexes with a range of serum half-lives can be produced.

Reactive Functional Groups

For clarity of illustration the succeeding discussion focuses on the conjugation of a cytotoxin of the invention to a targeting agent. The focus exemplifies one embodiment of the invention from which, others are readily inferred by one of skill in the art. No limitation of the invention is implied, by focusing the discussion on a single embodiment.

Exemplary compounds of the invention bear a reactive functional group, which is generally located on a substituted or unsubstituted alkyl or heteroalkyl chain, allowing their facile attachment to another species. A convenient location for the reactive group is the terminal position of the chain.

Reactive groups and classes of reactions useful in practicing the present invention are generally those that are well known in the art of bioconjugate chemistry. Currently favored classes of reactions available with reactive cytotoxin analogues are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Exemplary reaction types include the reaction of carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters. Hydroxyl groups can be converted to esters, ethers, aldehydes, etc. Haloalkyl groups are converted to new species by reaction with, for example, an amine, a carboxylate anion, thiol anion, carbanion, or an alkoxide ion. Dienophile (e.g., maleimide) groups participate in Diels-Alder. Aldehyde or ketone groups can be converted to imines, hydrazones, semicarbazones or oximes, or via such mechanisms as Grignard addition or alkyllithium addition. Sulfonyl halides react readily with amines, for example, to form sulfonamides. Amine or sulfhydryl groups are, for example, acylated, alkylated or oxidized. Alkenes, can be converted to an array of new species using cycloadditions, acylation, Michael addition, etc. Epoxides react readily with amines and hydroxyl compounds.

One skilled in the art will readily appreciate that many of these linkages may be produced in a variety of ways and using a variety of conditions. For the preparation of esters, see, e.g., March supra at 1157; for thioesters, see, March, supra at 362–363, 491, 720–722, 829, 941, and 1172; for carbonates, see, March, supra at 346–347; for carbamates, see, March, supra at 1156–57; for amides, see, March supra at 1152; for ureas and thioureas, see, March supra at 1174; for acetals and ketals, see, Greene et al. supra 178–210 and March supra at 1146; for acyloxyalkyl derivatives, see, PRODRUGS: TOPICAL AND OCULAR DRUG DELIVERY, K. B. Sloan, ed., Marcel Dekker, Inc., New York, 1992; for enol esters, see, March supra at 1160; for N-sulfonylimidates, see, Bundgaard et al., *J. Med. Chem.,* 31:2066 (1988); for anhydrides, see, March supra at 355–56, 636–37, 990–91, and 1154; for N-acylamides, see, March supra at 379; for N-Mannich bases, see, March supra at 800–02, and 828; for hydroxymethyl ketone esters, see, Petracek et al. *Annals NY Acad. Sci.,* 507:353–54 (1987); for disulfides, see, March supra at 1160; and for phosphonate esters and phosphonamidates.

The reactive functional groups can be chosen such that they do not participate in, or interfere with, the reactions necessary to assemble the reactive autoinducer analogue. Alternatively, a reactive functional group can be protected from participating in the reaction by the presence of a protecting group. Those of skill in the art will understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

Typically, the targeting agent is linked covalently to a cytotoxin using standard chemical techniques through their respective chemical functionalities. Optionally, the dendrimer or agent is coupled to the agent through one or more spacer groups. The spacer groups can be equivalent or different when used in combination.

Generally, prior to forming the linkage between the cytotoxin and the targeting (or other) agent, and optionally, the spacer group, at least one of the chemical functionalities will be activated. One skilled in the art will appreciate that a variety of chemical functionalities, including hydroxy, amino, and carboxy groups, can be activated using a variety of standard methods and conditions. For example, a hydroxyl group of the cytotoxin or targeting agent can be activated through treatment with phosgene to form the corresponding chloroformate, or p-nitrophenylchloroformate to form the corresponding carbonate.

In an exemplary embodiment, the invention makes use of a targeting agent that includes a carboxyl functionality. Carboxyl groups may be activated by, for example, conversion to the corresponding acyl halide or active ester. This reaction may be performed under a variety of conditions as illustrated in March, supra pp. 388–89. In an exemplary embodiment, the acyl halide is prepared through the reaction of the carboxyl-containing group with oxalyl chloride. The activated agent is reacted with a cytotoxin or cytotoxin-linker arm combination to form a conjugate of the invention. Those of skill in the art will appreciate that the use of carboxyl-containing targeting agents is merely illustrative, and that agents having many other functional groups can be conjugated to the dendrimers of the invention.

When the compound of the invention is conjugated to a detectable label, the label is preferably a member selected from the group consisting of radioactive isotopes, fluorescent agents, fluorescent agent precursors, chromophores, enzymes and combinations thereof. Methods for conjugating various groups to antibodies are well known in the art. For example, a detectable label that is frequently conjugated to an antibody is an enzyme, such as horseradish peroxidase, alkaline phosphatase, β-galactosidase, and glucose oxidase.

Detectable Labels

The particular label or detectable group used in conjunction with the compounds and methods of the invention is generally not a critical aspect of the invention, as long as it does not significantly interfere with the activity or utility of the compound of the invention. The detectable group can be any material having a detectable physical or chemical property. Such detectable labels have been well developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to a compound of the invention according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to a component of the conjugate. The ligand then binds to another molecules (e.g., streptavidin) molecule, which is either inherently detectable or covalently bound to a signal system, such as a detectable enzyme, a fluorescent compound, or a chemiluminescent compound.

Components of the conjugates of the invention can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Fluorescent labels are presently preferred as they have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Many fluorescent labels are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful in the present invention. Such proteins include, for example, green fluorescent proteins of cnidarians (Ward et al., *Photochem. Photobiol.* 35:803–808 (1982); Levine et al., *Comp. Biochem. Physiol.*, 72B:77–85 (1982)), yellow fluorescent protein from Vibrio *fischeri* strain (Baldwin et al., *Biochemistry* 29:5509–15 (1990)), Peridinin-chlorophyll from the dinoflagellate Symbiodinium sp. (Morris et al., *Plant Molecular Biology* 24:673:77 (1994)), phycobiliproteins from marine cyanobacteria, such as Synechococcus, e.g., phycoerythrin and phycocyanin (Wilbanks et al., *J. Biol. Chem.* 268:1226–35 (1993)), and the like.

Pharmaceutical Formulations

In another preferred embodiment, the present invention provides a pharmaceutical formulation comprising a compound of the invention and a pharmaceutically acceptable carrier.

In a still further preferred embodiment, the invention provides a pharmaceutical formulation including a pharmaceutically acceptable carrier and a conjugate of a targeting agent with a cytotoxin of the invention.

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

As used herein, the terms "administering" or "administration" are intended to encompass all means for directly and indirectly delivering a compound to its intended site of action.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering from a disease state caused by an organism that relies on an autoinducer, the compounds of the invention can be administered in cocktails containing agents used to treat the pain, infection and other symptoms and side effects commonly associated with the disease. Such agents include, e.g., analgesics, antibiotics, etc.

When administered to a patient undergoing cancer treatment, the compounds may be administered in cocktails containing anti-cancer agents and/or supplementary potentiating agents. The compounds may also be administered in cocktails containing agents that treat the side-effects of radiation therapy, such as anti-emetics, radiation protectants, etc.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); $Ca^{+2}$ antagonists (e.g., verapamil, nifedipine, nitrendipine and caroverine); amphotericin; triparanol analogues (e.g., tamoxifen); anti-arrhythmic drugs (e.g., quinidine); antihypertensive drugs (e.g., reserpine); thiol depleters (e.g., buthionine and sulfoximine); and calcium leucovorin.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxyniethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Libraries

Also within the scope of the present invention are libraries of the cytotoxin, cytotoxin-linker and agent-linker conjugates of the cytotoxins and linkers of the invention. Exemplary libraries include at least 10 compounds, more preferably at least 100 compound, even more preferably at least 1000 compounds and still more preferably at least 100,000 compounds. The libraries in a form that is readily queried for a particular property, e.g., cytotoxicity, cleavage of a linker by an enzyme, or other cleavage reagent. Exemplary forms include chip formats, microarrays, and the like.

Parallel, or combinatorial, synthesis has as its primary objective the generation of a library of diverse molecules which all share a common feature, referred to throughout this description as a scaffold. By substituting different moieties at each of the variable parts of the scaffold molecule, the amount of space explorable in a library grows. Theories and modem medicinal chemistry advocate the concept of occupied space as a key factor in determining the efficacy of a given compound against a given biological target. By creating a diverse library of molecules, which explores a large percentage of the targeted space, the odds of developing a highly efficacious lead compound increase dramatically.

Parallel synthesis is generally conducted on a solid phase support, such as a polymeric resin. The scaffold, or other suitable intermediate is cleavably tethered to the resin by a chemical linker. Reactions are carried out to modify the scaffold while tethered to the particle. Variations in reagents and/or reaction conditions produce the structural diversity, which is the hallmark of each library.

Parallel synthesis of "small" molecules (non-oligomers with a molecular weight of 200–1000) was rarely attempted prior to 1990. See, for example, Camps. et al., *Annaks de Quimica*, 70: 848 (1990). Recently, Ellmann disclosed the solid phase-supported parallel (also referred to as "combinatorial") synthesis of eleven benzodiazepine analogs along with some prostaglandins and beta-turn mimetics. These disclosures are exemplified in U.S. Pat. No. 5,288,514. Another relevant disclosure of parallel synthesis of small molecules may be found in U.S. Pat. No. 5,324,483. This patent discloses the parallel synthesis of between 4 and 40 compounds in each of sixteen different scaffolds. Chen et al. have also applied organic synthetic strategies to develop non-peptide libraries synthesized using multi-step processes on a polymer support. (Chen et al., *J. Am. Chem. Soc.*, 116: 2661–2662 (1994)).

Once a library of unique compounds is prepared, the preparation of a library of immunoconjugates, or antibodies can be prepared using the library of autoinducers as a starting point and using the methods described herein.

Kits

In another aspect, the present invention provides kits containing one or more of the compounds or compositions of the invention and directions for using the compound or composition. In an exemplary embodiment, the invention provides a kit for conjugating a linker arm of the invention to another molecule. The kit includes the linker, and directions for attaching the linker to a particular functional group. Other formats for kits will be apparent to those of skill in the art and are within the scope of the present invention.

Methods

In addition to the compositions and constructs described above, the present invention also provides a number of methods that can be practiced utilizing the compounds and conjugates of the invention.

Purification

In another exemplary embodiment, the present invention provides a method for isolating a molecular target for a cytotoxin of the invention, which binds to a molecule having as a portion of its structure the group according to Formula I. The method preferably comprises, contacting a cellular preparation that includes the target with an immobilized compound according Formula I, thereby forming a complex between the receptor and the immobilized compound.

The cytotoxin of the invention can be immobilized on an affinity support by any art-recognized means. Alternatively, the cytotoxin can be immobilized using one or more of the linkers of the invention.

In yet another exemplary embodiment, the invention provides an affinity purification matrix that includes a linker of the invention.

The method of the invention for isolating a target will typically utilize one or more affinity chromatography techniques. Affinity chromatography enables the efficient isolation of species such as biological molecules or biopolymers by utilizing their recognition sites for certain supported chemical structures with a high degree of selectivity. The literature is replete with articles, monographs, and books on the subject of affinity chromatography, including such topics as affinity chromatography supports, crosslinking members, ligands and their preparation and use. A sampling of those references includes: Ostrove, *Methods Enzymol.* 182: 357–71 (1990); Ferment, *Bioeng.* 70: 199–209 (1990). Huang et al., *J. Chromatogr.* 492: 431–69 (1989); "Purification of enzymes by heparin-Sepharose affinity chromatography," *J. Chromatogr.*, 184: 335–45 (1980); Farooqi, *Enzyme Eng.*, 4: 441–2 (1978); Nishikawa, *Chem. Technol.*, 5(9): 564–71 (1975); Guilford et al., in, PRACT. HIGH PERFORM. LIQ. CHROMATOGR., Simpson (ed.), 193–206 (1976); Nishikawa, *Proc. Int. Workshop Technol. Protein Sep. Improv. Blood Plasma Fractionation*, Sandberg (ed.), 422–35; (1977) "Affinity chromatography of enzymes," *Affinity Chromatogr., Proc. Int. Symp.* 25–38, (1977) (Pub. 1978); and AFFINITY CHROMATOGRAPHY: A PRACTICAL APPROACH, Dean et al. (ed.), IRL Press Limited, Oxford, England (1985). Those of skill in the art have ample guidance in developing particular affinity chromatographic methods utilizing the materials of the invention.

In the present method, affinity chromatographic media of varying chemical structures can be used as supports. For example, agarose gels and cross-linked agarose gels are useful as support materials, because their hydrophilicity makes them relatively free of nonspecific binding. Other useful supports include, for example, controlled-pore glass (CPG) beads, cellulose particles, polyacrylamide gel beads and Sephadex™ gel beads made from dextran and epichlorohydrin.

Treatment of Disease

The cytotoxins of the invention are active, potent duocarmycin derivatives. The parent agents are exceptionally potent antitumor antibiotics that derive their biological effects through the reversible, stereoelectronically controlled sequence selective alkylation of DNA (Boger et al. *J. Org. Chem.* 55: 4499 (1990); Boger et al. *J. Am. Chem. Soc.* 112: 8961 (1990); Boger et al., *J. Am. Chem. Soc.* 113: 6645 (1991); Boger et al. *J. Am. Chem. Soc.* 115: 9872 (1993); Boger et al., *Bioorg. Med. Chem. Lett.* 2: 759 (1992)). Subsequent to the initial disclosure of the duocarmycins, extensive efforts have been devoted to elucidating the DNA alkylation selectivity of the duocarmycins and its structural origin.

In yet a further embodiment, the present invention provides a method of killing a cell. The method includes administering to the cell an amount of a compound of the invention sufficient to kill said cell. In an exemplary embodiment, the compound is administered to a subject bearing the cell. In a further exemplary embodiment, the administration serves to retard of stop the growth of a tumor that includes the cell.

Effective Dosages

Pharmaceutical compositions suitable for use with the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to reduce sickle cell dehydration and/or delay the occurrence of erythrocyte sickling or distortion in situ, such compositions will contain an amount of active ingredient effective to achieve this result. Determination of an effective amount is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of inhibition cell growth or division. In preferred embodiments, the cellular activity is at least 25% inhibited. Target plasma concentrations of active compound(s) that are capable of inducing at least about 50%, 75%, or even 90% or higher inhibition of cellular activity are presently preferred. The percentage of inhibition of cellular activity in the patient can be monitored to assess the appropriateness of the plasma drug concentration achieved, and the dosage can be adjusted upwards or downwards to achieve the desired percentage of inhibition.

As is well known in the art, therapeutically effective amounts for use in humans can also be determined from animal models. For example, a dose for humans can be formulated to achieve a circulating concentration that has been found to be effective in animals. The dosage in humans can be adjusted by monitoring cellular inhibition and adjusting the dosage upwards or downwards, as described above.

A therapeutically effective dose can also be determined from human data for compounds which are known to exhibit similar pharmacological activities. The applied dose can be adjusted based on the relative bioavailability and potency of the administered compound as compared with the known compound.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

For use in the prophylaxis and/or treatment of diseases related to abnormal cellular proliferation, a circulating concentration of administered compound of about 0.001 $\mu$M to 20 $\mu$M is preferred, with about 0.01 $\mu$M to 5 $\mu$M being preferred.

Patient doses for oral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day.

For other modes of administration, dosage amount and interval can be adjusted individually to provide plasma levels of the administered compound effective for the particular clinical indication being treated. For example, in one embodiment, a compound according to the invention can be administered in relatively high concentrations multiple times per day. Alternatively, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds, compositions and methods of the present invention are further illustrated by the examples that follow. These examples are offered to illustrate, but not to limit the claimed invention.

EXAMPLES

Examples 1

1.1 Material and Methods

In the examples below, unless otherwise stated, temperatures are given in degrees Celsius (° C.); operations were carried out at room or ambient temperature (typically a range of from about 18–25° C.; evaporation of solvent was carried out using a rotary evaporator under reduced pressure (typically, 4.5–30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours).

$^1$H-NMR spectra were measured on a Varian Mercury 300 MHz spectrometer and were consistent with the assigned structures. Chemical shifts were reported in parts per million (ppm) downfield from tetramethylsilane. Electrospray mass spectra were recorded on a Perkin Elmer Sciex API 365 mass spectrometer. Elemental analyses were performed by Robertson Microlit Laboratories, Madison, N.J. Silica gel for flash chromatography was E. Merck grade (230–400 mesh). Reverse-Phase analytical HPLC was performed on either a HP 1100 or a Varian ProStar 210 instrument with a Phenomenex Luna 5 $\mu$m C-18(2) 150 mm×4.6 mm column or a Varian Microsorb-MV 0.1 $\mu$m C-18 150 mm×4.6 mm column. A flow rate of 1 mL/min was with either a gradient of 0% to 50% buffer B over 15 minutes or 10% to 100% buffer B over 10 minutes with detection by UV at 254 nm. Buffer A, 20 mM ammonium formate +20% acetonitrile or 0.1% trifluoroacetic acid in acetonitrile; buffer B, 20 mM ammonium formate +80% acetonitrile or 0.1% aqueous trifluoroacetic acid. Reverse phase preparative HPLC were performed on a Varian ProStar 215 instrument with a Waters Delta Pak 15 $\mu$m C-18 300 mm×7.8 mm column.

1.2 Synthetic Methodology
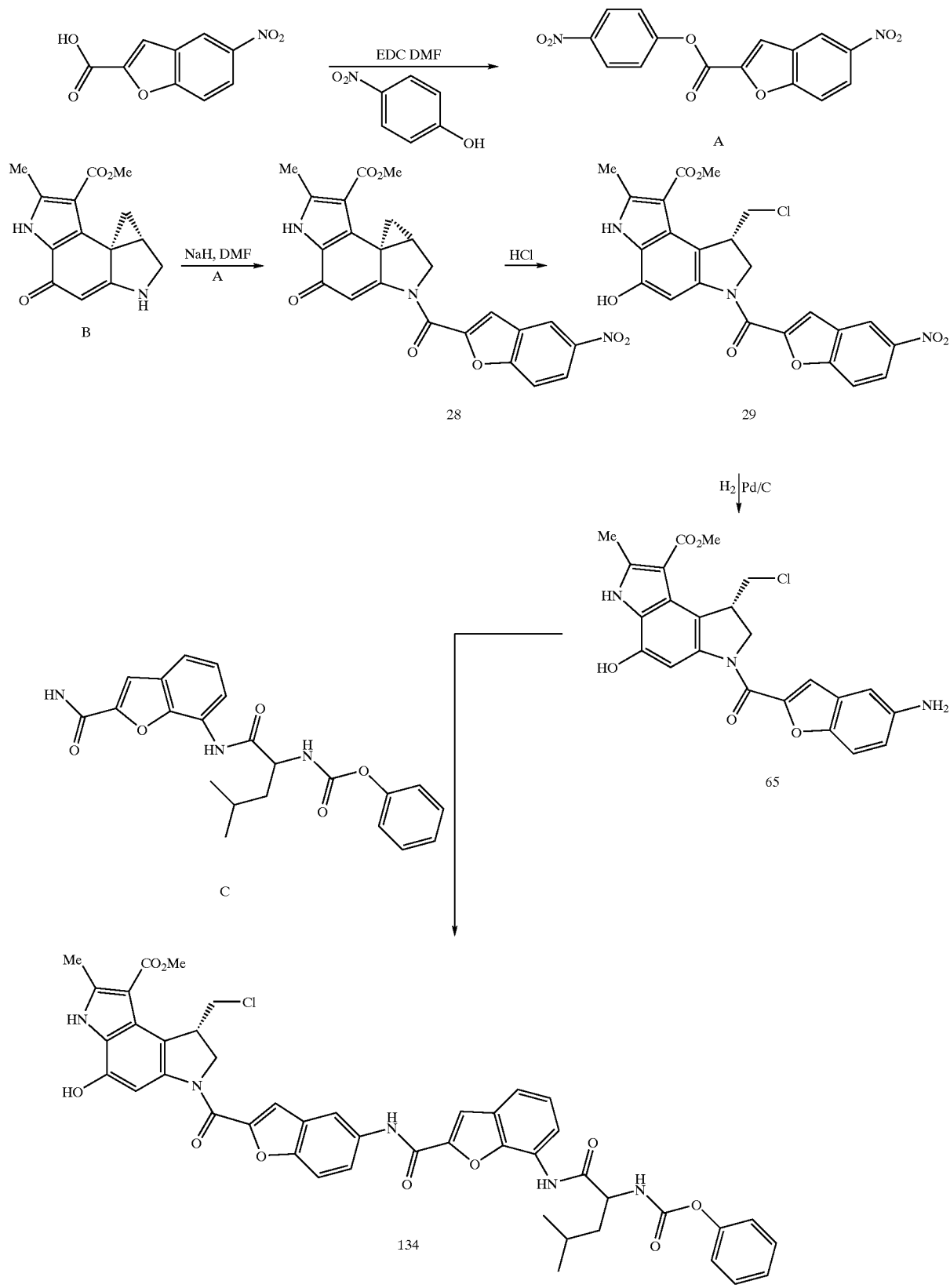

1.2a Synthesis of Compound 134

The compounds of Formula I are readily prepared by reacting the appropriate spirocyclopropylcyclohexadienly analog (Compounds B) with the activated heterocyclic compounds A using sodium hydride in N,B-dimethylformamide (DMF) or tetrahydrofuran (THF). The resulting compound 28 is then converted to compound 29 by treatment with the appropriate halo-acid, such as hydrochloric acid. Compound 29 is reduced by catalytic hydrogenation to give compound 65, which is coupled an activated ester to give compound 134, a compound of Formula I.

Other compounds of Formula I are prepared according to published procedures, which are modified to make additional analogs using procedures well known to those skilled in the art, such as reductions, oxidations, additions, aqueous extractions, evaporation, and purification.

1.2b Synthesis of Compound A

To a solution of 5-nitro-2-carboxylic acid (0.83 g, 4.0 mmol) in N,N-dimethylformamide (60 mL) at 0° C. was added EDC (1.15 g, 6.0 mmol). The resulting suspension was stirred at 0° C. for 45 min, by which time the EDC had completely dissolved. 4-Nitrophenol (0.83 g, 6.0 mmol) and DMAP (0.73 g, 6.0 mmol) were added and the resulting mixture stirred at ambient temperature. After 13 hours, the mixture was diluted with ethyl acetate and washed with a 10% aqueous citric acid solution twice, followed by water, and brine, then dried over $Na_2SO_4$, filtered and concentrated in vacuo. Purification of the resultant residue by flash column chromatography on silica gel (7% ethyl acetate in methylene chloride) afforded 1.02 g (78%) of A as a yellow solid: $^1H$ NMR ($CDCl_3$) δ9.0 (br s, 1 H), 8.2 (d, 2 H), 7.8 (m, 2 H), 7.4 (d, 2 H), 7.3 (s, 1 H), 6.8 (s, 1 H)

1.2c Synthesis of Compound 28

To a solution of B (20 mg, 0.08 mmol) in N,N-dimethylformamide (1.0 mL) at −40° C. was added a suspension of sodium hydride (4.0 mg, 0.1 mmol, 60% in oil) in N,N-dimethylformamide (1.0 mL). The resulting mixture was allowed to warm to 0° C. slowly (1.5 h), then cooled back to −40° C. A (37 mg, 0.1 mmol) was added and the mixture allowed to warm to 0° C. slowly (1.5 h) where it was kept for 20 min. The mixture was cooled to −30° C., quenched with acetic acid (10 υL), stirred for 10 min, diluted with ethyl acetate, then washed with water then brine. The organic layer was separated and dried over $MgSO_4$, filtered and concentrated in vacuo. Purification by flash column chromatography on silica gel (50% to 100% ethyl acetate in methylene chloride) afforded 16.3 mg (43%) of 28 as a slightly yellow solid: $^1H$ NMR ($CDCl_3$) δ11.3 (br s, 1 H), 9.4 (br s, 1 H), 7.4 (m, 2 H), 7.1 (s 1 H), 6.95 (s, 1 H), 6.8 (s, 1 H), 4.4 (s, 2 H), 3.8 (s, 3 H), 3.8 (m, 1 H), 2.6 (s, 3 H), 2.4 (dd, 1 H), 1.4 (m, 1 H). ESMS m/z 490 (M−H)⁻.

1.2d Synthesis of Compound 29

To a solution of 28 (50 mg, 0.103 mmol) in N,N-dimethylformamide (1.0 mL) was treated with 1 mL of anhydrous hydrochloric acid (1.0 M in dioxane). The resulting solution was stirred at ambient temperature for 30 min, then concentrated of solvent. Purification of the resulting residue by flash column chromatography on silica gel (50% to 100% ethyl acetate in methylene chloride) afforded 50 mg (100%) of 29 as a slightly yellow solid: $^1H$ NMR ($CDCl_3$) δ11.3 (br s, 1 H), 9.4 (br s, 1 H), 7.4 (m, 2 H), 7.1 (s, 1 H), 6.95 (s, 1 H), 6.8 (s, 1 H), 4.4 (s, 2 H), 3.8 (s, 3 H), 3.8 (m, 1 H), 2.6 (s, 3 H), 2.4 (dd, 1 H), 1.4 (m, 1 H).

1.2d Synthesis of Compound 65

To a solution of 29 (110 mg, 0.184 mmol) in 1:1 methanol:methylene chloride (20 ml) was added 10% palladium on carbon (100 mg). The mixture was hydrogenated on a Parr apparatus at 50 psi for one hour. The mixture was filtered over Celite, rinsed with methylene chloride, then concentrated in vacuo to give 94 mg (90% yield) of 65 as a yellow solid: $^1H$ NMR ($CDCl_3$) δ7.8–7.3 (m, 5 H), 4.4 (m, 3 H), 3.8 (m, 5 H), 3.4 (s, 3 H). ESMS m/z 454 (M−H)⁻.

1.2e Synthesis of Compound 134

Compound C (19 mg, 0.044 mmol) and HATU (50 mg, 0.132 mmol) were dissolved in dimethylformamide (2 ml)and the N-methylmorpholine (19.3 μl, 0.176 mmol) added. After 15 minutes, a solution of 65 (20 mg, 0.044 mmol) in dimethylformamide (1 ml) was added. The reaction mixture was stirred for 16 hours at room temperature, then concentrated in vacuo. The resulting solid was rinsed with water and saturated aqueous sodium bicarbonate, dried over vacuum, then washed with ethyl acetate. The crude product was purified by flash chromatography using silica gel and 5% methanol/methylene chloride to give 15 mg (39% yield) of 134: $^1H$ NMR (DMSO): δ11.4 (br s, 1H), 11.0 (br s, 1H), 10.9 (s, 1H), 8.5 (s, 1H), 8.3 (br s, 2H), 8.0 (m, 2H), 7.9 (s, 1H), 7.7 (m, 3H), 7.5 (d, 1H), 7.3 (t, 2H), 4.6 (m, 2H), 4.5 (d, 2H), 4.3 (m, 1H), 3.8 (s, 3H), 3.7 (d, 1H), 3.5 (t, 1H), 2.7 (s, 3H), 1.7 (m, 2H), 0.9 (d, 6H).

In a similar manner the following compounds were prepared:

46: $^1H$ NMR ($CDCl_3$): δ8.9 (s, 1H), 8.7 (s, 1H), 8.4 (dd, 1H), 8.1 (br s, 1H), 7.75 (d, 1H), 7.65 (s, 1H), 4.8 (d, 1H), 4.55 (m, 2H), 3.9 (s, 3H), 3.85 (s, 1H), 3.7 (m, 4H), 3.4 (t, 1H), 2.7 (s, 3H), 2.5 (br s, 4H), 2.4 (s, 3H).

95: $^1H$ NMR (DMSO): δ12 (s, 1H), 10.6 (d, 1H), 8.25 (s, 1H), 8.2 (br s, 1H), 8.1 (s, 1H), 7.7 (m, 5H), 7.5 (d, 1H), 4.6 (t, 1H), 4.5 (d, 1H), 4.4 (m, 2H), 4.1 (m, 1H), 3.9 (d, 2H), 3.8 (s, 3H), 3.3 (m, 10H), 2.8 (s, 3H), 2.6 (s, 3H), 1.6 (br s, 3H), 0.9 (s, 6H).

47: $^1H$ NMR ($CDCl_3$): δ9.1 (br s, 1H), 8.1 (br s, 1H), 7.4 (t, 2H), 6.9 (s, 1H), 6.8 (dd, 1H), 4.8 (d, 1H), 4.5 (m, 2H), 3.9 (s, 3H), 3.85 (m, 3H), 3.7 (m, 2H), 3.4 (t, 1H), 2.7 (s, 3H), 2.6 (br s, 4H), 2.4 (s, 3H).

52: $^1H$ NMR (DMSO): δ12.5 (s, 1H), 11.8 (s, 1H), 10.4 (s, 1H), 8.4 (s, 1H), 7.8 (m, 5H),7.5 (m, 2H), 7.3 (t, 1H), 7.1 (t, 1H), 6.7 (s, 1H), 4.6 (m, 4H), 3.8 (s, 3H), 2.5 (s, 3H).

108: $^1H$ NMR (DMSO): δ10.9 (s, 1H), 10.7 (s, 1H), 10.0 (s, 1H), 8.5 (s, 1H), 8.3 (s, 1H), 8.1 (m, 5H), 7.8 (m, 5H), 7.5 (m, 2H), 7.3 (m, 5H), 7.1 (m, 5H), 5.0 (m, 2H), 4.8 (m, 1H), 4.6 (m, 2H), 4.3 (m, 2H), 4.1 (t, 2H), 3.9 (m, 1H), 3.7 (m, 4H), 3.0 (m, 6H), 2.6 (s, 2H), 2.3 (t, 1H), 1.8 (s, 3H), 1.5 (m, 9H), 1.3 (m, 4H), 0.8 (m, 6H).

43: $^1H$ NMR (DMSO): δ12.1 (s, 2H), 11.8 (s, 1H), 10.5 (d, 1H), 8.3 (s, 1H), 8.0 (s, 1H), 7.8 (m, 5H), 7.6 (s, 1H), 7.2 (d, 2H), 4.7 (m, 2H), 4.5 (m, 3H), 3.8 (s, 3H), 3.5 (m, 2H), 3.2 (m, 2H), 2.9 (s, 3H), 2.7 (s, 3H), 2.3 (s, 4H).

153: $^1H$ NMR (DMSO): δ12.3 (br s, 1H), 11.7 (br s, 1H), 10.5 (br s, 1H), 10.0 (br s, 1H), 8.3 (m, 2H), 7.9 (m, 4H), 7.5 (s, 1H), 7.4 (d, 1H), 7.0 (m, 1H), 4.5 (m, 5H), 4.1 (m, 1H), 3.9 (d, 1H), 3.8 (s, 3H), 3.4 (m, 8H), 2.9 (br s, 3H), 2.8 (s, 3H), 2.7 (s, 3H), 1.8 (s, 2H), 1.6 (br s, 4H), 1.4 (m, 2H), 1.2 (d, 4H), 0.9 (m, 16H).

45: $^1H$ NMR (DMSO): δ12.0 (s, 1H), 11.6 (s, 1H), 10.8 (s, 1H), 8.4 (s, 1H), 8.3 (d, 2H), 8.0 (s, 1H), 7.8 (m, 3H), 7.6 (s, 1H), 7.4 (t, 1H), 4.6 (m, 5H), 3.8 (s, 3H), 3.4 (m, 8H), 2.9 (s, 3H), 2.7 (s, 3H).

115: $^1H$ NMR ($CDCl_3$): δ9.1 (br s, 1H), 8.4 (s, 1H), 8.3 (s, 1H), 7.7 (d, 1H), 7.5 (m, 3H), 7.2 (m, 3H), 6.9 (s, 2H), 4.7 (d, 1H), 4.5 (m, 4H), 3.9 (s, 3H), 3.5 (m, 14H), 2.6 (s, 3H), 1.3 (t, 3H).

109: $^1H$ NMR (DMSO): δ11.9 (s, 1H), 10.5 (s, 1H), 10.2 (d, 1H), 8.2 (s, 1H), 7.7 (m, 6H), 7.2 (d, 1H), 7.1 (t, 1H), 6.8 (d, 1H), 4.6 (m, 1H), 4.4 (d, 2H), 4.3 (m, 2H), 3.7 (s, 3H), 2.6 (s, 3H).

135: $^1H$ NMR (DMSO): δ11.4 (br s, 1H), 11.0 (br s, 1H), 10.9 (s, 1H), 8.5 (s, 1H), 8.3 (br s, 2H), 8.0 (m, 2H), 7.9 (s, 1H), 7.7 (m, 3H), 7.5 (d, 1H), 7.3 (t, 2H), 4.6 (m, 2H), 4.5 (d, 2H), 4.3 (m, 1H), 3.8 (s, 3H), 3.7 (d, 1H), 3.5 (t, 1H), 2.7 (s, 3H), 1.7 (m, 2H), 0.9 (d, 6H).

24: $^1H$ NMR (DMSO): δ10.8 (s, 1H), 8.6 (s, 1H), 8.3 (m, 5H), 7.9 (s, 1H), 7.8 (d, 2H), 7.7 (d, 1H), 7.65 (s, 1H), 7.6 (d, 2H), 7.4 (m, 5H), 5.3 (s, 2H), 4.9 (t, 1H), 4.7 (d, 1H), 4.4 (m, 1H), 4.0 (m, 2H).

ESMS m/z 696 (M−H)[31].

25: $^1$H NMR (DMSO): δ8.6 (s, 1H), 8.3 (m, 5H), 7.8 (m, 3H), 7.6 (m, 3H), 7.4 (m, 1H), 4.8 (m, 1H). 4.6 (m, 1H), 4.3 (m, 1H), 4.1 (m, 2H).
ESMS m/z 605 (M−H)−.
27: $^1$H NMR (DMSO): δ10.9 (s, 1H), 10.3 (s, 1H), 8.6 (s, 1H), 8.3 (s, 1H), 8.2 (d, 1H), 8.1 (m, 2H), 7.8 (m, 3H), 7.6 (d, 1H), 7.3 (s, 1H), 6.9 (d, 1H), 6.8 (t, 1H), 6.4 (d, 1H), 4.8 (t, 1H), 4.6 (d, 1H), 4.3 (m, 1H), 4.0 (m, 2H).
154: $^1$H NMR (DMSO): δ10.7 (s, 1H), 10.0 (s, 1H), 8.6 (s, 1H), 8.4 (s, 1H), 8.2 (s, 1H), 8.1 (m, 3H), 7.9 (m, 5H), 7.7 (m, 1H), 7.6 (m, 3H), 7.3 (m, 5H), 5.0 (s, 2H), 4.8 (t, 1H), 4.6 (d, 1H), 4.3 (m, 3H), 4.1 (d, 1H), 3.9 (m, 1H), 3.1 (s, 1H), 3.0 (m, 1H), 2.7 (s, 1H), 2.3 (m, 5H), 1.6 (m, 5H), 1.4 (t, 2H), 1.2 (d, 3H), 0.9 (m, 12H).
ESMS m/z 1134 (M−H)−.
162: $^1$H NMR (DMSO): δ11.6 (s, 1H), 10.9 (s, 1H), 10.5 (s, 1H), 9.9 (s, 1H), 8.6 (s, 1H), 8.3 (s, 1H), 8.2 (d, 1H), 8.0 (m, 5H), 7.8 (m, 4H), 7.6 (d, 1H), 7.5 (m, 3H), 7.1 (t, 1H), 4.8 (t, 1H), 4.6 (d, 2H), 4.3 (m, 3H), 4.1 (d, 1H), 3.9 (m, 1H), 2.4 (m, 2H), 2.3 (m, 3H)1.5 (m, 9H), 1.2 (m, 3H), 0.9 (m, 12H).
ESMS m/z 1044 (M−H)−.
79: $^1$H NMR (CDCl3): δ9.4 (s, 1H), 8.5 (s, 1H), 8.1 (s, 2H), 8.0 (br s, 1H), 7.9 (d, 2H), 7.6 (s, 2H), 7.5 (s, 1H), 7.0 (d, 2H), 6.9 (d, 3H), 4.7 (d, 1H), 4.5 (m, 2H), 4.2 (m, 1H), 3.95 (s, 3H), 3.85 (s, 3H), 3.7 (m, 4H), 3.4 (m, 1H), 2.7 (s, 3H), 2.5 (s, 3H), 2.4 (t, 2H), 1.1 (s, 9H), 0.4 (br s, 6H).
80: $^1$H NMR (CDCl3): δ9.3 (br s, 1H), 8.3 (s, 1H), 8.2 (br s, 1H), 8.0 (m, 3H), 7.5 (m, 4H), 7.4 (m, 2H), 7.0 (m, 4H), 4.7 (d, 1H), 4.6 (m, 1H), 4.4 (m, 1H), 4.2 (m, 5H), 3.9 (s, 3H), 3.4 (m, 1H), 2.7 (s, 3H), 2.9 (s, 3H), 2.3 (m, 2H), 1.1 (s, 9H), 0.4 (br s, 6H).
81: $^1$H NMR (CDCl3): δ10.5 (s, 1H), 8.8 (s, 1H), 8.6 (d, 2H), 8.0 (d, 2H), 7.8 (d, 2H), 7.4 (m, 3H), 7.3 (d, 2H), 7.0 (m, 2H), 6.9 (d, 2H), 4.6 (m, 3H), 4.4 (m, 2H), 3.9 (m, 4H), 3.4 (m, 1H), 2.7 (s, 3H), 2.5 (s, 3H), 1.0 (s, 9H), 0.3 (s, 6H).
82: $^1$H NMR (CDCl3): δ8.5 (s, 2H), 8.4 (s, 1H), 8.2 (s, 1H), 8.0 (m, 4H), 7.6 (m, 4H), 7.5 (s, 1H), 7.3 (s, 1H), 7.1 (s, 2H), 4.7 (m, 3H), 4.55 (m, 1H), 4.45 (m, 1H), 3.9 (m, 4H), 3.4 (m, 1H), 2.7 (s, 3H), 2.5 (s, 3H), 1.0 (s, 9H), 0.4 (br s, 6H).
83: $^1$H NMR (CDCl3): δ9.6 (s, 1H), 8.4 (s, 1H), 8.1 (s, 2H), 8.0 (m, 1H), 7.8 (s, 1H), 7.6 (m, 2H), 7.5 (s, 1H), 7.35 (q, 2H), 7.0 (s, 1H), 4.7 (d, 1H), 4.55 (m, 1H), 4.45 (m, 1H), 3.9 (m, 4H), 3.4 (m, 1H), 2.7 (s, 3H), 1.0 (s, 9H), 0.4 (br s, 6H).
89: $^1$H NMR (CDCl3): δ9.3 (br s, 1H), 8.4 (br s, 1H), 8.2 (s, 1H), 8.0 (br s, 2H), 7.5 (m, 9H), 7.2 (s, 1H), 7.1 (d, 1H), 6.9 (s, 1H), 5.1 (s, 2H), 4.7 (d, 1H), 4.55 (m, 1H), 4.45 (m, 1H), 3.9 (m, 4H), 3.4 (m, 1H), 2.7 (s, 3H), 1.05 (s, 9H), 0.4 (br s, 6H).
90: $^1$H NMR (CDCl3): δ9.6 (br s, 1H), 8.5 (br s, 1H), 8.2 (s, 1H), 8.0 (m, 2H), 7.5 (m, 8H), 7.3 (m, 2H), 7.1 (d, 1H), 6.6 (d, 1H), 5.2 (s, 2H), 4.7 (d, 1H), 4.55 (m, 1H), 4.45 (m, 1H), 3.9 (m, 4H), 3.4 (m, 1H), 2.7 (s, 3H), 1.05 (s, 9H), 0.3 (br s, 6H).
163: $^1$H NMR (DMSO): δ12.0 (s, 1H), 11.6 (s, 1H), 10.4 (s, 1H), 10.2 (s, 1H), 8.4 (s, 1H), 8.1 (m, 4H), 7.9 (m, 3H), 7.5 (m, 3H), 7.2 (d, 2H), 4.9 (s, 2H), 4.7 (m, 1H), 4.6 (m, 1H), 4.5 (m, 1H), 3.9 (m, 4H), 3.6 (m, 1H), 2.7 (s, 3H), 2.5 (s, 3H), 1.1 (s, 9H), 0.7 (s, 6H).
92: $^1$H NMR (DMSO): δ12.0 (s, 1H), 10.4 (s, 1H), 10.2 (s, 1H), 8.3 (s, 1H), 7.9 (s, 1H), 7.8 (m, 4H), 7.5 (d, 2H), 7.25 (s, 1H), 7.15 (s, 1H), 6.9 (m, 3H), 4.7 (m, 3H), 4.6 (m, 1H), 4.5 (m, 1H), 3.9 (m, 2H), 3.8 (m, 4H), 3.5 (m, 1H), 3.2 (m, 2H), 2.9 (s, 3H), 2.7 (s, 3H), 2.6 (s, 3H).
98: $^1$H NMR (CDCl3): δ8.3 (br s, 1H), 8.1 (d, 1H), 8.0 (br s, 1H), 7.95 (s, 1H), 7.85 (d, 2H), 7.65 (s, 1H), 7.6 (d, 2H), 7.5 (s, 1H), 7.4 (m, 2H), 7.0 (m, 1H), 6.85 (d, 2H), 4.8 (m, 3H), 4.55 (m, 1H), 4.45 (m, 1H), 3.9 (m, 6H), 3.4 (m, 1H), 2.7 (m, 3H), 2.5 (s, 3H), 2.4 (m, 2H), 1.05 (s, 9H), 0.4 (br s, 6H).

110: $^1$H NMR (C3D6O): δ11.3 (br s, 1H), 9.7 (s, 1H), 9.6 (d, 1H), 8.2 (s, 1H), 7.9 (m, 2H), 7.7 (d, 2H), 7.6 (m, 3H), 7.5 (d, 1H), 7.2 (m, 3H), 6.9(m, 3H), 6.8 (s, 1H), 4.9 (m, 2H), 4.7 (m, 1H), 4.6 (m, 1H), 4.5 (m, 1H), 3.8 (m, 25H), 3.5 (m, 1H), 3.2 (m, 2H), 2.7 (s, 3H), 2.3 (m, 4H), 2.0 (s, 3H).
113: $^1$H NMR (C3D6O): δ11.3 (br s, 1H), 10.1 (s, 1H), 9.9 (s, 1H), 8.4 (s, 1H), 7.9 (m, 3H), 7.7 (m, 2H), 7.5 (m, 3H), 7.4 (m, 1H), 7.2 (m, 1H), 7.1 (d, 2H), 6.9 (t, 1H), 5.0 (s, 2H), 4.6 (d, 1H), 4.5 (m, 1H), 4.4 (m, 1H), 3.9 (d, 1H), 3.7 (s, 3H), 3.4 (m, 1H), 2.6 (s, 3H), 2.4 (s, 3H).
114: $^1$H NMR (DMSO): δ11.9 (br s, 1H), 11.7 (s, 1H), 10.4 (d, 1H), 10.2 (t, 1H), 8.3 (s, 1H), 7.9 (s, 1H), 7.8 (m, 7H), 7.5 (m, 2H), 7.0 (m, 6H), 4.9 (s, 2H), 4.6 (m, 1H), 4.5 (m, 1H), 4.4 (m, 1H), 3.9 (d, 1H), 3.8 (s, 3H), 3.7 (m, 2H), 3.5 (m, 25H), 2.9 (s, 3H), 2.7 (s, 3H), 2.2 (m, 2H).
159: $^1$H NMR (DMSO): δ12.0 (m, 1H), 11.9 (br s, 1H), 8.3 (m, 2H), 8.0 (m, 4H), 7.6 (m, 2H), 7.3 (s, 1H), 7.1 (d, 1H), 6.9 (s, 1H), 4.5 (m, 3H), 4.3 (m, 2H), 3.9 (d, 1H), 3.8 (s, 6H), 3.5 (m, 8H), 3.2 (m, 4H), 2.7 (s, 3H), 2.3 (m, 4H), 1.4 (m, 9H), 1.1 (m, 3H), 0.8 (m, 12H).
131: $^1$H NMR (DMSO): δ11.9 (s, 1H), 10.2 (s, 1H), 7.7 (m, 1H), 7.5 (s, 1H), 7.0 (m, 3H), 6.7 (d, 1H), 4.7 (m, 1H), 4.4 (d, 1H), 4.3 (m, 2H), 3.9 (d, 1H), 3.8 (s, 3H), 2.6 (s, 3H).
129: $^1$H NMR (DMSO): δ11.9 (s, 1H), 10.2 (s, 1H), 7.8 (m, 4H), 4.5 (m, 2H), 4.3 (m, 1H), 3.9 (s, 3H), 3.8 (d, 1H), 3.7 (s, 3H), 3.4 (t, 1H), 2.5 (s, 3H).
136: $^1$H NMR (DMSO): δ11.9 (s, 1H), 10.2 (s, 1H), 7.65 (d, 2H), 7.55 (s, 1H), 7.3 (d, 1H), 7.1 (dd, 1H), 4.6 (m, 1H), 4.5 (m, 1H), 4.3 (m, 1H), 3.85 (m, 1H), 3.8 (s, 3H), 3.75 (s, 3H), 3.5 (m, 1H), 2.6 (s, 3H).
137: $^1$H NMR (DMSO): δ11.9 (s, 1H), 10.2 (s, 1H), 8.0 (m, 1H), 7.5 (m, 3H), 7.2 (s, 1H), 7.0 (m, 1H), 4.6 (m, 1H), 4.5 (m, 1H), 4.4 (m, 1H), 3.9 (m, 2H), 3.8 (d, 1H), 3.7 (s, 3H), 3.4 (m, 1H), 2.6 (s, 3H), 2.4 (m, 2H), 1.3 (m, 9H).
143: $^1$H NMR (DMSO): δ11.9 (s, 1H), 10.2 (s, 1H), 8.0 (m, 2H), 7.7 (m, 3H), 7.3 (s, 1H), 7.1 (d, 1H), 4.6 (m, 1H), 4.5 (m, 1H), 4.3 (m, 1H), 4.2 (m, 2H), 3.9 (d, 1H), 3.8 (s, 3H), 3.4 (m, 1H), 3.3 (m, 2H), 2.6 (s, 3H).
148: $^1$H NMR (DMSO): δ11.9 (s, 1H), 10.1 (s, 1H), 7.7 (d; 2H), 7.5 (s, 1H), 7.3 (s, 1H), 7.1 (d, 1H), 4.5 (m, 1H), 4.4 (d, 1H), 4.3 (m, 3H), 3.8 (s, 3H), 3.7 (s, 3H), 3.5 (m, 3H), 2.8 (s, 6H), 2.5 (s, 3H).
150: $^1$H NMR (DMSO): δ10.3 (s, 1H), 9.4 (s, 1H), 7.8 (m, 1H), 7.5 (m, 2H), 7.1 (s, 1H), 6.9 (dd, 1H), 4.5 (m, 4H), 4.3 (m, 1H), 3.8 (s, 3H), 3.75 (d, 1H), 3.5 (m, 1), 3.1 (m, 2H), 2.75 (s, 6H), 2.65 (s, 3H), 2.1 (m, 2H).
151: $^1$H NMR (DMSO): δ11.9 (s, 1H), 10.2 (s, 1H), 7.7 (d, 2H), 7.65 (s, 1H), 7.55 (s, 1H), 7.25 (d, 1H), 4.6 (m, 1H), 4.5 (m, 1H), 4.4 (m, 1H), 3.9 (d, 1H), 3.8 (s, 3H), 3.5 (m, 1H), 3.3 (br m, 8H), 2.9 (s, 3H), 2.6 (s, 3H).
251: $^1$H NMR (CDCl3): δ12.0 (s, 1H), 7.9 (m, 1H), 7.7 (d, 1H), 7.6 (s, 1H), 7.4 (s, 1H), 7.2 (dd, 1H), 4.6 (m, 3H), 4.4 (m, 2H), 3.9 (m, 1H), 3.8 (s, 3H), 3.7 (m, 1H), 3.6 (m, 2H), 3.4 (m, 4H), 3.2 (m, 2H), 3.0 (m, 4H), 2.9 (s, 6H), 2.7 (m, 4H), 2.6 (s, 2H), 1.6 (m, 2H), 1.3 (m, 8H), 0.9 (q, 2H).
227: $^1$H NMR (CDCl3): δ10.3 (s, 1H), 8.7 (s, 1H), 7.7 (d, 2H), 7.5 (m, 3H), 7.1 (m, 2H), 6.9 (d, 2H), 4.6 (m, 5H), 4.25 (m, 2H), 4.15 (m, 2H), 3.9 (s, 3H), 3.4 (m, 1H), 3.1 (s, 2H), 2.9 (m, 12H), 2.7 (s, 3H), 2.5 (s, 6H), 2.3 (s, 3H).
230: $^1$H NMR (CDCl3): δ10.3 (s, 1H), 8.6 (s, 1H), 7.7 (d, 2H), 7.5 (m, 3H), 7.1 (m, 2H), 6.9 (d, 2H), 6.7 (s, 2H), 4.7 (m, 4H), 4.1 (m, 4H), 3.9 (s, 3H), 3.5 (m, 2H), 3.4 (m, 1H), 3.2 (m, 4H), 3.1 (s, 2H), 2.8 (m, 5H), 2.4 (m, 10H), 2.2 (m, 7H).
166: ESMS m/z 532 (M−H)−.
165: ESMS m/z 920 (M−H)−.
9: ESMS m/z 966 (M−H)−.
17: ESMS m/z 753 (M−H)−.
19: ESMS m/z 696 (M−H)−.
50: ESMS m/z 800 (M−H)−.
174: $^1$H NMR (CDCl3): δ8.4 (s, 1H), 7.9 (in, 1H), 7.5 (m, 2H), 7.2 (m, 2H), 4.75 (in, 3H), 4.6 (in, 1H), 4.45 (in, 1H), 3.9 (m, 4H), 3.4 (m, 1H), 2.7 (s, 3H), 1.05 (s, 9H), 0.4 (br s, 6H); ESMS m/z 627 (M−H)⁻.
176: ¹H NMR (CDCl₃): δ8.4 (s, 1H), 7.9 (m, 1H), 7.5 (m, 2H), 7.1 (m, 2H), 4.7 (m, 3H), 4.6 (m, 1H), 4.45 (m, 1H), 3.9 (m, 4H), 3.4 (m, 1H), 2.7 (s, 3H), 1.05 (s, 9H), 0.4 (br s, 6H).
94: ¹H NMR (CDCl₃): δ8.5 (d, 2H), 8.2 (d, 2H), 7.9 (s, 2H), 7.8 (d, 2H), 7.5(m, 2H), 7.4 (m, 4H), 6.8 (d, 2H), 4.7 (d, 1H), 4.5 (m, 1H), 4.4 (m, 1H), 3.9 (m, 6H), 3.3 (m, 1H), 2.9 (t, 2H), 2.7 (s, 3H), 2.5 (s, 3H), 2.1 (m, 2H), 1.6 (s, 6H), 1.0 (s, 9H), 0.3 (br s, 6H).
ESMS m/z 1038 (M−H)⁻.
Example 2
2.1 Synthesis Methodology
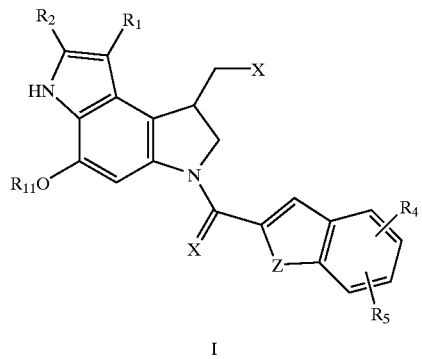
I
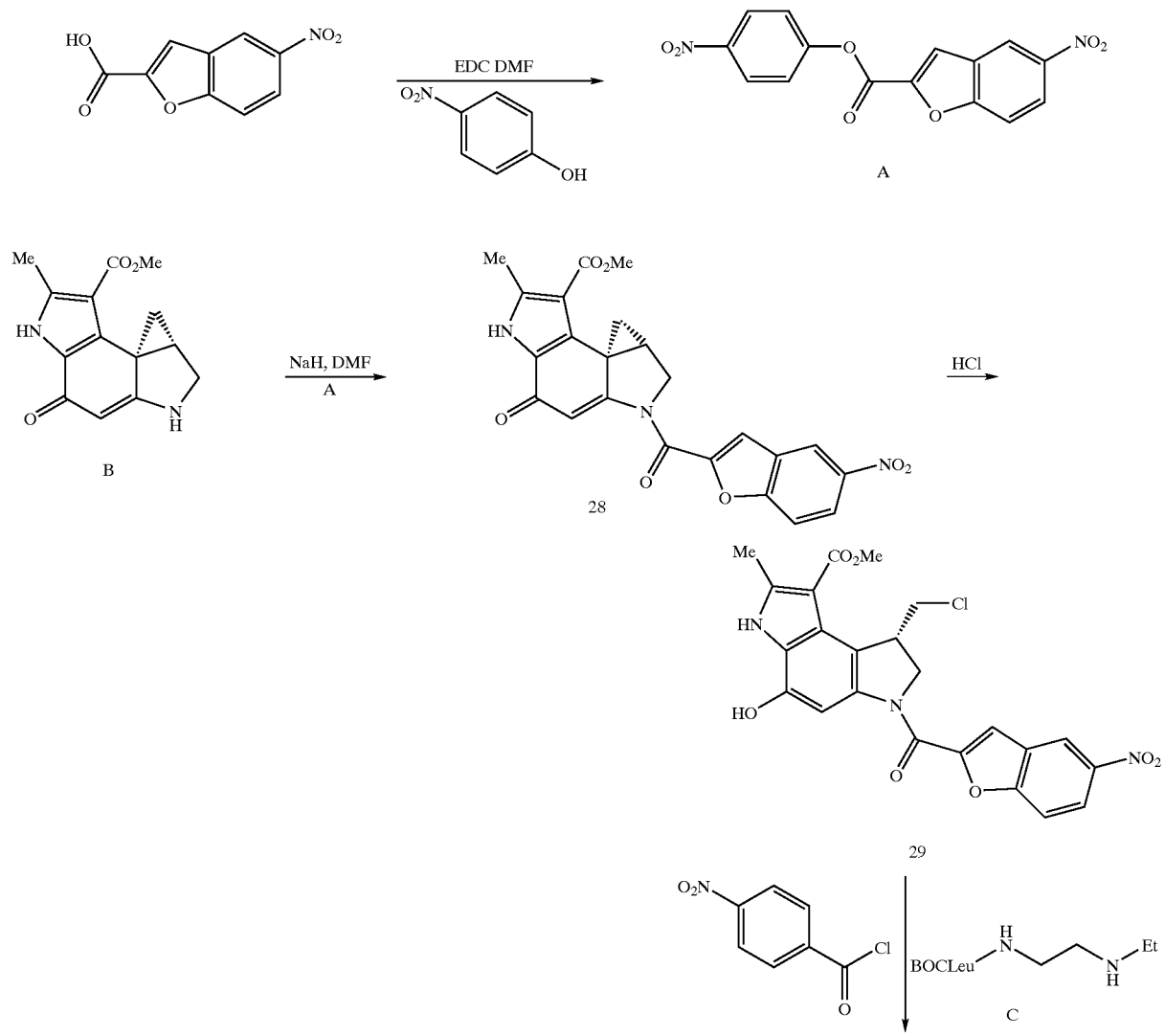

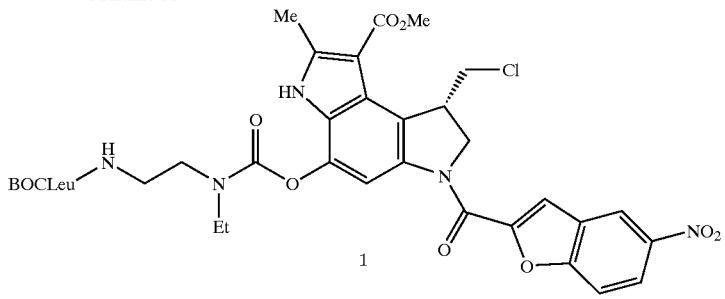

2.1a Synthesis of Compound 1

The compounds of Formula I are readily prepared by reacting the appropriate spirocyclopropylcyclohexadienly analog (Compounds B) with the activated heterocyclic compounds A using sodium hydride in N,B-dimethylformamide (DMF) or tetrahydrofuran (THF). The resulting compound 28 is then converted to compound 29 by treatment with the appropriate halo-acid, such as hydrochloric acid. Coupling with compound 29 by in situ activation is used to produce compound 1, a compound of Formula I.

Other compounds of Formula I are prepared according to published procedures, which are modified to make additional analogs using procedures well known to those skilled in the art, such as reductions, oxidations, additions, aqueous extractions, evaporation, and purification.

2.1b Synthesis of Compound A

To a solution of 5-nitro-2-carboxylic acid (0.83 g, 4.0 mmol) in N,N-dimethylformamide (60 mL) at 0° C. was added EDC (1.15 g, 6.0 mmol). The resulting suspension was stirred at 0° C. for 45 min, by which time the EDC had completely dissolved. 4-Nitrophenol (0.83 g, 6.0 mmol) and DMAP (0.73 g, 6.0 mmol) were added and the resulting mixture stirred at ambient temperature. After 13 hours, the mixture was diluted with ethyl acetate and washed with a 10% aqueous citric acid solution twice, followed by water, and brine, then dried over $Na_2SO_4$, filtered and concentrated in vacuo. Purification of the resultant residue by flash column chromatography on silica gel (7% ethyl acetate in methylene chloride) afforded 1.02 g (78%) of A as a yellow solid: $^1$H NMR ($CDCl_3$) δ9.0 (br s, 1 H), 8.2 (d, 2 H), 7.8 (m, 2 H), 7.4 (d, 2 H), 7.3 (s, 1 H), 6.8 (s, 1 H).

2.1c Synthesis of Compound 28

To a solution of B (20 mg, 0.08 mmol) in N,N-dimethylformamide (1.0 mL) at −40° C. was added a suspension of sodium hydride (4.0 mg, 0.1 mmol, 60% in oil) in N,N-dimethylformamide (1.0 mL). The resulting mixture was allowed to warm to 0° C. slowly (1.5 h), then cooled back to −40° C. A (37 mg, 0.1 mmol) was added and the mixture allowed to warm to 0° C. slowly (1.5 h) where it was kept for 20 min. The mixture was cooled to −30° C., quenched with acetic acid (10 υL), stirred for 10 min, diluted with ethyl acetate, then washed with water then brine. The organic layer was separated and dried over $MgSO_4$, filtered and concentrated in vacuo. Purification by flash column chromatography on silica gel (50% to 100% ethyl acetate in methylene chloride) afforded 16.3 mg (43%) of 28 as a slightly yellow solid: $^1$H NMR ($CDCl_3$) δ11.3 (br s, 1 H), 9.4 (br s, 1 H), 7.4 (m, 2 H), 7.1 (s, 1 H), 6.95 (s, 1 H), 6.8 (s, 1 H), 4.4 (s, 2 H), 3.8 (s, 3 H), 3.8 (m, 1 H), 2.6 (s, 3 H), 2.4 (dd, 1 H), 1.4 (m, 1 H). ESMS m/z 490 (M−H)$^-$.

2.1d Synthesis of Compound 29

To a solution of 28 (50 mg, 0.103 mmol) in N,N-dimethylformamide (1.0 mL) was treated with 1 mL of anhydrous hydrochloric acid (1.0 M in dioxane). The resulting solution was stirred at ambient temperature for 30 min, then concentrated of solvent. Purification of the resulting residue by flash column chromatography on silica gel (50% to 100% ethyl acetate in methylene chloride) afforded 50 mg (100%) of 29 as a slightly yellow solid: $^1$H NMR ($CDCl_3$) δ11.3 (br s, 1 H), 9.4 (br s, 1 H), 7.4 (m, 2 H), 7.1 (s, 1 H), 6.95 (s, 1 H), 6.8 (s, 1 H), 4.4 (s, 2 H), 3.8 (s, 3 H), 3.8 (m, 1 H), 2.6 (s, 3 H), 2.4 (dd, 1 H), 1.4 (m, 1 H).

2.1e Synthesis of Compound 1

To a solution of 29 (66 mg, 0.136 mmol) in anhydrous methylene chloride (10 mL) at −70° C. was added 4-nitrophenylchloroformate (55 mg, 0.273 mmol), followed by triethylamine (27 mg, 0.273 mmol). The resulting mixture was allowed to warm slowly. After 2 hours, the mixture was placed in an ice bath and amine C (82 mg, 0.273 mmol) was added in one portion. The resulting mixture was stirred at ambient temperature overnight. After 22 hours, the mixture was poured into saturated aqueous $NaHCO_3$ (aq). The aqueous layer was separated and extracted with methylene chloride. The combined organic extracts were dried over $MgSO_4$, filtered and concentrated in vacuo. Purification by flash column chromatography on silica gel (1% to 2% methanol in methylene chloride) afforded 42 mg (38%) of 1 as a slightly yellow solid: $^1$H NMR ($CDCl_3$) δ11.0 (s, 1 H), 8.6 (s, 1 H), 8.4 (d, 1 H), 8.2 (br d, 1 H), 7.6 (m, 2 H), 6.8 (m, 1 H), 4.8 (m, 1 H), 4.7 (m, 1 H), 4.5 (m, 1 H), 4.1 (m, 2 H), 3.9 (s, 3 H), 3.4 (m, 5 H), 2.7 (d, 3 H), 1.6 (s, 6 H), 1.4 (s, 9 H), 1.2 (m, 4 H), 0.9 (m, 9 H).

In a similar manner the following compounds were prepared:

220: $^1$H NMR ($CDCl_3$): δ11.4 (d, 1H), 8.7 (s, 1H), 8.4 (, dd, 1H), 8.1 (br s, 1H), 7.75 (d, 1H), 7.65 (s, 1H), 5.8 (br s, 2H), 4.7 (m, 1H), 4.5 (m, 2H), 4.2 (m, 1H), 3.9 (s, 3H), 3.4 (m, 1H), 3.0 (s, 2H), 2.75 (s, 3H), 2.65 (s, 3H).

ESMS m/z 613 (M−H)$^-$.

222: $^1$H NMR ($CDCl_3$): δ10.3 (s, 1H), 8.7 (d, 2H), 8.4 (d, 1H), 8.1 (m, 1H), 7.7 (d, 2H), 7.6 (m, 1H), 6.9 (d, 2H), 4.9 (d, 1H), 4.7 (m, 1H), 4.5 (m, 3H), 3.95 (s, 3H), 3.85 (s, 3H), 3.6 (m, 1H), 3.4 (m, 1H), 3.1 (s, 3H), 2.7 (s, 3H), 2.3 (s, 3H).

ESMS m/z 745 (M−H)$^-$.

224: ESMS m/z 899 (M−H)$^-$.

229: ESMS m/z 598 (M−H)$^-$.

233: ESMS m/z 816 (M−H)$^-$.

235: ESMS m/z 913 (M−H)$^-$.

8: ESMS m/z 856 (M−H)$^-$.

232: ESMS m/z 612 (M−H)$^-$.

234: ESMS m/z 952 (M−H)$^-$.

Example 3
3.1 Synthesis Methodology

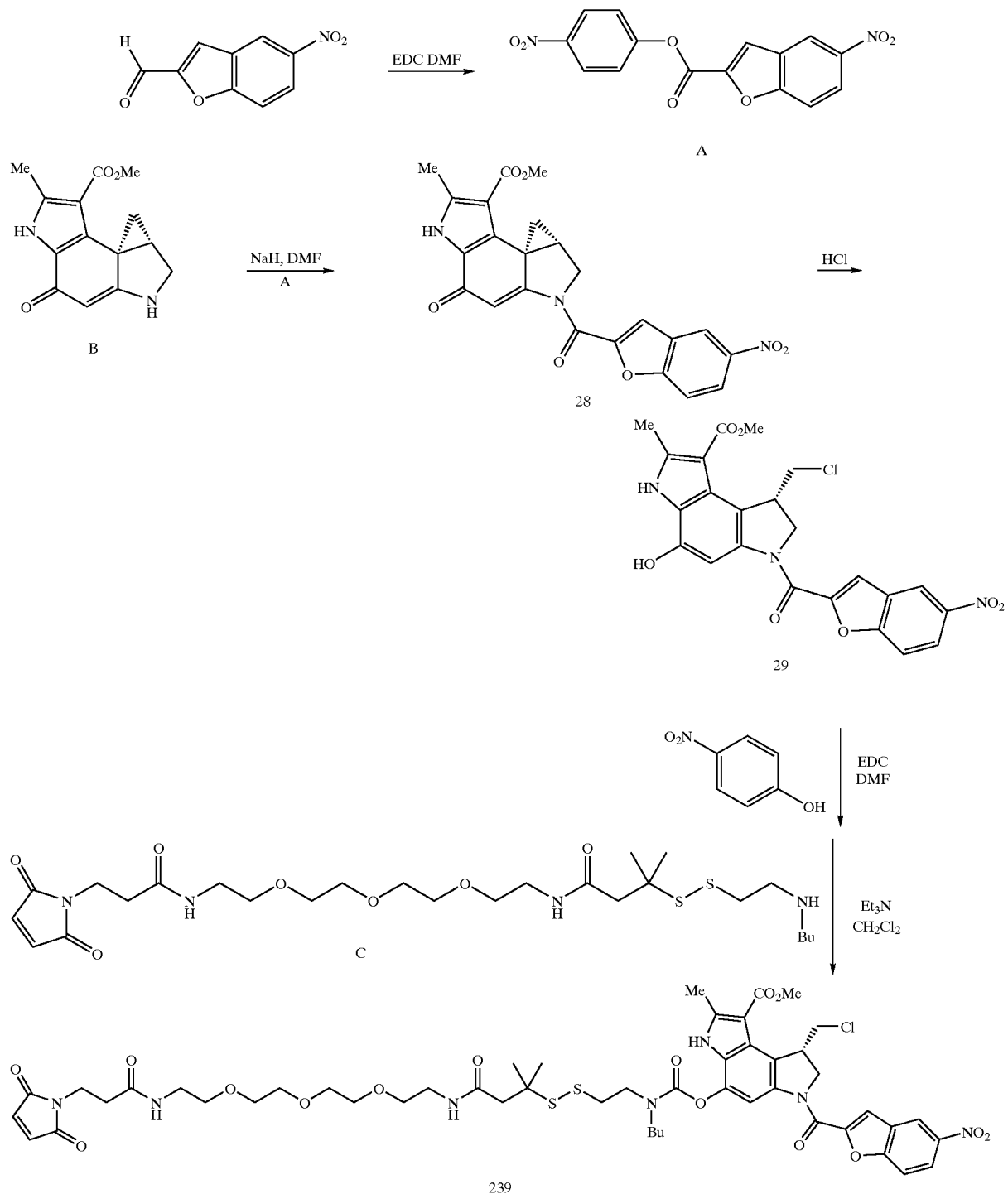

3.1a Synthesis of Compound 239

The compounds of Formula I are readily prepared by reacting the appropriate spirocyclopropylcyclohexadienly analog (Compounds B) with the activated heterocyclic compounds A using sodium hydride in N,B-dimethylformamide (DMF) or tetrahydrofuran (THF). The resulting compound 28 is then converted to compound 29 by treatment with the appropriate halo-acid, such as hydrochloric acid. Compound 29 activated as the 4-nitrophenylester and coupled with compound C to give compound 239, a compound of Formula I.

Other compounds of Formula I are prepared according to published procedures, which are modified to make additional analogs using procedures well known to those skilled in the art, such as reductions, oxidations, additions, aqueous extractions, evaporation, and purification.

3.1b Synthesis of Compound A

To a solution of 5-nitro-2-carboxylic acid (0.83 g, 4.0 mmol) in N,N-dimethylformamide (60 mL) at 0° C. was added EDC (1.15 g, 6.0 mmol). The resulting suspension was stirred at 0° C. for 45 min, by which time the EDC had completely dissolved. 4-Nitrophenol (0.83 g, 6.0 mmol) and DMAP (0.73 g, 6.0 mmol) were added and the resulting mixture stirred at ambient temperature. After 13 hours, the mixture was diluted with ethyl acetate and washed with a 10% aqueous citric acid solution twice, followed by water, and brine, then dried over $Na_2SO_4$, filtered and concentrated in vacuo. Purification of the resultant residue by flash column chromatography on silica gel (7% ethyl acetate in methylene chloride) afforded 1.02 g (78%) of A as a yellow solid: $^1$H NMR (CDCl$_3$) δ9.0 (br s, 1 H), 8.2 (d, 2 H), 7.8 (m, 2 H), 7.4 (d, 2 H), 7.3 (s, 1 H), 6.8 (s, 1 H).

3.1c Synthesis of Compound 28

To a solution of B (20 mg, 0.08 mmol) in N,N-dimethylformamide (1.0 mL) at −40° C. was added a suspension of sodium hydride (4.0 mg, 0.1 mmol, 60% in oil) in N,N-dimethylformamide (1.0 mL). The resulting mixture was allowed to warm to 0° C. slowly (1.5 h), then cooled back to −40° C. A (37 mg, 0.1 mmol) was added and the mixture allowed to warm to 0° C. slowly (1.5 h) where it was kept for 20 min. The mixture was cooled to −30° C., quenched with acetic acid (10 υL), stirred for 10 min, diluted with ethyl acetate, then washed with water then brine. The organic layer was separated and dried over MgSO$_4$, filtered and concentrated in vacuo. Purification by flash column chromatography on silica gel (50% to 100% ethyl acetate in methylene chloride) afforded 16.3 mg (43%) of 28 as a slightly yellow solid: $^1$H NMR (CDCl$_3$) δ11.3 (br s, 1 H), 9.4 (br s, 1 H), 7.4 (m, 2 H), 7.1 (s, 1 H), 6.95 (s, 1 H), 6.8 (s, 1 H), 4.4 (s, 2 H), 3.8 (s, 3 H), 3.8 (m, 1 H), 2.6 (s, 3 H), 2.4 (dd, 1 H), 1.4 (m, 1 H). ESMS m/z 490 (M−H)$^-$.

3.1d Synthesis of Compound 29

To a solution of 28 (50 mg, 0.103 mmol) in N,N-dimethylformamide (1.0 mL) was treated with 1 mL of anhydrous hydrochloric acid (1.0 M in dioxane). The resulting solution was stirred at ambient temperature for 30 min, then concentrated of solvent. Purification of the resulting residue by flash column chromatography on silica gel (50% to 100% ethyl acetate in methylene chloride) afforded 50 mg (100%) of 29 as a slightly yellow solid: $^1$H NMR (CDCl$_3$) δ11.3 (br s, 1 H), 9.4 (br s, 1 H), 7.4 (m, 2 H), 7.1 (s, 1 H), 6.95 (s, 1 H), 6.8 (s, 1 H), 4.4 (s, 2 H), 3.8 (s, 3 H), 3.8 (m, 1 H), 2.6 (s, 3 H), 2.4 (dd, 1 H), 1.4 (m, 1 H).

3.1e Synthesis of Compound 239

To a suspension of 29 (24 mg, 0.05 mmol) in methylene chloride (5 ml) at −78° C. was added 4-nitrophenyl chloroformate (40 mg, 0.2 mmol), and triethylamine (28 μl, 0.2 mmol). The reaction mixture was allowed to warm to room temperature, then concentrated in vacuo. The resulting residue was washed with diethyl ether, then dried over vacuum to give 9 as a yellow solid. Yellow solid 9 (19 mg, 0.029 mmol) in was dissolved in methylene chloride (3 ml) and the amine C (20 mg, 0.029 mmol) was added, followed by triethylamine (8.3 μl, 0.06 mmol). The reaction was stirred for 16 hours then concentrated in vacuo. The resulting residue was purified by flash chromatography using silica gel and 40:1 methylene chloride:methanol to give 12 mg (45% yield) of 239 as a yellow solid: $^1$H NMR (CDCl$_3$): δ9.9 (s, 1H), 9.7 (s, 1H), 8.7 (s, 1H), 8.4 (dd, 1H), 8.3 (d, 1H), 8.1 (br s, 1H), 7.75(d, 1H), 7.65 (s, 1H), 6.7(m, 2H), 4.75 (m, 1H), 4.55 (m, 2H), 3.9 (m, 4H), 3.8 (m, 4H), 3.5 (m, 18H), 3.0 (m, 2H), 2.7 (s, 3H), 2.5 (m, 4H), 1.7 (m, 2H), 1.4 (m, 10H), 1.0 (m, 2H), ESMS m/z 1100 (M−H)$^-$.

In a similar manner the following compounds were made:

238: $^1$H NMR (CDCl$_3$): δ10.3 (s, 1H), 8.7 (s, 1H), 8.5 (m, 1H), 8.4 (d, 1H), 8.2 (br s, 1H), 7.7 (m, 4H), 7.2 (m, 1H), 4.8 (m, 1H), 4.6 (m, 2H), 3.9 (m, 4H), 3.7 (m, 2H), 3.4 (m, 1H), 3.2 (m, 2H), 2.9 (s, 3H), 2.5 (s, 3H).

ESMS m/z 710 (M−H)$^-$.

242: $^1$H NMR (CDCl$_3$): δ9.7 (br s, 1H), 9.0 (br s, 1H), 8.6 (s, 1H), 8.4 (d, 1H), 8.1 (br s, 1H), 7.7 (m, 1H), 7.5 (m, 1H), 7.4 (m, 1H), 4.7 (d, 1H), 4.5 (m, 2H), 3.9 (s, 4H), 3.8 (m, 1H), 3.6 (m, 1H), 3.4 (m, 1H), 3.0 (m, 5H), 2.6 (s, 3H), 2.5 (m, 2H), 1.5 (m, 9H), 1.4 (m, 6H).

244: $^1$H NMR (CDCl$_3$): δ8.6 (br s, 1H), 8.4 (d, 1H), 8.1 (m, 1H), 7.7 (m, 6H), 6.9 (m, 2H), 4.75 (m, 1H), 4.55 (m, 2H), 4.1(m, 2H), 3.9 (m, 4H), 3.7 (m, 12H), 3.5 (m, 2H), 3.4 (m, 3H), 3.2 (m, 3H), 3.1 (m, 5H), 2.7 (s, 6H), 2.1 (m, 2H), 1.5 (s, 6H).

248: $^1$H NMR (CDCl$_3$): δ9.9 (s, 1H), 9.3 (br s, 1H), 8.1 (m, 1H), 7.5 (m, 3H), 7.1 (m, 2H), 4.8 (d, 1H), 4.5 (m, 2H), 3.95 (s, 3H), 3.85 (s, 3H), 3.8 (m, 1H), 3.7 (m, 2H), 3.4 (m, 1H), 3.0 (m, 8H), 2.5 (m, 2H), 1.5 (dd, 6H), 1.3 (s, 9H).

250: $^1$H NMR (CDCl$_3$): δ9.4 (s, 1H), 8.6 (s, 1H), 8.3 (m, 1H), 8.1 (m, 1H), 7.9 (m, 2H), 7.5 (m, 7H), 7.1 (m, 4H), 4.8 (m, 1H), 4.5 (m, 2H), 4.3 (m, 1H), 4.95 (s, 3H), 4.85 (s, 3H), 4.7 (m, 1H), 3.4 (m, 1H), 3.1 (m, 4H), 2.7 (s, 3H), 2.2 (s, 3H), 1.5 (s, 6H),

272: $^1$H NMR (DMSO): δ12.0 (m, 1H), 8.8 (br s, 1H), 8.3 (m, 1H), 7.9 (m, 3H), 7.7 (m, 3H), 6.9 (m, 2H), 4.85 (s, 1H), 4.7 (m, 1H), 4.5 (m, 3H), 3.8 (m, 4H), 3.6 (m, 4H), 3.4 (m, 5H), 3.1 (m, 6H), 2.7 (s, 3H), 2.2 (m, 2H), 1.4 (s, 6H).

Example 4

Proliferation Assays

The assay which was selected for measuring the biological activity of the cytotoxic compounds is the well established $^3$H-thymidine proliferation assay. This is a convenient method for quantitating cellular proliferation as it evaluates DNA synthesis by measuring the incorporation of exogenous radiolabeled $^3$H-thymidine. This assay is highly reproducible and can accommodate large numbers of compounds.

Promyelocytic leukemia cells, HL-60, were cultured in RPMI media containing 10% heat inactivated fetal calf serum (FCS). On the day of the study, the cells were collected, washed and resuspended at a concentration of $0.5 \times 10^6$ cells/ml in RPMI containing 10% FCS. 100?l of cell suspension was added to 96 well plates. Serial dilutions (3-fold increments) of doxorubicin or test compounds were made and 100 μl of compounds were added per well. Finally 10 μl of a 100 μCi/ml $^3$H-thymidine was added per well and the plates were incubated for 24 hours. The plates were harvested using a 96 well Harvester (Packard Instruments) and counted on a Packard Top Count counter. Four parameter logistic curves were fitted to the $^3$H-thymidine incorporation as a function of drug molarity using Prism software to determine IC$_{50}$ values.

The compounds of the invention generally have an IC$_{50}$ value in the above assay of from about 1 pM to about 100 nM, preferably from about 10 pM to about 10 nM.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the present invention has been described with reference to the specific embodiments thereof, it should be understood by those skilled in the art that various changes may be made and equivalents may be substituted without departing from the true spirit and scope of the invention and the appended claims. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the structure:

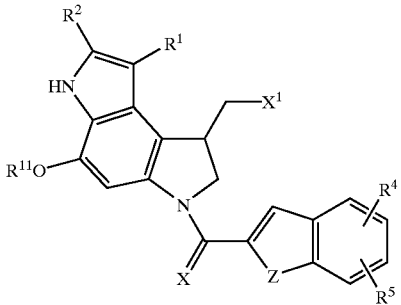

or a pharmaceutically acceptable salt thereof;
wherein
X and Z are members independently selected from O, S and $NR^{23}$
wherein
$R^{23}$ is a member selected from H, substituted or unsubstituted alkyl, substituted or unsubstituted heteroalkyl, and acyl;
$R^1$ is H, substituted or unsubstituted lower alkyl or $C(O)R^8$, wherein $R^8$ is a member selected from $NR^9R^{10}$ and $OR^9$,
in which
$R^9$, and $R^{10}$ are members independently selected from H, substituted or unsubstituted alkyl and substituted or unsubstituted heteroalkyl;
$R^2$ is H or substituted or unsubstituted lower alkyl;
$R^{11}$ is $C(O)NR^{12}R^{13}$, in which
$R^{12}$ and $R^{13}$ are members independently selected from H, substituted or unsubstituted alkyl, substituted or unsubstituted heteroalkyl and substituted or unsubstituted aryl, and at least one of $R^{12}$ and $R^{13}$ comprises an enzymatically cleaveable disulfide group
$R^4$ and $R^5$ are members independently selected from H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $OR^{15}$
wherein
$R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms; and
$X^1$ is a leaving group.

2. The compound according to claim 1, wherein said leaving group is a member selected from halogen, azide, alkylsulfonyl and arylsulfonyl.

3. The compound according to claim 1, wherein $R^1$ is $CO_2CH_3$.

4. The compound according to claim 1, wherein $R^2$ is $CH_3$.

5. The compound according to claim 1, wherein $R^1$ is $CO_2CH_3$, and $R^2$ is $CH_3$.

6. The compound according to claim 5, wherein $R^4$ and $R^5$ are members independently selected from H, halogen, $NH_2$, $O(CH_2)_2NMe_2$ and $NO_2$.

7. The compound according to claim 1, wherein at least one of $R^4$ and $R^5$ is other than a member selected from H and $OCH_3$.

8. The compound according to claim 5, wherein X is O; and Z is O.

9. The compound according to claim 1, wherein a member selected from $R^4$ and $R^5$ is:

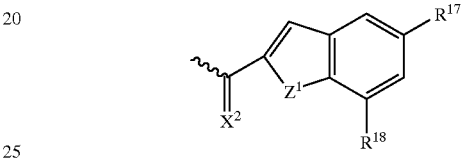

wherein
$X^2$ and $Z^1$ are members independently selected from O, S and $NR^{23}$;
$R^{17}$ and $R^{18}$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, halogen, $NO_2$, $NR^{19}R^{20}$, $NC(O)R^{19}$, $OC(O)NR^{19}$, $OC(O)OR^{19}$, $C(O)R^{19}$, $OR^{19}$
wherein
$R^{19}$ and $R^{20}$ are independently selected from substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted peptidyl, wherein $R^{19}$ and $R^{20}$ together with the nitrogen atom to which they are attached are optionally joined to form a substituted or unsubstituted heterocycloalkyl ring system having from 4 to 6 members, optionally containing two or more heteroatoms.

10. The compound according to claim 9, wherein $X^2$ is O; and $Z^1$ is a member selected from O and $NR^{23}$.

11. The compound according to claim 1, wherein $R^{11}$ has the structure:

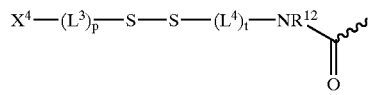

wherein
$X^4$ is a member selected from protected reactive functional groups, unprotected reactive functional groups, detectable labels and targeting agents;
$L^3$ is a linker selected from substituted or unsubstituted alkyl and substituted or unsubstituted heteroalkyl groups;
$L^4$ is a linker selected from substituted or unsubstituted alkyl and substituted or unsubstituted heteroalkyl groups; and p and t are integers independently selected from 0 and 1.

12. The compound according to claim 11, wherein $L^4$ is a substituted or unsubstituted ethylene moiety.

13. The compound according to claim 11, wherein $X^4$ is a member selected from $R^{29}$, $COOR^{29}$, $C(O)NR^{29}$, and $C(O)NNR^{29}$ wherein
$R^{29}$ is a member selected from substituted or unsubstituted alkyl, substituted or unsubstituted heteroalkyl and substituted or unsubstituted heteroaryl.

14. The compound according to claim 13, wherein $R^{29}$ is a member selected from: H; OH; $NHNH_2$;

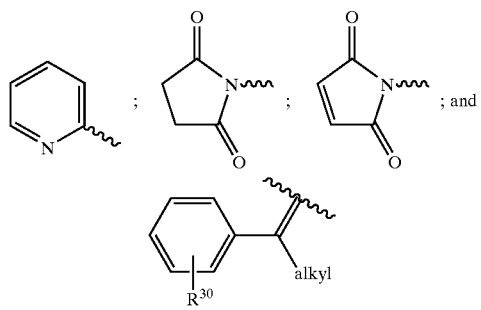

; and wherein
$R^{30}$ is a member selected from substituted or unsubstituted alkyl terminated with a reactive functional group, substituted or unsubstituted heteroaryl terminated with a functional group and $-(L^3)_p X^4$, wherein each $L^3$, $X^4$ and p are independently selected.

15. The compound according to claim 11, wherein said compound is conjugated to another molecule via $X^4$.

16. The compound according to claim 11, wherein said detectable label is fluorophore.

17. The compound according to claim 11, wherein said targeting agent is a biomolecule.

18. The compound according to claim 20, wherein said biomolecule is a member selected from antibodies, receptors, peptides, lectins, saccharides, nucleic acids and combinations thereof.

19. A pharmaceutical formulation comprising a compound according to claim 1 and a pharmaceutically acceptable carrier.

20. A method of killing a cell, said method comprising administering to said cell an amount of a compound according to claim 1 sufficient to kill said cell.

21. A method of killing a carcinoma cell in a subject bearing said cell, said method comprising administering to said subject an amount of a compound according to claim 1, sufficient to kill said cell.

* * * * *

UNITED STATES PATENT AND TRADEMARK OFFICE
CERTIFICATE OF CORRECTION

PATENT NO. : 6,989,452 B2
APPLICATION NO. : 10/161233
DATED : January 24, 2006
INVENTOR(S) : Howard P. Ng et al.

It is certified that error appears in the above-identified patent and that said Letters Patent is hereby corrected as shown below:

Item [56] in the Related U.S. Application Data:

Line 3, Delete "13, 2001," and insert -- 31, 2001, --.

Column 7, Line 62, Delete "–Si(CH$_3$)$_3$)$_3$" and insert -- –Si(CH$_3$)$_3$, --.

Column 15, Line 42 (Approx.), Delete "an" and insert -- and --.

Column 15, Line 42 (Approx.), After "H" insert -- , --.

Column 23, Line 23 (Approx. Scheme 1), Delete "EDC1" and insert -- EDCI --.

Column 24, Line 37 (Approx. Scheme 2), Delete "EDC1" and insert -- EDCI --.

Column 31, Line 2 (Approx.), Delete "EDC1" and insert -- EDCI --.

Column 41, Line 49, After "or" delete "id".

Column 55, Line 29, After "(s, 1H)" insert -- . --.

Column 55, Line 45, Delete "(s 1H)," and insert -- (s, 1H), --.

Column 57, Line 1, Delete "(M-H)$^{31}$." and insert -- (M-H)$^-$. --.

Column 58, Line 41 (Approx.), Delete "(m, 1)," and insert -- (m, 1H), --.

Column 58, Line 66, Delete "(in, 1H)," and insert -- (m, 1H), --.

Column 58, Line 67, Delete "(in, 3H)," and insert -- (m, 3H), --.

Column 58, Line 67, After "4.6" delete "(in, 1H)," and insert -- (m, 1H), --.

UNITED STATES PATENT AND TRADEMARK OFFICE
CERTIFICATE OF CORRECTION

PATENT NO. : 6,989,452 B2
APPLICATION NO. : 10/161233
DATED : January 24, 2006
INVENTOR(S) : Howard P. Ng et al.

It is certified that error appears in the above-identified patent and that said Letters Patent is hereby corrected as shown below:

Column 58, Line 67, After "4.45" delete "(in, 1H)," and insert -- (m, 1H), --.

Column 63, Line 2 (Structure) Delete " 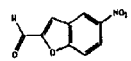 " and insert -- 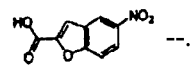 --.

Column 66, Line 2, Delete "(m, 2H)," and insert -- (m, 2H). --.

Column 66, Line 27 (Approx.), Delete "(s,6H)," and insert -- (s, 6H). --.

Column 66, Line 37, Delete "H-thymidine" and insert -- $^3$H-thymidine --.

Column 70, Line 10 (Approx.), In Claim 16, after "is" insert -- a --.

Signed and Sealed this

Second Day of December, 2008

JON W. DUDAS
*Director of the United States Patent and Trademark Office*